(12) United States Patent
Bergstrom

(10) Patent No.: US 7,456,167 B2
(45) Date of Patent: Nov. 25, 2008

(54) CYCLOPROPYL FUSED INDOLOBENZAZEPINE HCV NS5B INHIBITORS

(75) Inventor: Carl P. Bergstrom, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/753,137

(22) Filed: May 24, 2007

(65) Prior Publication Data

US 2007/0275947 A1 Nov. 29, 2007

Related U.S. Application Data

(60) Provisional application No. 60/808,331, filed on May 25, 2006.

(51) Int. Cl.
*A61K 31/55* (2006.01)
*A61P 31/00* (2006.01)
*C07D 223/14* (2006.01)

(52) U.S. Cl. .................. 514/214.01; 540/576
(58) Field of Classification Search ............ 514/214.01; 540/576
See application file for complete search history.

(56) References Cited

U.S. PATENT DOCUMENTS

| 7,153,848 B2 | 12/2006 | Hudyma et al. ........ 514/214.01 |
| 2006/0166964 A1 | 7/2006 | Hudyma et al. ........ 514/211.09 |
| 2007/0060565 A1 | 3/2007 | Meanwell et al. ...... 514/214.01 |
| 2007/0078122 A1 | 4/2007 | Bergstrom et al. ..... 514/214.01 |
| 2007/0185083 A1 | 8/2007 | Bergstrom et al. ..... 514/214.01 |

FOREIGN PATENT DOCUMENTS

| WO | WO2005/080399 | 9/2005 |
| WO | WO2006/040039 | 4/2006 |
| WO | WO2006/046030 | 5/2006 |
| WO | WO2007/029029 | 3/2007 |

OTHER PUBLICATIONS

U.S. Appl. No. 11/752,354, filed May 23, 2007, Robert G. Gentles, et al.
U.S. Appl. No. 11/753,137, filed May 24, 2007, Carl P. Bergstrom.
U.S. Appl. No. 11/756,203, filed May 31, 2007, Kap-Sun Yeung, et al.

*Primary Examiner*—Brenda L Coleman
(74) *Attorney, Agent, or Firm*—James Epperson

(57) ABSTRACT

The invention encompasses compounds of formula I as well as compositions and methods of using the compounds. The compounds have activity against hepatitis C virus (HCV) and are useful in treating those infected with HCV.

12 Claims, No Drawings

CYCLOPROPYL FUSED INDOLOBENZAZEPINE HCV NS5B INHIBITORS

CROSS REFERENCE TO RELATED APPLICATIONS

This application claims the benefit of U.S. Provisional Application Ser. No. 60/808,331, filed May 25, 2006.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

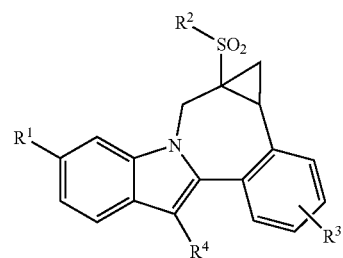

where:

$R^1$ is $CO_2R^5$ or $CONR^6R^7$;

$R^2$ is hydroxy, alkoxy, benzyloxy, amino, alkylamino, dialkylamino, (aminoalkyl)amino, (aminoalkyl)(alkyl)amino, di(aminoalkyl)amino, ((alkylamino)alkyl)amino, ((alkylamino)alkyl)(alkyl)amino, di((alkylamino)alkyl)amino, ((dialkylamino)alkyl)amino, ((dialkylamino)alkyl)(alkyl)amino, di((dialkylamino)alkyl)amino, (($COR^{11}$)alkyl)amino, (($COR^{11}$)alkyl)(alkyl)amino, alkyl, haloalkyl, aminoalkyl, (alkylamino)alkyl, (dialkylamino)alkyl, or $(R^{12})$alkyl;

or $R^2$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from the group consisting of hydroxy, amino, alkylamino, dialkylamino, alkyl, alkoxyalkyl, aminoalkyl, (alkylamino)alkyl, (dialkylamino)alkyl, alkyl$SO_2$, and haloalkyl$SO_2$;

or $R^2$ is

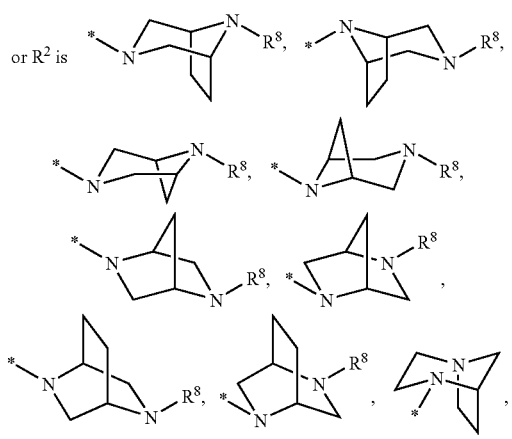

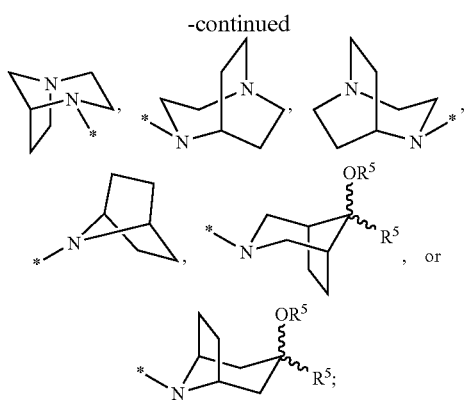

or $R^2$ is a [4.3.0] or [3.3.0] bicyclic diamine attached to the $SO_2$ moiety through one nitrogen, and is substituted with 0-2 $R^8$ substituents;

$R^3$ is hydrogen, halo, alkyl, alkenyl, hydroxy, benzyloxy, alkoxy, or haloalkoxy;

$R^4$ is cycloalkyl;

$R^5$ is hydrogen or alkyl;

$R^6$ is hydrogen, alkyl, alkyl$SO_2$, cycloalkyl$SO_2$, haloalkyl$SO_2$, $(R^9)_2NSO_2$, or $(R^{10})SO_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, alkyl$SO_2$, cycloalkyl$SO_2$, haloalkyl$SO_2$, aminocarbonyl, (alkylamino)carbonyl, (dialkylamino)carbonyl, benzyl, benzyloxycarbonyl, or pyridinyl;

$R^9$ is hydrogen, alkyl, or cycloalkyl; and $R^{10}$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 alkyl substituents;

$R^{11}$ is azetidinyl, pyrrolidinyl, piperidinyl, piperazinyl, N-alkylpiperazinyl, morpholinyl, thiomorpholinyl, homopiperidinyl, homopiperazinyl, N-alkylhomopiperazinyl, or homomorpholinyl; and $R^{12}$ is azetidinyl, pyrrolidinyl, piperidinyl, piperazinyl, N-alkylpiperazinyl, morpholinyl, thiomorpholinyl, homopiperidinyl, homopiperazinyl, N-alkylhomopiperazinyl, or homomorpholinyl;

or a pharmaceutically acceptable salt thereof.

Another aspect of the invention is a compound of formula I where $R^1$ is $CONR^6R^7$; $R^6$ is alkyl$SO_2$, cycloalkyl$SO_2$, haloalkyl$SO_2$, $(R^9)_2NSO_2$, or $(R^{10})SO_2$; and $R^7$ is Hydrogen.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $(R^9)_2NSO_2$ or $(R^{10})SO_2$.

Another aspect of the invention is a compound of formula I where $R^6$ is (dimethylamino)$SO_2$.

Another aspect of the invention is a compound of formula I where $R^6$ is alkyl$SO_2$.

Another aspect of the invention is a compound of formula I where $R^6$ is isopropyl$SO_2$.

Another aspect is where $R^8$ is hydrogen, alkyl, alkyl$SO_2$, or benzyl

Another aspect of the invention is a compound of formula I according to the following stereochemistry.

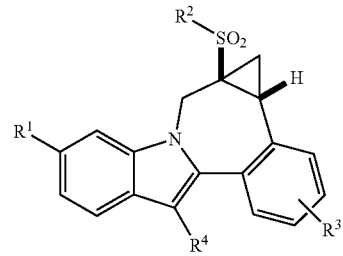

Another aspect of the invention is a compound of formula I according to the following stereochemistry.

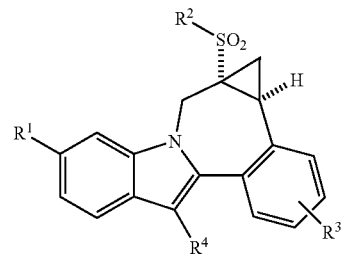

Any scope of any variable, including $R^1$, $R^2$, $R^3$, $R^4$, $R^5$, $R^6$, $R^7$, $R^8$, $R^9$, $R^{10}$, $R^{11}$, or $R^{12}$, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

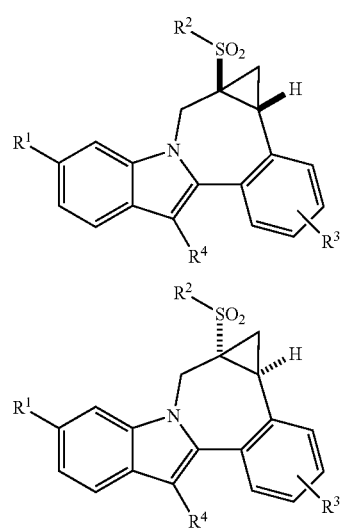

Synthetic Methods

The compounds may be made by methods known in the art including those described below. Some reagents and intermediates are known in the art. Other reagents and intermediates can be made by methods known in the art using available materials. The variables (e.g. numbered "R" substituents) used to describe the synthesis of the compounds are intended only to illustrate how to make the compounds and are not to be confused with variables used in the claims or in other sections of the specification.

Abbreviations used in the schemes generally follow conventions used in the art.

The compounds can be made by methods known in the art and described in the application. Some of the compounds can be synthesized by the methods illustrated in Scheme 1.

Scheme 1.

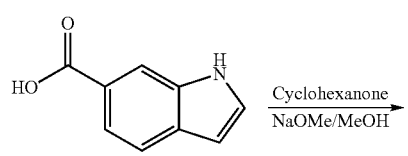

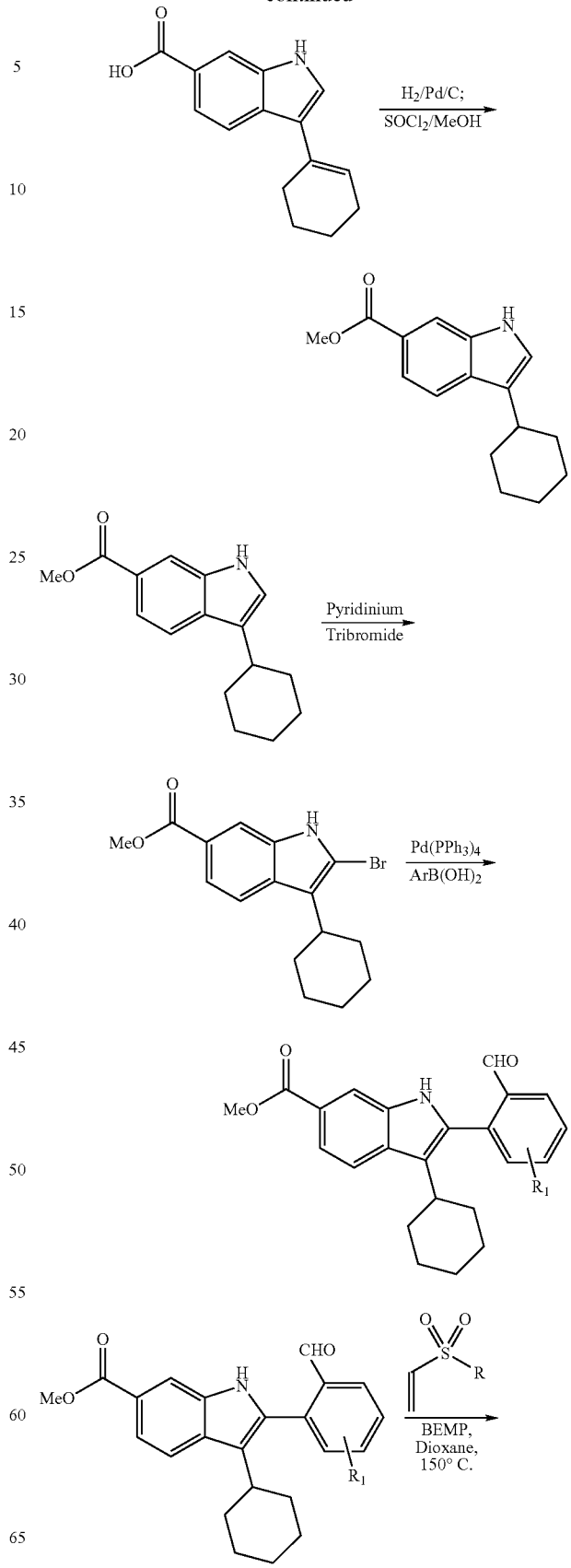

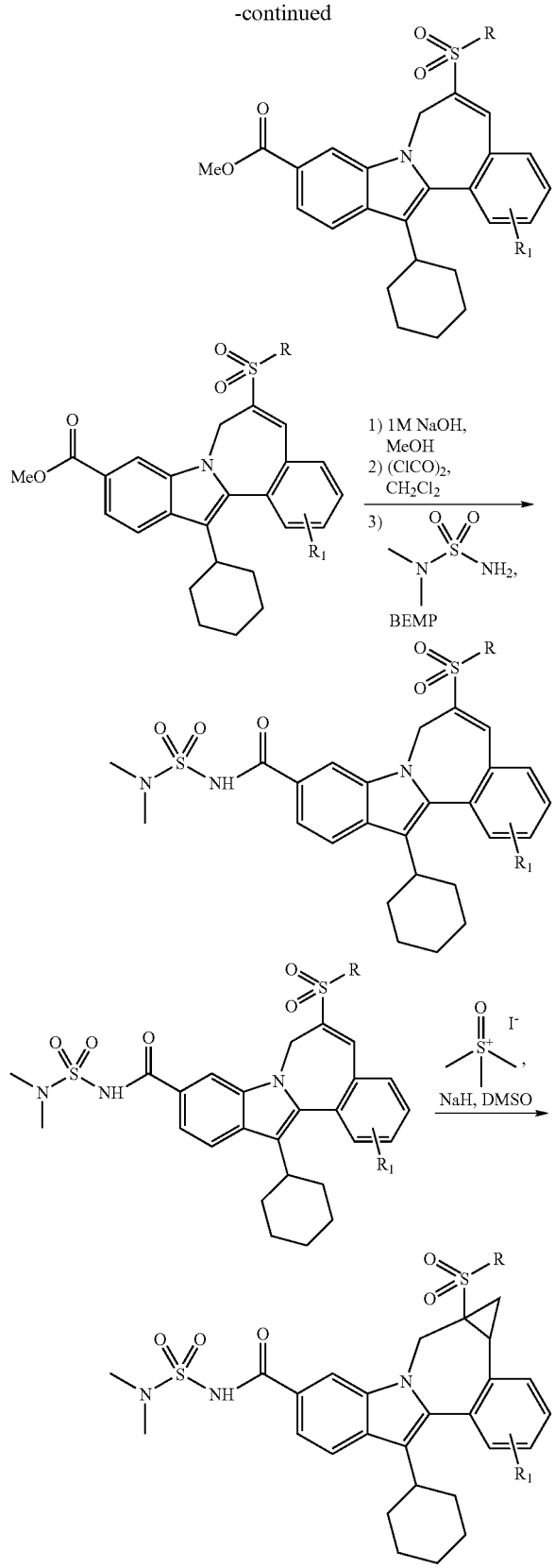

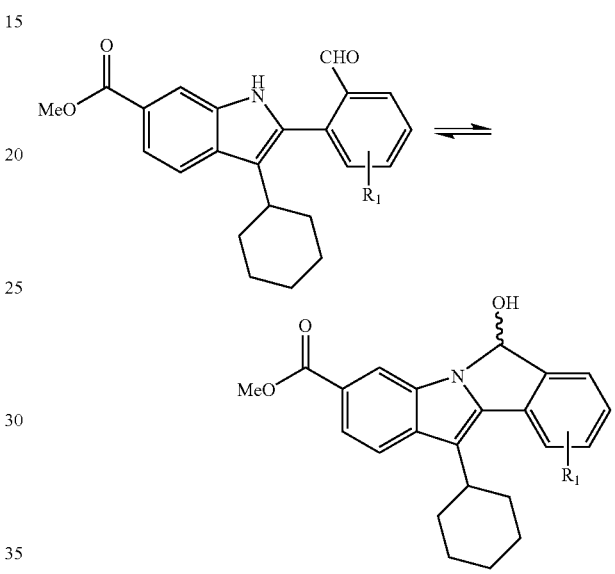

enyl-1H-indole-6-carboxylic acid. This indole ester can be subjected to sequential reduction and esterification to provide methyl 3-cyclohexanyl-1H-indole-6-carboxylate. Treatment of the resultant indole ester with pryridinium tribromide in a mixture of THF and chloroform can generate methyl 2-bromo-3-cyclohexanyl-1H-indole-6-carboxylate. This intermediate can be coupled with a variety of reagents and compounds. For example, 2-formyl-phenyl boronic acids using appropriate palladium catalysts can generate the aromatic aldehyde intermediates shown. These aryl aldehydes are sometimes observed to exist in equilibrium with the related ring-closed hemiaminals, as shown below.

These intermediates can be converted to sulfonyl or sulfonamide substituted indolobenzazepines as shown in scheme 1 among other methods. Subsequent hydrolysis and conversion of the intermediate acids to the related sulfonyl chlorides can be followed by coupling to a sulfonyl urea, using as an example, BEMP as base, to generate the intermediate sulfamide derivatives. These compounds can subsequently be converted in the fused cyclopropyl examples using methods known in the art, for example treatment with trimethylsulfoxonium iodide and sodium hydride in DMSO.

Scheme 2 illustrates a method for transforming esters into other functional groups.

Scheme 2.

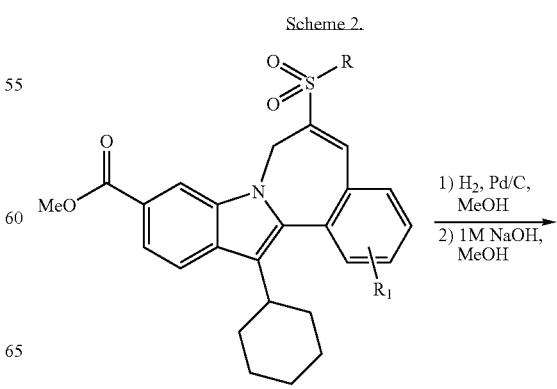

Condensation of 1H-indole-6-carboxylic acid with cyclohexanone under basic conditions can generate 3-cyclohex-

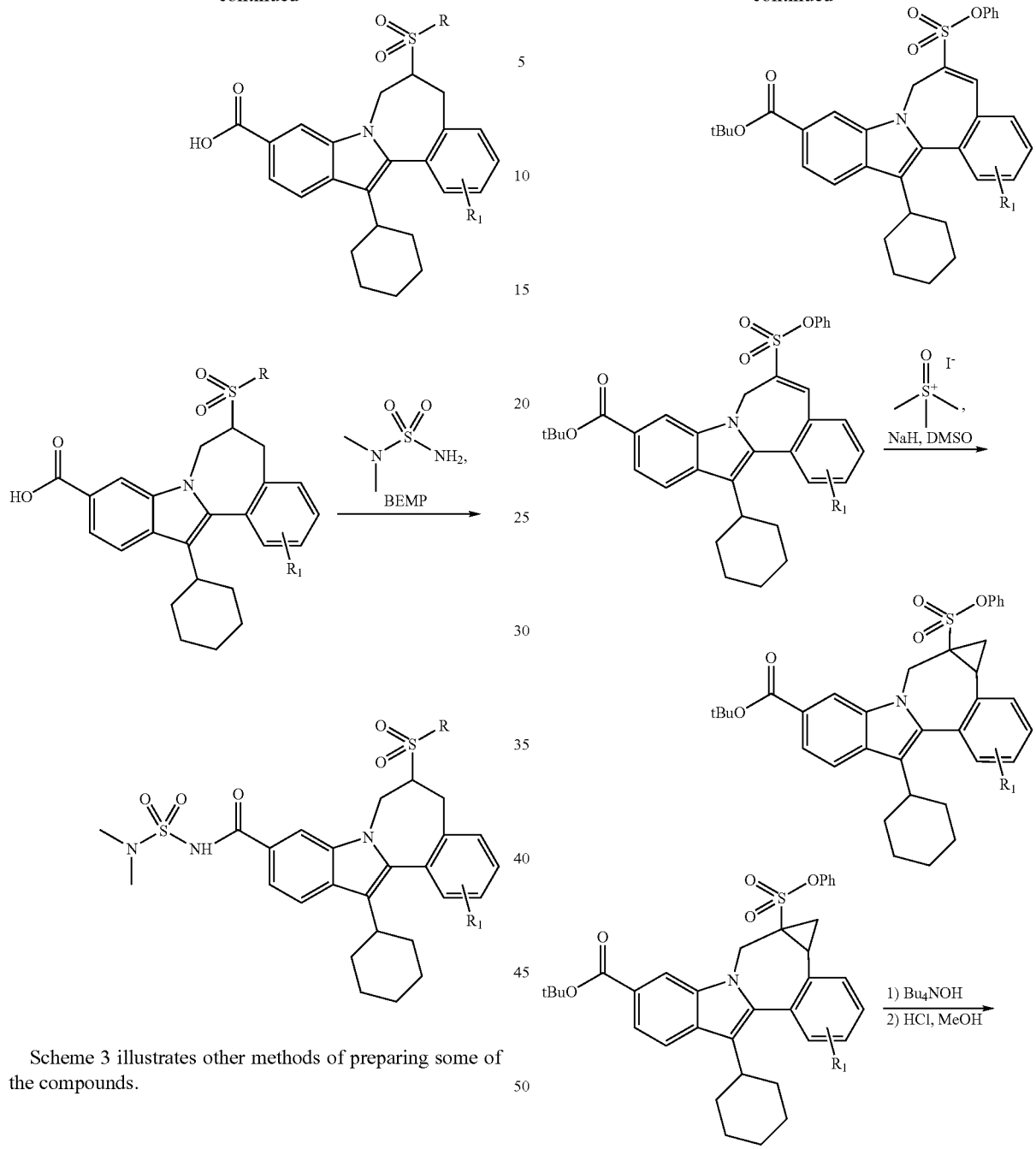
Scheme 3 illustrates other methods of preparing some of the compounds.
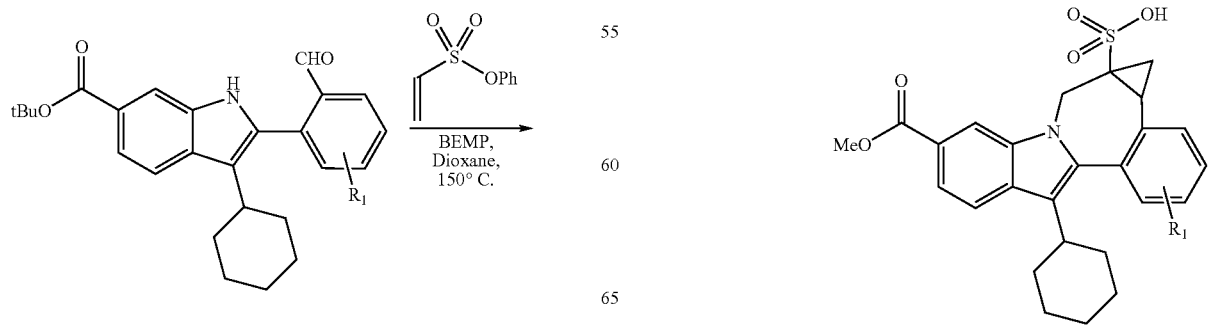

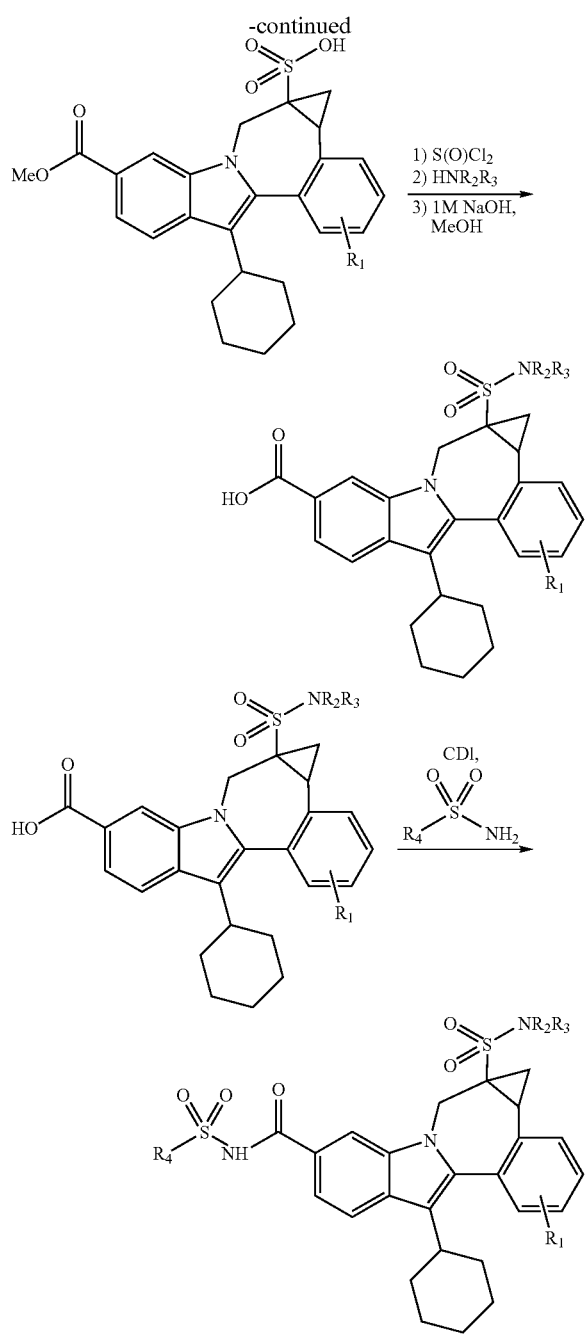

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.*

1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH$_2$O, NaCl added to 150 mM final, the FRET peptide diluted to 20 uM final from a 2 mM stock.

To prepare plates, HCV replicon cells, with or without a *Renilla luciferase* reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a CO$_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. EC$_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Structure | IC$_{50}$ (uM) | EC$_{50}$ (uM) |
|---|---|---|
|  | B | B |
|  | B | B |

TABLE 1-continued
| Structure | IC$_{50}$ (uM) | EC$_{50}$ (uM) |
|---|---|---|
| 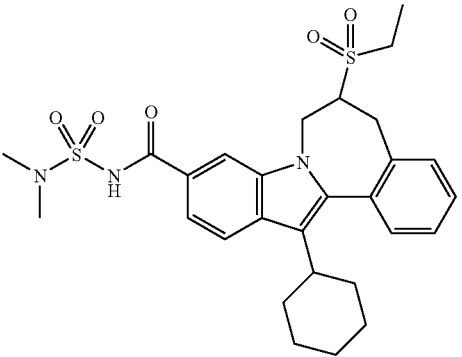 | B | B |
| 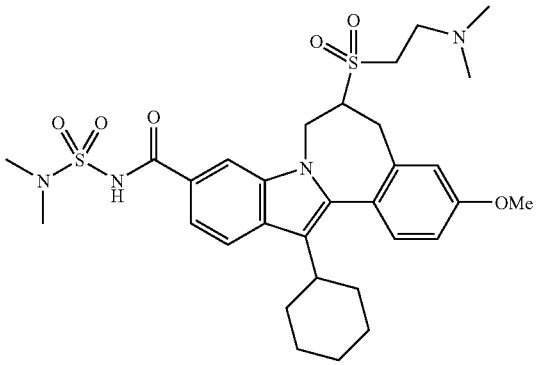 | B | B |
| 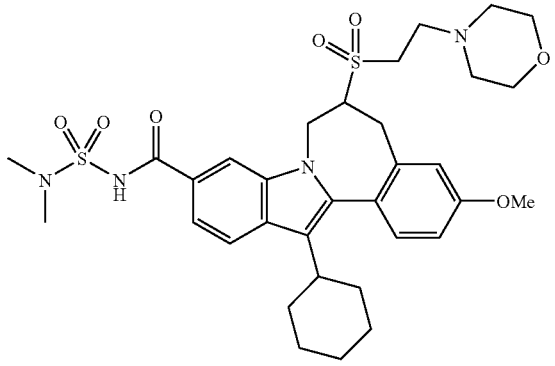 | B | B |
| 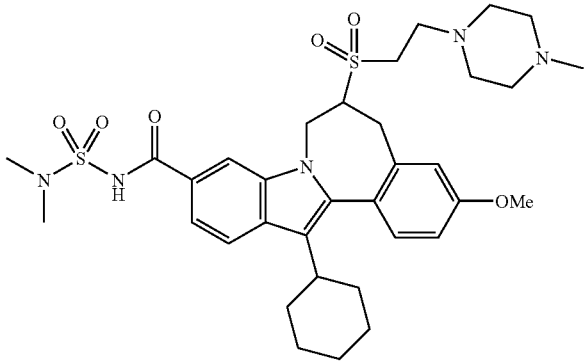 | B | B |

TABLE 1-continued
| Structure | IC$_{50}$ (uM) | EC$_{50}$ (uM) |
|---|---|---|
| 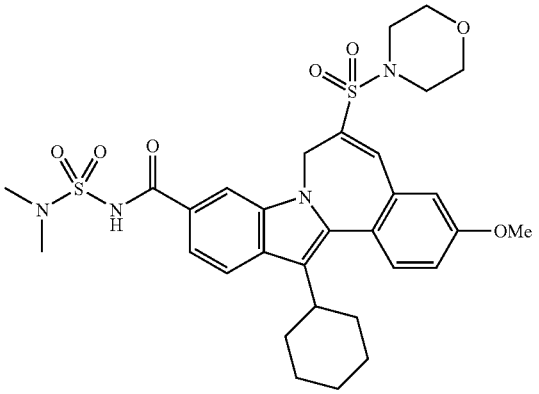 | B | B |
| 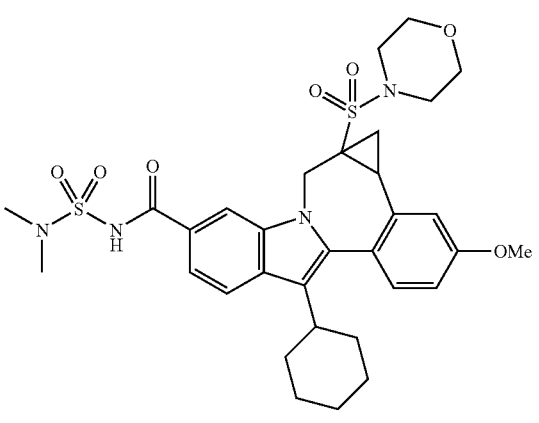 | B | B |
| 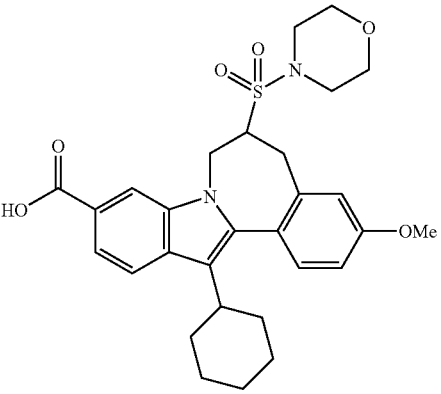 | B | B |
| 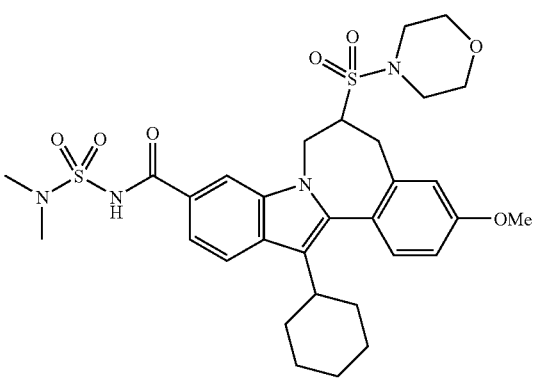 | B | B |

TABLE 1-continued

| Structure | IC$_{50}$ (uM) | EC$_{50}$ (uM) |
|---|---|---|
| | B | B |
| | B | B |
| | B | B |
| 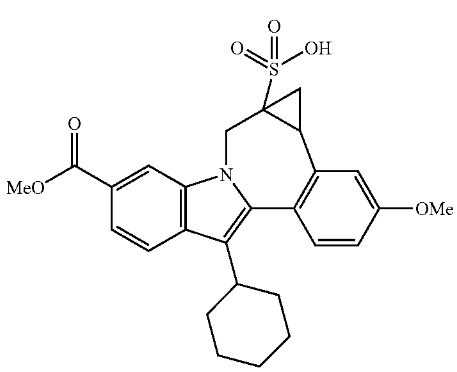 | E | A |

TABLE 1-continued

| Structure | IC$_{50}$ (uM) | EC$_{50}$ (uM) |
| --- | --- | --- |
| | B | B |
| | B | B |
| | B | B |

TABLE 1-continued

| Structure | IC$_{50}$ (uM) | EC$_{50}$ (uM) |
|---|---|---|
| | B | B |
| | B | D |
| | B | B |

TABLE 1-continued
| Structure | IC$_{50}$ (uM) | EC$_{50}$ (uM) |
|---|---|---|
| 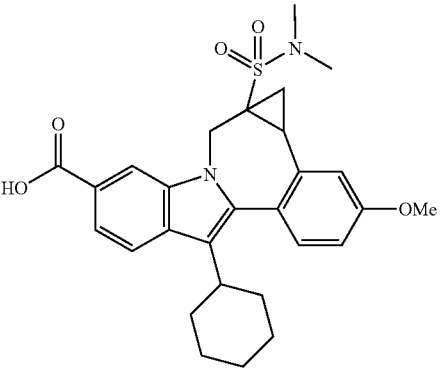 | D | B |
| 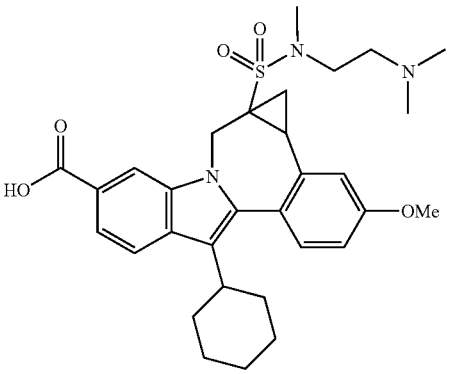 | B | B |
| 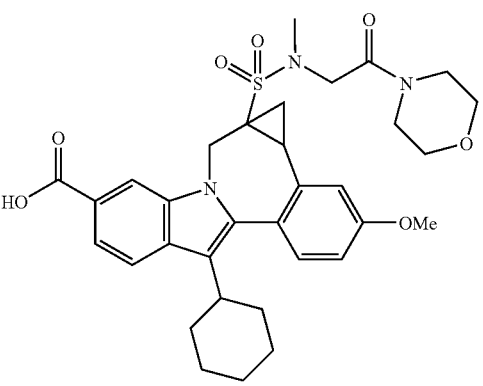 | B | B |
| 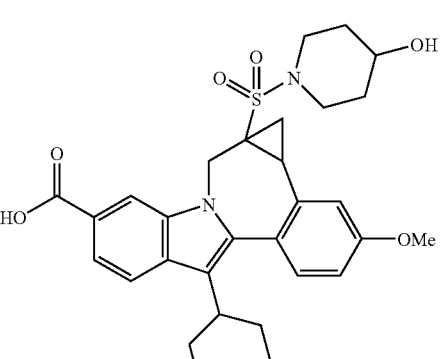 | B | B |

TABLE 1-continued

| Structure | IC$_{50}$ (uM) | EC$_{50}$ (uM) |
| --- | --- | --- |
| | B | B |
| | B | B |
| | B | B |

TABLE 1-continued
| Structure | IC$_{50}$ (uM) | EC$_{50}$ (uM) |
|---|---|---|
| 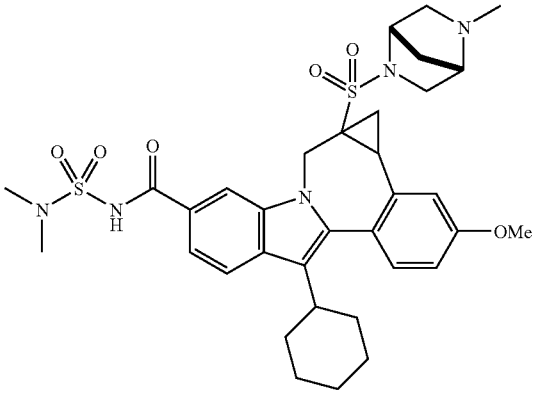 | B | B |
| 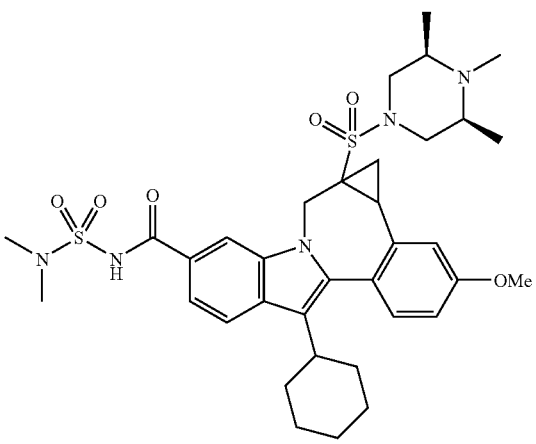 | B | B |
| 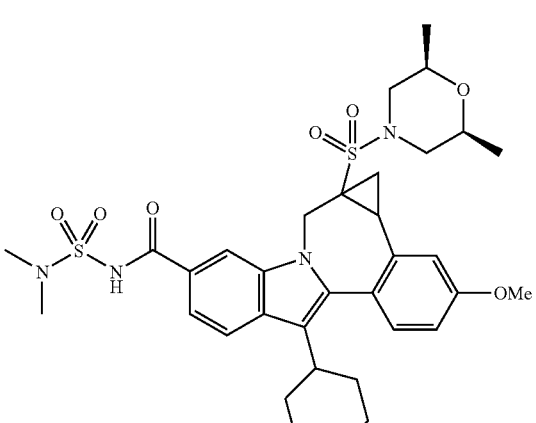 | B | B |

TABLE 1-continued
| Structure | IC$_{50}$ (uM) | EC$_{50}$ (uM) |
|---|---|---|
| 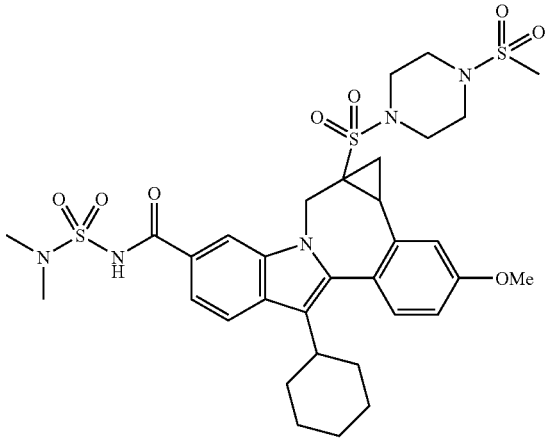 | B | B |
| 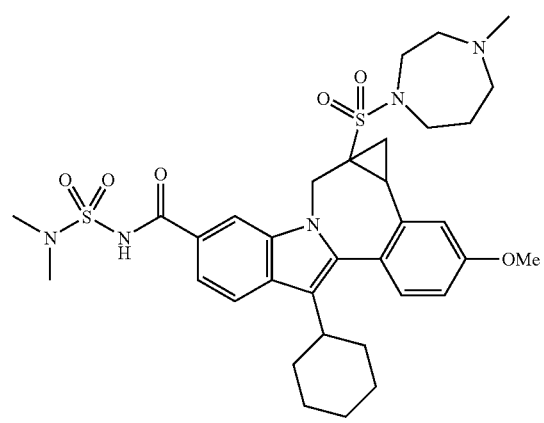 | B | B |
| 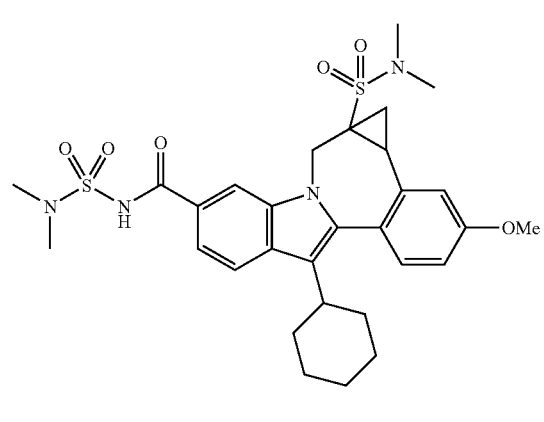 | B | B |

TABLE 1-continued
| Structure | IC$_{50}$ (uM) | EC$_{50}$ (uM) |
|---|---|---|
| 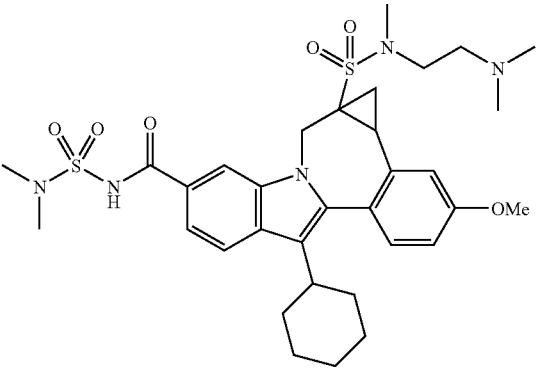 | B | B |
| 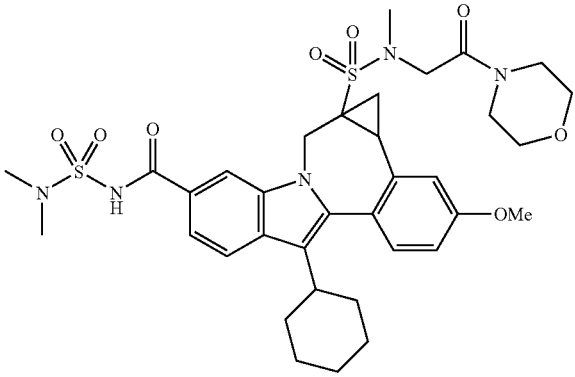 | B | B |
| 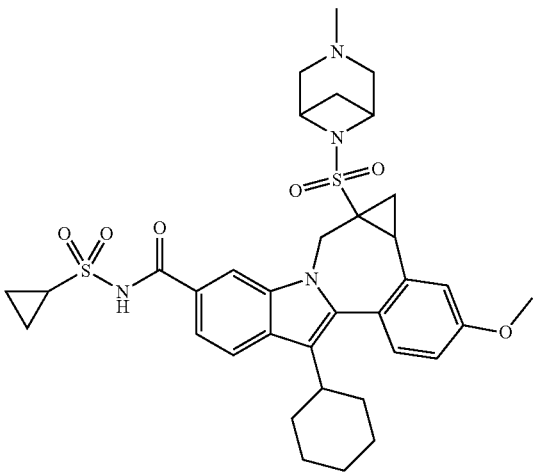 | B | B |

TABLE 1-continued

| Structure | IC$_{50}$ (uM) | EC$_{50}$ (uM) |
|---|---|---|
| | B | B |
| | B | B |
| | B | B |

TABLE 1-continued

| Structure | IC$_{50}$ (uM) | EC$_{50}$ (uM) |
|---|---|---|
| | B | B |
| | B | B |
| | B | B |
| | B | B |

TABLE 1-continued

| Structure | IC$_{50}$ (uM) | EC$_{50}$ (uM) |
|---|---|---|
| | B | B |
| | B | B |
| | B | B |
| | B | B |

TABLE 1-continued
| Structure | IC$_{50}$ (uM) | EC$_{50}$ (uM) |
| --- | --- | --- |
| 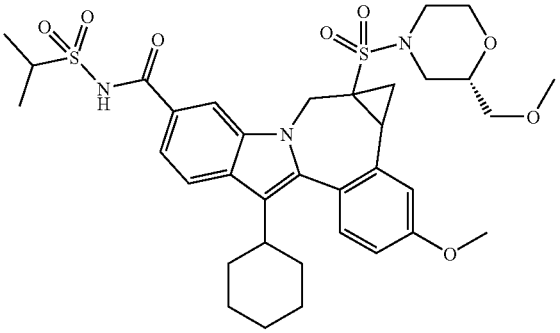 | B | B |
| 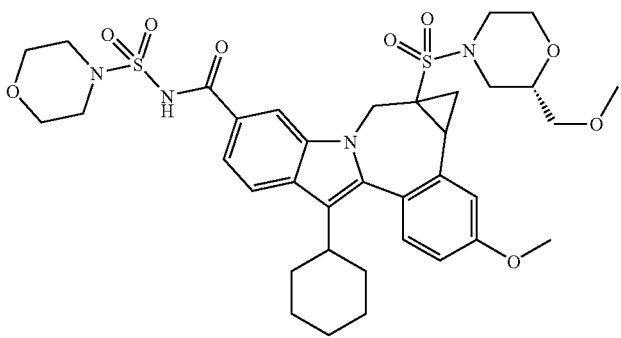 | B | B |
| 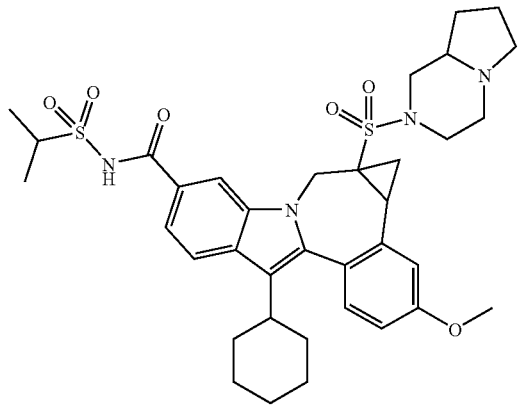 | B | B |
| 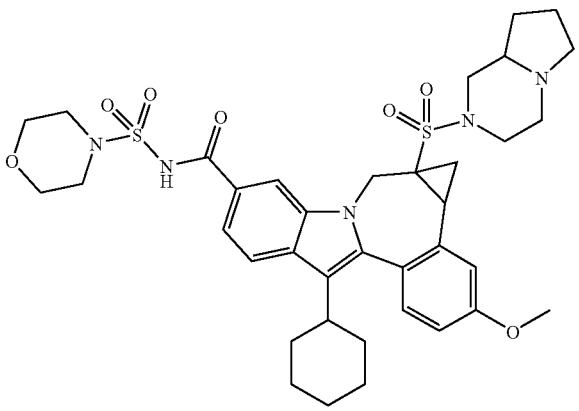 | B | B |

TABLE 1-continued
| Structure | IC$_{50}$ (uM) | EC$_{50}$ (uM) |
| --- | --- | --- |
| 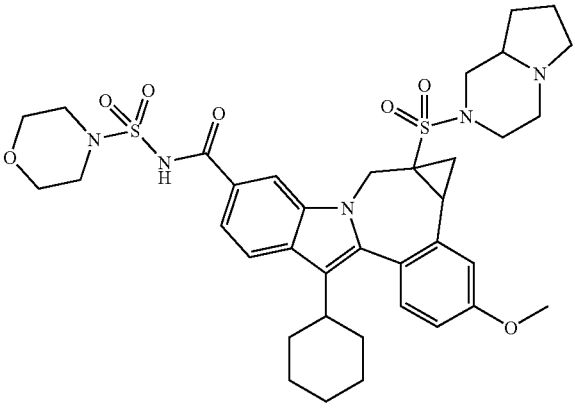 | B | B |
| 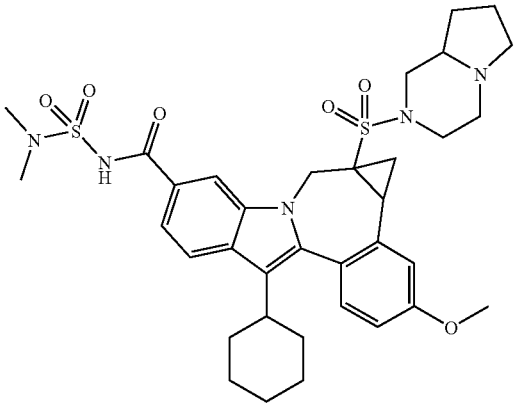 | B | B |
| 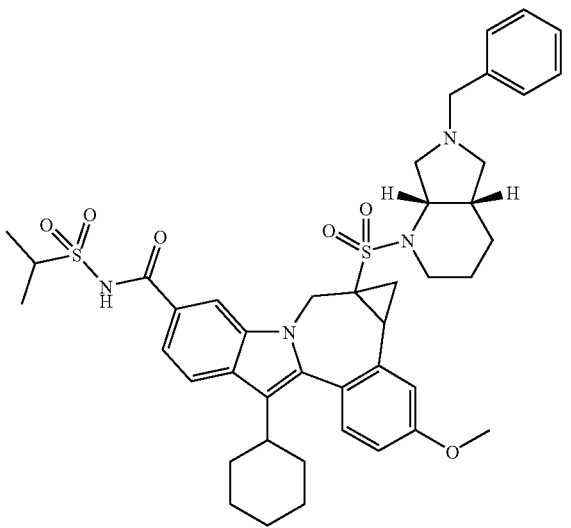 | | |

TABLE 1-continued

| Structure | IC$_{50}$ (uM) | EC$_{50}$ (uM) |
|---|---|---|
| | B | B |
| | | |
| | B | B |
| | B | B |

TABLE 1-continued

| Structure | IC$_{50}$ (uM) | EC$_{50}$ (uM) |
|---|---|---|
| | B | B |
| | B | B |
| | B | B |
| | B | B |

TABLE 1-continued

| Structure | IC$_{50}$ (uM) | EC$_{50}$ (uM) |
|---|---|---|
| | B | B |
| | B | B |
| | | |
| | | |

TABLE 1-continued

| Structure | IC$_{50}$ (uM) | EC$_{50}$ (uM) |
|---|---|---|
| | B | B |
| | B | B |
| | B | B |

TABLE 1-continued

| Structure | IC$_{50}$ (uM) | EC$_{50}$ (uM) |
|---|---|---|
| | B | B |
| | B | B |
| | B | B |

TABLE 1-continued

| Structure | IC$_{50}$ (uM) | EC$_{50}$ (uM) |
|---|---|---|
| | B | B |
| | B | B |

A >1 µM; B 0.02 µM-1 µM; C >10 µM; D 1 µM-10 µM; E 1.0 µM-0.07 µM; F <0.02 µM; G >0.37 µM. IC$_{50}$ values were determined using the preincubation protocol. EC$_{50}$ values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |

TABLE 2-continued

| Brand Name | Type of Inhibitor or Target | Source Company |
|---|---|---|
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/ Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

Unless otherwise specified, analytical LCMS data on the following intermediates and examples were acquired using the following columns and conditions. Stop time: Gradient time+1 minute; Starting conc: 0% B unless otherwise noted; Eluent A: 5% $CH_3CN$/95% $H_2O$ with 10 mM $NH_4OAc$ (for column A); 10% MeOH/90% $H_2O$ with 0.1% TFA (for column B); Eluent B: 95% $CH_3CN$/5% $H_2O$ with 10 mM $NH_4OAc$ (for column A); 90% MeOH/10% $H_2O$ with 0.1% TFA (for column B); Column A: Waters Xbridge C18 10 μm 2.1×50 mm; Column B: Phenomenex C18 10 μm 3.0×50 mm.

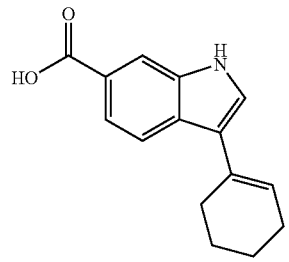

Intermediate 1

3-Cyclohexenyl-1H-indole-6-carboxylic acid. Cyclohexanone (96 mL, 0.926 mol) was added to a stirred solution of methyl indole-6-carboxylic acid (50.0 g, 0.335 mol) in methanol (920 mL) at 22° C. Methanolic sodium methoxide (416 mL of 25% w/w, 1.82 mol) was added in portions over 10 minutes. The mixture was stirred at reflux for 18 hours, cooled to room temperature, concentrated, diluted with cold water, and acidified with 36% HCl solution. The resulting precipitate was collected by filtration, washed with cold water, and dried over phosphorous pentoxide (0.1 mm) to provide the title compound as a tan colored solid (80.9 g, 97.5% yield).

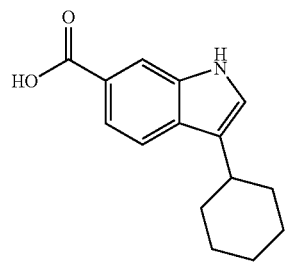

Intermediate 2

3-Cyclohexyl-1H-indole-6-carboxylic acid. 3-Cyclohexenyl-1H-indole-6-carboxylic acid (38 g) was added to a Parr bottle, followed by methanol (100 mL) and THF (100 mL). The bottle was flushed with argon and 10% palladium on carbon (1.2 g) was added. The flask was then evacuated and subsequently refilled with $H_2$ to a pressure of 55 psi, and the resultant mixture was shaken for 18 hours at RT. The catalyst was then removed by filtration through celite. Concentration of the filtrate provided the desired product as a pale purple solid (30.6 g, 79%). ESI-MS m/z 244 (MH$^+$).

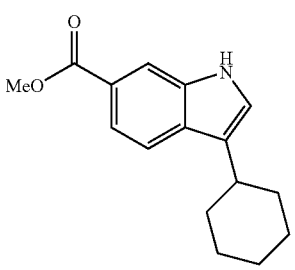

Intermediate 3

Methyl 3-cyclohexyl-1H-indole-6-carboxylate. Thionyl chloride (1 mL) was added to a stirred mixture of 3-cyclohexyl-1H-indole-6-carboxylic acid (30.4 g, 0.125 mol) in methanol (300 mL). The mixture was stirred at reflux for 18 hours, treated with decolorizing carbon, and filtered. The filtrate was concentrated to about 150 mL at which point crystallization occurred. The filtrate was cooled to room temperature and filtered. The solid washed with cold methanol followed by diethyl ether to provide the desired product as a pale purple solid (22.2 g, 69% yield). ESI-MS m/z 258 (MH$^+$); $^1$H NMR (300 MHz, CDCl$_3$) δ 1.35 (m, 4H), 1.63 (s, 1H), 1.78 (m, 3H), 2.06 (d, J=8.05 Hz, 2H), 3.90 (m, 1H), 7.08 (d, J=1.83 Hz, 1H), 7.62 (s, 1H), 7.65 (s, 1H), 7.74 (d, J=1.46 Hz, 1H), 7.77 (d, J=1.46 Hz, 1H), 8.08 (s, 1H).

Intermediate 4

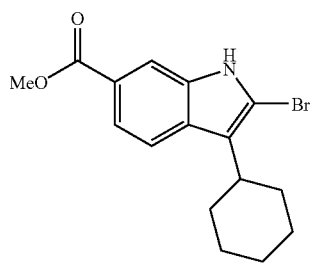

Methyl 2-bromo-3-cyclohexyl-2-1H-indole-6-carboxylate. Dry pyridinium tribromide (12.0 g, 38 mmol) was added in one portion to a stirred and cooled (ice/water bath) solution of methyl 3-cyclohexyl-1H-indole-6-carboxylate (7.71 g, 30 mmol) in a mixture of THF (80 mL) and chloroform (80 mL). The flask was removed from the cooling bath and stirring was continued for 2 hours at room temperature. The mixture was sequentially washed with 1M NaHSO$_3$ (2×50 mL) and 1N HCl (50 mL). It was then dried over anhydrous sodium sulfate, filtered, and concentrated. The concentrate was treated with hexanes and the resulting precipitate was collected by filtration to provide the desired product as an off-white solid (5.8 g, 58%). $^1$H NMR (300 MHz, CDCl$_3$) δ 1.38 (m, 3H), 1.85 (m, 7H), 2.81 (m, 1H), 7.71 (m, 2H), 8.03 (s, 1H), 8.47 (s, 1H).

The hexane mother liquor was concentrated and the residue was dissolved in hexane/ethyl acetate (5:1). The solution was passed through a pad of silica gel with the same solvents. Concentration of the eluate followed by the addition of hexane (10 mL) resulted in the precipitation of additional product which was collected by filtration to provide 2.8 g (28%) of the desired product.

Intermediate 5

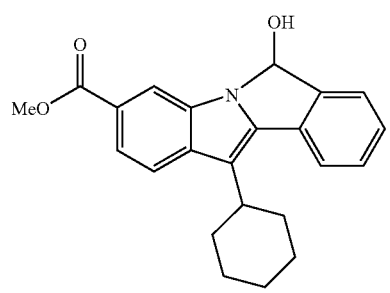

Methyl 11-cyclohexyl-6-hydroxy-6H-isoindolo[2,1-a]indole-3-carboxylate. A stirred mixture of methyl 2-bromo-3-cyclohexyl-1H-indole-6-carboxylate (10.1 g, 30 mmol), 2-formylphenylboronic acid (5.4 g, 36 mmol), LiCl (3.8 g (90 mmol) and Pd (PPh$_3$)$_4$ (1.6 g, 1.38 mmol) in 1M Na$_2$CO$_3$ (40 mL) and 1:1 EtOH-toluene (180 mL) was heated under nitrogen at 85° C. for 3 hours. The reaction mixture was then cooled to RT, and extracted with EtOAc (2×100 mL). The extracts were washed sequentially with water and brine, then dried (MgSO$_4$), filtered and conventrated in-vacuo to afforded 13.3 g of crude product. This material was triturated with DCM and hexanes to provide pure desired product (7.52 g, 70%). LC-MS: m/e 360 (M−H); 344 (M−17)$^+$. $^1$H NMR (400 MHz, CHLOROFORM-D) δ ppm 1.33-1.60 (m, 4H) 1.77-2.01 (m, 6H) 2.80 (d, J=11.83 Hz, 1H) 3.02-3.18 (m, 1H) 3.89 (s, 3H) 6.49 (d, J=11.33 Hz, 1H) 7.34 (t, J=7.55 Hz, 1H) 7.46 (t, J=7.55 Hz, 1H) 7.62 (d, J=7.30 Hz, 1H) 7.66-7.74 (m, 2H) 7.77 (d, J=7.81 Hz, 1H) 8.21 (s, 1H).

Intermediate 6

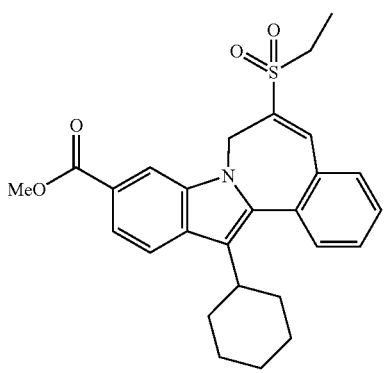

7H-Indolo[2,1-a][2]benzazepine-10-carboxylic acid, 13-cyclohexyl-6-(ethylsulfonyl)-, methyl ester. To a solution of methyl 3-cyclohexyl-2-(2-formyl-4-phenyl)-1H-indole-6-carboxylate (0.200 g, 0.553 mmol) in dioxane (2.00 mL) and BEMP (0.480 mL, 1.66 mmol) was added ethyl vinyl sulfone (0.266 g, 2.21 mmol). The resulting mixture was stirred in a sealed tube in a microwave at 150° C. for 15 min. The resulting solution was concentrated under reduced pressure. Silica gel chromatography (1:1 EtOAc:hexanes) of the concentrate afforded the title compound (213 mg, 83%) as a yellow oil. MS m/z 464 (MH$^+$). $^1$H NMR (300 MHz, CDCl$_3$) δ ppm 1.17-1.69 (m, 5H), 1.37 (t, 3H), 1.79 (m, 2H), 1.87-2.16 (m, 3H), 2.86 (m, 1H), 3.11 (q, 2H), 3.94 (s, 3H), 4.14 (broad m, 1H), 5.72 (broad m, 1H), 7.38 (s, 1H), 7.46 (m, 2H), 7.53 (dd, J=7.6, 8.4 Hz,1H), 7.61 (d, J=7.6 Hz, 1H), 7.74 (d, J=8.4 Hz, 1H), 7.87 (d, J=8.4 Hz, 1H), 8.29 (s, 1H).

Intermediate 7

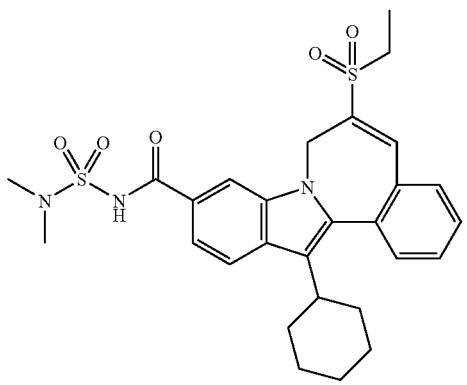

7H-Indolo[2,1-a][2]benzazepine-10-carboxamide, 13-cyclohexyl-N-[(dimethylamino)sulfonyl]-6-(ethylsulfonyl)-To a solution of 7H-Indolo[2,1-a][2]benzazepine-10-carboxylic acid,13-cyclohexyl-6-(ethylsulfonyl)-, methyl ester (80 mg, 0.17 mmol) in 1:1 MeOH/THF (2.0 mL) was added 1M NaOH (2.0 mL). The resulting mixture was stirred at 22° C. for 16 hr. 1M HCl (15 mL) was added and the aqueous layer was extracted with CHCl₃ (2×15 mL). The organic phase was dried over Na₂SO₄, filtered, and concentrated under reduced pressure to afford a white solid. This solid was dissolved in CH₂Cl₂ (1.5 mL) and 2M oxalyl chloride (1.5 mL) in CH₂Cl₂ was added. This solution was stirred at 22° C. for 2 hr and concentrated under reduced pressure. The resulting yellow oil was redissolved in CH₂Cl₂ (1.5 mL); BEMP (94 mg, 0.34 mmol) and dimethylsulfamide (107 mg, 0.86 mmol) were added. The resulting mixture was allowed to stir at 22° C. for 6 hr 1M HCl (15 mL) was added and the aqueous layer was extracted with CHCl₃ (2×30 mL). The organic phase was concentrated under reduced pressure. This oil was purified by reverse-phase prep HPLC to afford the title compound (67 mg, 69%) as a yellow paste. MS m/z 556 (MH⁺). ¹H NMR (300 MHz, CDCl₃) δ ppm 1.18-1.70 (m, 5H), 1.35 (t, 3H), 1.77 (m, 2H), 1.87-2.16 (m, 3H), 2.88 (m, 1H), 3.08 (s, 6H), 3.15 (q, 2H), 4.18 (broad m, 1H), 5.67 (broad m, 1H), 7.38 (s, 1H), 7.47 (m, 2H), 7.51 (dd, J=7.6, 8.4 Hz,1H), 7.61 (d, J=7.6 Hz, 1H), 7.75 (d, J=8.4 Hz, 1H), 7.87 (d, J=8.4 Hz, 1H), 8.31 (s, 1H), 8.54 (broad s, 1H).

Intermediate 8

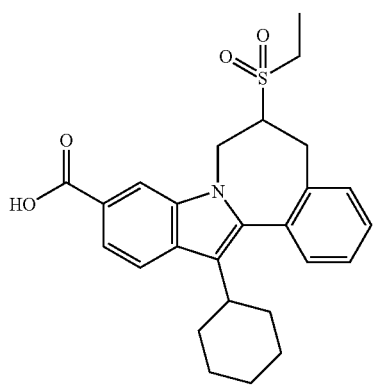

5H-Indolo[2,1-a][2]benzazepine-10-carboxylic acid,13-cyclohexyl-6-(ethylsulfonyl)-6,7-dihydro-. To a mixture of 7H-Indolo[2,1-a][2]benzazepine-10-carboxylic acid,13-cyclohexyl-6-(ethylsulfonyl)-, methyl ester (80 mg, 0.18 mmol) and 20% Pd(OH)₂ (30 mg) in MeOH (3.0 mL) was applied 1 atm of H₂ using a balloon. The resulting mixture was allowed to stir at 22° C. for 18 hr, filtered through celite and concentrated under reduced pressure. The resulting white solid was dissolved in 1:1 MeOH/THF (4.0 mL) and 1M NaOH (4.0 mL) was added. The resulting mixture was stirred at 22° C. for 16 hr. 1M HCl (15 mL) was added and the aqueous layer was extracted with CHCl₃ (2×15 mL). The organic phase was dried over Na₂SO₄, filtered, and concentrated under reduced pressure to afford a beige solid. This was purified by reverse-phase prep HPLC to afford the title compound (60 mg, 75%) as a white solid. MS m/z 452 (MH⁺). Two rotomers present in NMR. ¹H NMR (300 MHz, CDCl₃) δ ppm 1.09-1.51 (m, 6H), 1.62-1.76 (m, 3H), 1.86-2.08 (m, 4H), 2.82-3.13 (m, 4H), 3.19-3.39 (m, 1H), 3.54-3.67 (m, 0.6H), 3.72-4.12 (m, 1.4H), 4.70 (m, 0.4H), 5.11 (d, 16 Hz, 0.6H), 7.36-7.49 (m, 5H), 7.89 (m, 1H), 8.01 (m, 1H).

Intermediate 9

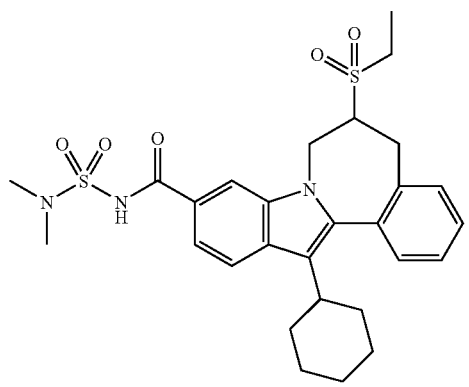

5H-Indolo[2,1-a][2]benzazepine-10-carboxamide, 13-cyclohexyl-N-[(dimethylamino)sulfonyl]-6-(ethylsulfonyl)-6,7-dihydro-. To a solution of 5H-indolo[2,1-a][2]benzazepine-10-carboxylic acid, 13-cyclohexyl-6-(ethylsulfonyl)-6,7-dihydro-(60 mg, 0.13 mmol) in CH₂Cl₂ (1.0 mL) was added 2M oxalyl chloride (0.40 mL) in CH₂Cl₂. This solution was stirred at 22° C. for 2 hr and concentrated under reduced pressure. The resulting yellow oil was redissolved in CH₂Cl₂ (1.0 mL); BEMP (0.15 mL, 0.53 mmol) and dimethylsulfamide (99 mg, 0.80 mmol) were added. The resulting mixture was allowed to stir at 22° C. for 6 hr. 1M HCl (15 mL) was added and the aqueous layer was extracted with CHCl₃ (2×30 mL). The organic phase was concentrated under reduced pressure. This oil was purified by reverse-phase prep HPLC to afford the title compound (52 mg, 71%) as a yellow paste. MS m/z 558 (MH⁺). Two rotomers present in NMR. ¹H NMR (300 MHz, CDCl₃) δ ppm 1.10-1.51 (m, 6H), 1.62 (m, 1H), 1.75 (m, 2H), 1.86-2.08 (m, 4H), 2.84-3.15 (m, 4H), 3.03 (d, 6H), 3.19-3.39 (m, 1H), 3.54-3.67 (m, 0.6H), 3.72-3.98 (m, 1H), 4.10 (m, 0.4H), 4.70 (m, 0.4H), 5.11 (d, 16 Hz, 0.6H), 7.36-7.49 (m, 5H), 7.89 (m, 1H), 8.01 (m, 1H), 8.84 (m, 1H).

Intermediate 10

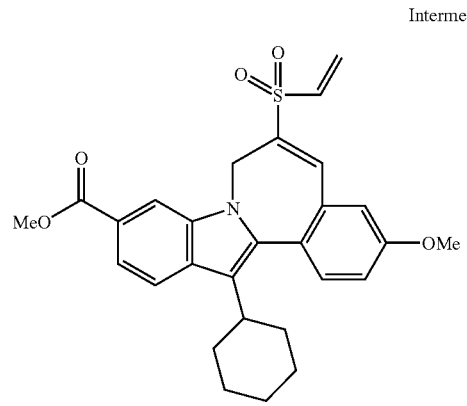

7H-Indolo[2,1-a][2]benzazepine-10-carboxylic acid,13-cyclohexyl-6-(ethenylsulfonyl)-3-methoxy-, methyl ester. To a solution of methyl 3-cyclohexyl-2-(2-formyl-4-methoxyphenyl)-1H-indole-6-carboxylate (0.600 g, 1.53 mmol) in dioxane (5.00 mL) and BEMP (0.890 mL, 3.10 mmol) was added divinyl sulfone (0.615 mL, 6.13 mmol). The resulting mixture was stirred in a sealed tube in a microwave at 160° C. for 1 hr. The resulting solution was concentrated under reduced pressure. Silica gel chromatography (1:1 EtOAc: hexanes) of the concentrate afforded the title compound (482 mg, 64%) as a brownish oil. MS m/z 492 (MH+), ret time 2.91 min, column B, 4 minute gradient, flow rate 4 mL/min.

Intermediate 11

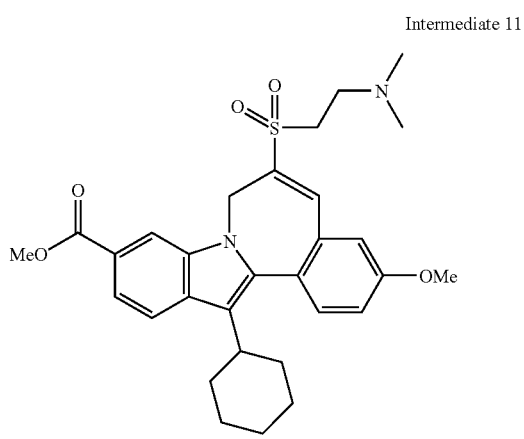

7H-Indolo[2,1-a][2]benzazepine-10-carboxylic acid, 13-cyclohexyl-6-[[2-(dimethylamino)ethyl]sulfonyl]-3-methoxy-, methyl ester. To a solution of 7H-Indolo[2,1-a][2]benzazepine-10-carboxylic acid, 13-cyclohexyl-6-(ethenylsulfonyl)-3-methoxy-, methyl ester (30 mg, 0.059 mmol) in 2M methylamine in THF (0.59 mL) was added BEMP (0.034 mL, 0.12 mmol). The resulting solution was stirred at 150° C. in a sealed tube in a microwave for 1 hr. The resulting mixture was concentrated under reduced pressure to afford a brown oil which was purified by reverse-phase prep HPLC to afford the title compound (22 mg, 69%) as a yellow paste. MS m/z 537 (MH+), ret time 2.68 min, column B, 4 minute gradient, flow rate 4 mL/min.

Intermediate 12

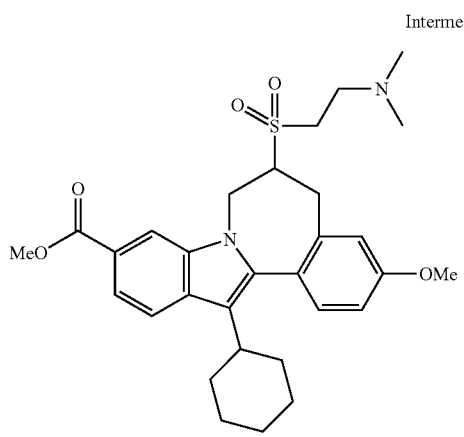

5H-Indolo[2,1-a][2]benzazepine-10-carboxylic acid, 13-cyclohexyl-6-[[2-(dimethylamino)ethyl]sulfonyl]-6,7-dihydro-3-methoxy-, methyl ester. To a mixture of 7H-Indolo [2,1-a][2]benzazepine-10-carboxylic acid, 13-cyclohexyl-6-[[2-(dimethylamino)ethyl]sulfonyl]-3-methoxy-, methyl ester (22 mg, 0.041 mmol) and 20% Pd(OH)$_2$ (20 mg) in 1:1 iPrOH/ethyl acetate (4.0 mL) was applied 1 atm of H$_2$ using a balloon. The resulting mixture was allowed to stir at 22° C. for 18 hr, filtered through celite and concentrated under reduced pressure to afford the title compound (22 mg, 100%) as a yellow paste. MS m/z 539 (MH+). Two rotomers present in NMR. $^1$H NMR (300 MHz, CDCl$_3$) δ ppm 1.10-1.51 (m, 3H), 1.62-1.76 (m, 3H), 1.88-2.08 (m, 4H), 2.45 (d, 6H), 2.76-3.18 (m, 6H), 3.19-3.40 (m, 1H), 3.53-3.67 (m, 0.6H), 3.72-4.11 (m, 1.4H), 3.88 (d, 3H), 3.94 (d, 3H), 4.72 (m, 0.4H), 5.10 (d, 16 Hz, 0.6H), 7.02-709 (m, 2H), 7.38-7.51 (m, 2H), 7.90 (m, 1H), 8.06 (m, 1H).

Intermediate 13

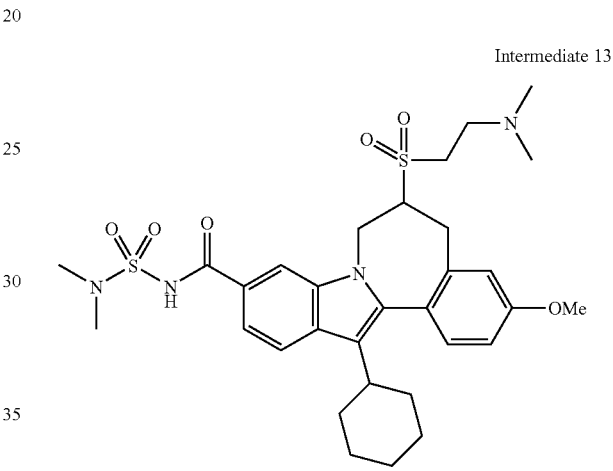

5H-Indolo[2,1-a][2]benzazepine-10-carboxamide, 13-cyclohexyl-6-[[2-(dimethylamino)ethyl]sulfonyl]-N-[(dimethylamino)sulfonyl]-6,7-dihydro-3-methoxy-. To a solution of 5H-Indolo[2,1-a][2]benzazepine-10-carboxylic acid, 13-cyclohexyl-6-[[2-(dimethylamino)ethyl]sulfonyl]-6,7-dihydro-3-methoxy-, methyl ester (22 mg, 0.041 mmol) in THF (1.5 mL) was added CDI (20 mg, 0.12 mmol) and the resulting solution was heated 60° C. for 1 hr. Dimethylsulfamide (64 mg, 0.52 mmol) and DBU (0.016 mL, 0.10 mmol) were added. The resulting mixture was allowed to stir at 60° C. for 1 hr and 22° C. for 16 hr. 1M HCl (15 mL) was added and the aqueous layer was extracted with CHCl$_3$ (2×20 mL). The organic phase was concentrated under reduced pressure. This oil was purified by reverse-phase prep HPLC to afford the title compound (17 mg, 67%) as a yellow solid. MS m/z 631 (MH+). Two rotomers present in NMR. $^1$H NMR (300 MHz, CDCl$_3$) δ ppm 1.12-1.51 (m, 3H), 1.62-1.74 (m, 3H), 1.87-2.06 (m, 4H), 2.45 (d, 6H), 2.76-3.16 (m, 6H), 3.02 (d, 6H), 3.19-3.39 (m, 1H), 3.53-3.67 (m, 0.6H), 3.72-4.12 (m, 1.4H), 3.85 (d, 3H), 4.70 (m, 0.4H), 5.11 (d, 16 Hz, 0.6H), 7.03-7.10 (m, 2H), 7.38-7.51 (m, 2H), 7.91 (m, 1H), 8.07 (m, 1H), 8.78 (broad s, 1H).

The following compounds were synthesized by an analogous method as described above for 5H-indolo[2,1-a][2]benzazepine-10-carboxamide, 13-cyclohexyl-6-[[2-(dimethylamino)ethyl]sulfonyl]-N-[(dimethylamino)sulfonyl]-6,7-dihydro-3-methoxy-.

Intermediate 14

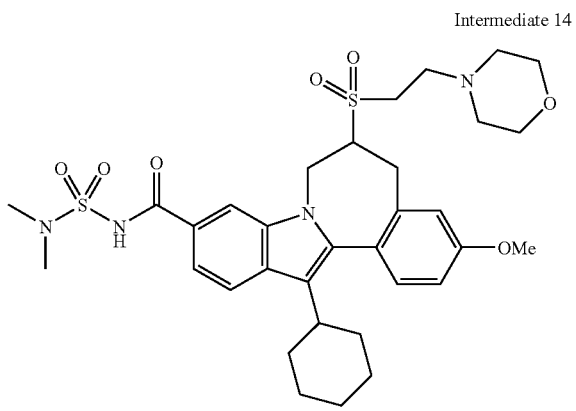

5H-Indolo[2,1-a][2]benzazepine-10-carboxamide, 13-cyclohexyl-N-[(dimethylamino)sulfonyl]-6,7-dihydro-3-methoxy-6-[[2-(1-morpholinyl)ethyl]sulfonyl]-. MS m/z 673 (MH+). Two rotamers present in NMR. $^1$H NMR (300 MHz, CDCl$_3$) δ ppm 1.12-1.51 (m, 3H), 1.64-1.74 (m, 3H), 1.88-2.05 (m, 4H), 2.61-3.18 (m, 10H), 3.03 (d, 6H), 3.19-3.40 (m, 3H), 3.54-3.68 (m, 2.6H), 3.72-4.12 (m, 1.4H), 3.87 (d, 3H), 4.70 (m, 0.4H), 5.12 (d, 16 Hz, 0.6H), 7.02-7.09 (m, 2H), 7.38-7.50 (m, 2H), 7.89 (m, 1H), 8.04 (m, 1H), 8.68 (broad d, 1H).

Intermediate 15

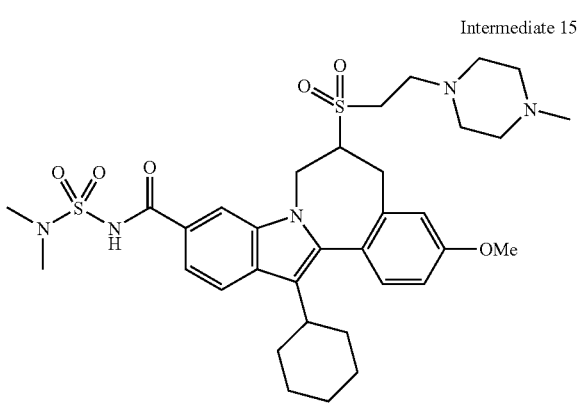

5H-Indolo[2,1-a][2]benzazepine-10-carboxamide, 13-cyclohexyl-N-[(dimethylamino)sulfonyl]-6,7-dihydro-3-methoxy-6-[[2-(4-methyl-1-piperazinyl)ethyl]sulfonyl]-. MS m/z 686 (MH+). Two rotamers present in NMR. $^1$H NMR (300 MHz, CDCl$_3$) δ ppm 1.09-1.48 (m, 3H), 1.61-1.72 (m, 3H), 1.85-2.07 (m, 4H), 2.42 (d, 3H), 2.48-3.18 (m, 12H), 3.02 (d, 6H), 3.22-3.39 (m, 3H), 3.54-3.69 (m, 0.6H), 3.71-4.11 (m, 1.4H), 3.84 (d, 3H), 4.66 (m, 0.4H), 5.07 (d, 16 Hz, 0.6H), 7.03-7.11 (m, 2H), 7.38-7.49 (m, 2H), 7.91 (m, 1H), 8.05 (m, 1H), 8.59 (broad d, 1H).

Intermediate 16

4-(Vinylsulfonyl)morpholine. To a 0° C. solution of 2,3,4,5,6-pentafluorophenyl-1-ethylenesulfonate (2.00 g, 7.29 mmol, commercially available from Bionet Research Ltd.) in dioxane (15.0 mL) and BEMP (2.11 mL, 7.29 mmol) was added morpholine (0.636 mL, 7.29 mmol). This was stirred at 0° C. for 1 hr; 22° C. for 1 hr and the resulting mixture was filtered. The filtrate was concentrated under reduced pressure to yield the crude product (1.28 g, 99%) as a yellow oil. MS m/z 178 (MH+).

Intermediate 17

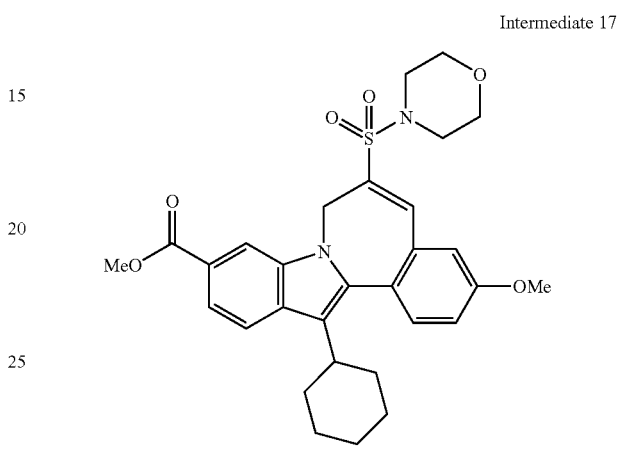

7H-Indolo[2,1-a][2]benzazepine-10-carboxylic acid, 13-cyclohexyl-3-methoxy-6-(4-morpholinylsulfonyl)-, methyl ester. To a solution of methyl 3-cyclohexyl-2-(2-formyl-4-methoxyphenyl)-1H-indole-6-carboxylate (300 mg, 0.766 mmol) in dioxane (2.50 mL) and BEMP (0.443 mL, 1.53 mmol) was added 4-(vinylsulfonyl)morpholine (0.270 g, 1.53 mmol). The resulting mixture was stirred in a sealed tube in a microwave at 160° C. for 60 min and then concentrated under reduced pressure. Silica gel chromatography (1:1 EtOAc:hexanes) of the concentrate afforded the title compound (211 mg, 50%) as a yellow oil. MS 551 m/z (MH+). $^1$H NMR (300 MHz, CDCl$_3$) δ ppm 1.16-1.62 (m, 4H), 1.79 (m, 1H), 1.90-2.11 (m, 5H), 2.81 (m, 3H), 3.06 (m, 2H), 3.24 (m, 2H), 3.42 (m, 2H), 3.86 (s, 3H), 3.92 (s, 3H), 4.30 (broad d, 1H), 5.46 (broad d, 1H), 7.01 (d, 1H), 7.12 (m, 1H), 7.38 (m, 1H), 7.50 (m, 1H), 7.65 (s, 1H), 7.89 (m, 1H), 8.10 (s, 1H).

Intermediate 18

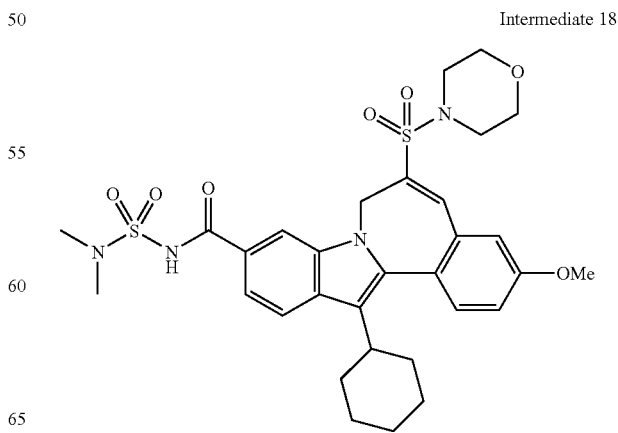

7H-Indolo[2,1-a][2]benzazepine-10-carboxamide, 13-cyclohexyl-N-[(dimethylamino)sulfonyl]-3-methoxy-6-(4-morpholinylsulfonyl)-. To a solution of 7H-Indolo[2,1-a][2]benzazepine-10-carboxylic acid, 13-cyclohexyl-3-methoxy-6-(4-morpholinylsulfonyl)-, methyl ester (60 mg, 0.11 mmol) in 1:1 MeOH/THF (2.0 mL) was added 1M NaOH (2.0 mL). The resulting mixture was stirred at 22° C. for 16 hr. 1M HCl (15 mL) was added and the aqueous layer was extracted with CHCl$_3$ (2×15 mL). The organic phase was dried over Na$_2$SO$_4$, filtered, and concentrated under reduced pressure to afford a white solid. This solid was dissolved in CH$_2$Cl$_2$ (1.0 mL) and 2M oxalyl chloride (1.0 mL) in CH$_2$Cl$_2$ was added. This solution was stirred at 22° C. for 2 hr and concentrated under reduced pressure. The resulting yellow oil was redissolved in CH$_2$Cl$_2$ (1.0 mL); BEMP (60 mg, 0.22 mmol) and dimethylsulfamide (68 mg, 0.55 mmol) were added. The resulting mixture was allowed to stir at 22° C. for 6 hr. 1M HCl (15 mL) was added and the aqueous layer was extracted with CHCl$_3$ (2×30 mL). The organic phase was concentrated under reduced pressure. This oil was purified by reverse-phase prep HPLC to afford the title compound (50 mg, 71%) as a yellow paste. MS 643 m/z (MH$^+$). $^1$H NMR (300 MHz, CDCl$_3$) δ ppm 1.15-1.60 (m, 4H), 1.80 (m, 1H), 1.91-2.12 (m, 5H), 2.81 (m, 3H), 3.08 (broad s, 8H), 3.22 (m, 2H), 3.41 (m, 2H), 3.92 (s, 3H), 4.4 (broad d, 1H), 5.36 (broad d, 1H), 7.02 (d, 1H), 7.15 (m, 1H), 7.40 (m, 1H), 7.51 (m, 1H), 7.68 (s, 1H), 7.90 (m, 1H), 8.11 (s, 1H), 8.58 (s, 1H).

Intermediate 19

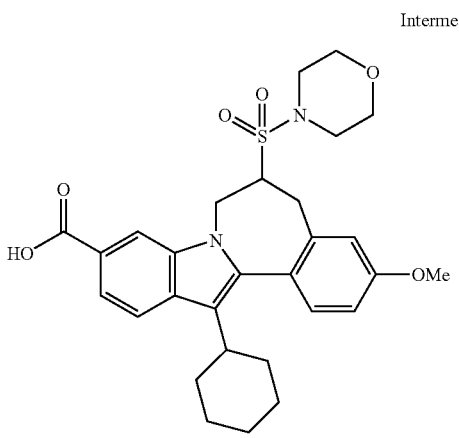

5H-Indolo[2,1-a][2]benzazepine-10-carboxylic acid, 13-cyclohexyl-6,7-dihydro-3-methoxy-6-(4-morpholinylsulfonyl)-. To a mixture of 7H-indolo[2,1-a][2]benzazepine-10-carboxylic acid, 13-cyclohexyl-3-methoxy-6-(4-morpholinylsulfonyl)-, methyl ester (60 mg, 0.11 mmol) and 20% Pd(OH)$_2$ (30 mg) in MeOH (2.0 mL) was applied 1 atm of H$_2$ using a balloon. The resulting mixture was allowed to stir at 22° C. for 18 hr, filtered through celite and concentrated under reduced pressure. The resulting white solid was dissolved in 1:1 MeOH/THF (4.0 mL) and 1M NaOH (4.0 mL) was added. The resulting mixture was stirred at 22° C. for 16 hr. 1M HCl (15 mL) was added and the aqueous layer was extracted with CHCl$_3$ (2×15 mL). The organic phase was dried over Na$_2$SO$_4$, filtered, and concentrated under reduced pressure to afford a beige solid. This was purified by reverse-phase prep HPLC to afford the title compound (56 mg, 95%) as a white solid. MS m/z 539 (MH$^+$). Two rotomers present in NMR. $^1$H NMR (300 MHz, CDCl$_3$) δ ppm 1.26-1.49 (m, 3H), 1.65 (m, 1H), 1.80 (m, 2H), 1.88-2.11 (m, 4H), 2.87 (m, 1H), 2.99-3.16 (m, 3H), 3.36 (m, 2.6H), 3.42 (m, 1.4H), 3.58-3.81 (m, 4H), 3.92 (d, 3H), 3.96 (m, 0.65H), 4.07 (m, 0.35H), 4.72 (m, 0.35H), 4.97 (d, J=15 Hz, 0.65H), 6.92-6.97 (m, 2H), 7.33 (m, 1H), 7.50 (m, 1H), 7.65-7.88 (m, 1H), 8.10 (m, 1H).

Intermediate 20

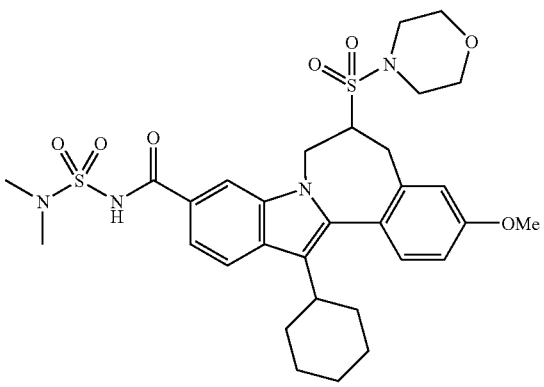

5H-Indolo[2,1-a][2]benzazepine-10-carboxamide, 13-cyclohexyl-N-[(dimethylamino)sulfonyl]-6,7-dihydro-3-methoxy-6-(4-morpholinylsulfonyl)-. To a solution of 5H-indolo[2,1-a][2]benzazepine-10-carboxylic acid, 13-cyclohexyl-6,7-dihydro-3-methoxy-6-(4-morpholinylsulfonyl)-(45 mg, 0.084 mmol) in CH$_2$Cl$_2$ (1.0 mL) was added 2M oxalyl chloride (0.20 mL) in CH$_2$Cl$_2$. This solution was stirred at 22° C. for 2 hr and concentrated under reduced pressure. The resulting yellow oil was redissolved in CH$_2$Cl$_2$ (1.0 mL); BEMP (0.10 mL, 0.33 mmol) and dimethylsulfamide (42 mg, 0.33 mmol) were added. The resulting mixture was allowed to stir at 22° C. for 6 hr. 1M HCl (15 mL) was added and the aqueous layer was extracted with CHCl$_3$ (2×20 mL). The organic phase was concentrated under reduced pressure. This oil was purified by reverse-phase prep HPLC to afford the title compound (34 mg, 64%) as a yellow paste. MS m/z 645 (MH$^+$). Two rotomers present in NMR. $^1$H NMR (300 MHz, CDCl$_3$) δ ppm 1.26 (m, 1H), 1.32-1.49 (m, 2H), 1.64 (m, 1H), 1.78 (m, 2H), 1.88-2.10 (m, 4H), 2.89 (m, 1H), 2.97-3.15 (m, 9H), 3.36 (m, 2.6H), 3.45 (m, 1.4H), 3.66-3.81 (m, 4H), 3.92 (d, 3H), 3.96 (m, 0.65H), 4.07 (m, 0.35H), 4.72 (m, 0.35H), 4.97 (d, J=15 Hz, 0.65H), 6.92 (m, 0.65H), 6.97 (m, 1.35H), 7.33-7.47 (m, 2H), 7.87 (m, 1H), 7.99 (m, 1H), 8.55 (broad s, 1H).

Intermediate 21

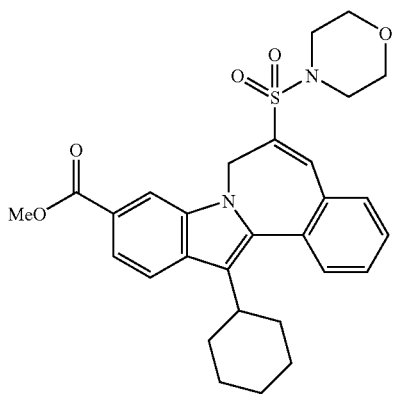

7H-Indolo[2,1-a][2]benzazepine-10-carboxylic acid, 13-cyclohexyl-6-(4-morpholinylsulfonyl)-, methyl ester. To a solution of 3-cyclohexyl-2-(2-formyl-4-phenyl)-1H-indole-6-carboxylate (300 mg, 0.830 mmol) in dioxane (2.50 mL) and BEMP (0.720 mL, 2.49 mmol) was added 4-(vinylsulfonyl)morpholine (0.588 g, 3.32 mmol). The resulting mixture was stirred in a sealed tube in a microwave at 150° C. for 15 min and then concentrated under reduced pressure. Silica gel chromatography (1:1 EtOAc:hexanes) of the concentrate afforded the title compound (151 mg, 35%) as a yellow oil. MS m/z 521 (MH+). $^1$H NMR (300 MHz, CDCl$_3$) δ ppm 1.17-1.69 (m, 5H), 1.79 (m, 2H), 1.87-2.16 (m, 3H), 2.86 (m, 1H), 3.92 (s, 3H), 4.14 (broad m, 1H), 5.72 (broad m, 1H), 7.38 (s, 1H), 7.46 (m, 2H), 7.53 (dd, J=7.6, 8.4 Hz, 1H), 7.61 (d, J=7.6 Hz, 1H), 7.74 (d, J=8.4 Hz, 1H), 7.87 (d, J=8.4 Hz, 1H), 8.29 (s, 1H).

Intermediate 22

7H-Indolo[2,1-a][2]benzazepine-10-carboxamide, 13-cyclohexyl-N-[(dimethylamino)sulfonyl]-6-(4-morpholinylsulfonyl)-. To a solution of 7H-Indolo[2,1-a][2]benzazepine-10-carboxylic acid, 13-cyclohexyl-6-(4-morpholinylsulfonyl)-, methyl ester (60 mg, 0.12 mmol) in 1:1 MeOH/THF (2.0 mL) was added 1M NaOH (2.0 mL). The resulting mixture was stirred at 22° C. for 16 hr. 1M HCl (15 mL) was added and the aqueous layer was extracted with CHCl$_3$ (2×15 mL). The organic phase was dried over Na$_2$SO$_4$, filtered, and concentrated under reduced pressure to afford a white solid. This solid was dissolved in CH$_2$Cl$_2$ (1.0 mL) and 2M oxalyl chloride (0.24 mL) in CH$_2$Cl$_2$ was added. This solution was stirred at 22° C. for 2 hr and concentrated under reduced pressure. The resulting yellow oil was redissolved in CH$_2$Cl$_2$ (1.0 mL); BEMP (0.14, 0.47 mmol) and dimethylsulfamide (59 mg, 0.47 mmol) were added. The resulting mixture was allowed to stir at 22° C. for 6 hr. 1M HCl (15 mL) was added and the aqueous layer was extracted with CHCl$_3$ (2×30 mL). The organic phase was concentrated under reduced pressure. This oil was purified by reverse-phase prep HPLC to afford the title compound (50 mg, 68%) as a yellow paste. MS m/z 613 (MH+). $^1$H NMR (300 MHz, CDCl$_3$) δ ppm 1.18-1.70 (m, 5H), 1.77 (m, 2H), 1.87-2.16 (m, 3H), 2.88 (m, 1H), 3.08 (s, 6H), 3.93 (s, 3H), 4.18 (broad m, 1H), 5.67 (broad m, 1H), 7.38 (s, 1H), 7.47 (m, 2H), 7.51 (dd, J=7.6, 8.4 Hz, 1H), 7.61 (d, J=7.6 Hz, 1H), 7.75 (d, J=8.4 Hz, 1H), 7.87 (d, J=8.4 Hz, 1H), 8.31 (s, 1H).

Intermediate 23

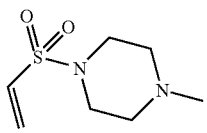

1-Methyl-4-(vinylsulfonyl)piperazine. To a 0° C. solution of 2,3,4,5,6-pentafluorophenyl-1-ethylenesulfonate (2.80 g, 10.2 mmol, commercially available from Bionet Research Ltd.) in dioxane (20.0 mL) and BEMP (2.95 mL, 10.2 mmol) was added 1-methylpiperazine (1.02 g, 10.2 mmol). This was stirred at 0° C. for 1 hr; 22° C. for 1 hr and the resulting mixture was filtered. The filtrate was concentrated under reduced pressure to yield the crude product (1.93 g, 99%) as a yellow oil. MS m/z 191 (MH+).

Intermediate 24

7H-Indolo[2,1-a][2]benzazepine-10-carboxylic acid, 13-cyclohexyl-3-methoxy-6-[(4-methyl-1-piperazinyl)sulfonyl]-, methyl ester. To a solution of methyl 3-cyclohexyl-2-(2-formyl-4-methoxyphenyl)-1H-indole-6-carboxylate (1.00 g, 2.56 mmol) in dioxane (8.5 mL) and BEMP (2.22 mL, 7.68 mmol) was added 1-methyl-4-(vinylsulfonyl)piperazine (1.94 g, 10.2 mmol). The resulting mixture was stirred in a sealed tube in a microwave at 160° C. for 60 min and then concentrated under reduced pressure. Silica gel chromatography (1:1 EtOAc:hexanes) of the concentrate afforded the title compound (480 mg, 34%) as a yellow solid. MS m/z 551 (MH+). $^1$H NMR (300 MHz, CDCl$_3$) δ ppm 1.16-1.62 (m, 4H), 1.79 (m, 1H), 1.90-2.11 (m, 5H), 2.53 (s, 3H), 2.81 (m, 1H), 2.87-3.16 (m, 5H), 3.36 (m, 1H), 3.58 (m, 1H), 3.70 (m, 1H), 3.86 (s, 3H), 3.92 (s, 3H), 4.30 (broad d, 1H), 5.46 (broad d, 1H), 7.01 (d, 1H), 7.12 (m, 1H), 7.52 (m, 2H), 7.71 (s, 1H), 7.90 (m, 1H), 8.10 (s, 1H).

Intermediate 25

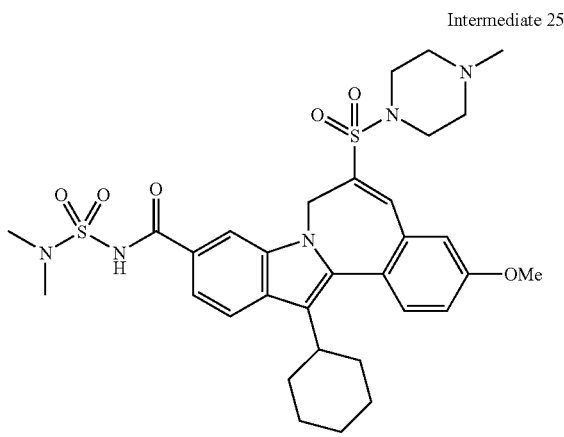

7H-Indolo[2,1-a][2]benzazepine-10-carboxamide, 13-cyclohexyl-N-[(dimethylamino)sulfonyl]-3-methoxy-6-[(4-methyl-1-piperazinyl)sulfonyl]-. To a solution of 7H-Indolo[2,1-a][2]benzazepine-10-carboxylic acid, 13-cyclohexyl-3-methoxy-6-[(4-methyl-1-piperazinyl)sulfonyl]-, methyl ester (60 mg, 0.11 mmol) in 1:1 MeOH/THF (2.0 mL) was added 1M NaOH (2.0 mL). The resulting mixture was stirred at 22° C. for 16 hr. 1M HCl (15 mL) was added and the aqueous layer was extracted with $CHCl_3$ (2×15 mL). The organic phase was dried over $Na_2SO_4$, filtered, and concentrated under reduced pressure to afford a white solid. This solid was dissolved in $CH_2Cl_2$ (110 mL) and 2M oxalyl chloride (1.0 mL) in $CH_2Cl_2$ was added. This solution was stirred at 22° C. for 2 hr and concentrated under reduced pressure. The resulting yellow oil was redissolved in $CH_2Cl_2$ (110 mL); BEMP (60 mg, 0.22 mmol) and dimethylsulfamide (68 mg, 0.55 mmol) were added. The resulting mixture was allowed to stir at 22° C. for 6 hr. 1M HCl (15 mL) was added and the aqueous layer was extracted with $CHCl_3$ (2×30 mL). The organic phase was concentrated under reduced pressure. This oil was purified by reverse-phase prep HPLC to afford the title compound (48 mg, 68%) as a yellow paste. MS m/z 643 (MH$^+$). $^1$H NMR (300 MHz, CDCl$_3$) δ ppm 1.13-1.52 (m, 4H), 1.79 (m, 1H), 1.90-2.11 (m, 5H), 2.56 (s, 3H), 2.79 (m, 1H), 2.87-3.16 (m, 5H), 3.05 (s, 6H), 3.36 (m, 1H), 3.58 (m, 1H), 3.70 (m, 1H), 3.92 (s, 3H), 4.41 (broad d, 1H), 5.28 (broad d, 1H), 7.01 (d, 1H), 7.12 (m, 1H), 7.52 (m, 2H), 7.65 (s, 1H), 7.89 (m, 1H), 8.10 (s, 1H), 9.60 (s, 1H).

Intermediate 26

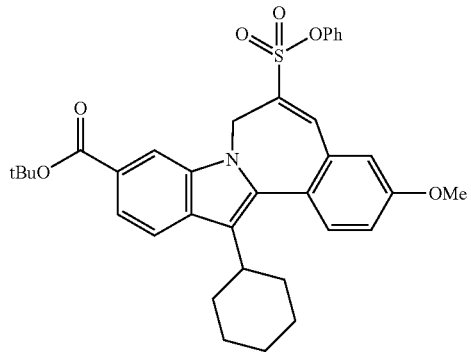

7H-Indolo[2,1-a][2]benzazepine-10-carboxylic acid, 13-cyclohexyl-3-methoxy-6-(phenoxysulfonyl)-,1,1-dimethylethyl ester. To a solution of tbutyl 3-cyclohexyl-2-(2-formyl-4-methoxyphenyl)-1H-indole-6-carboxylate (4.40 g, 11.2 mmol) in dioxane (30.0 mL) and BEMP (4.88 mL, 16.9 mmol) was added phenyl vinylsulfonate (4.14 g, 22.5 mmol). The resulting mixture was stirred at 22° C. for 1 hr and then at 110° C. in a sealed tube in a microwave for 15 min. The resulting mixture was concentrated under reduced pressure. Silica gel chromatography (1:1 EtOAc:hexanes) of the concentrate afforded the title compound (3.49 g, 52%) as a yellow oil. MS m/z 600 (MH$^+$), ret time 3.11 min, column B, 4 minute gradient, flow rate 4 mL/min.

EXAMPLE 1

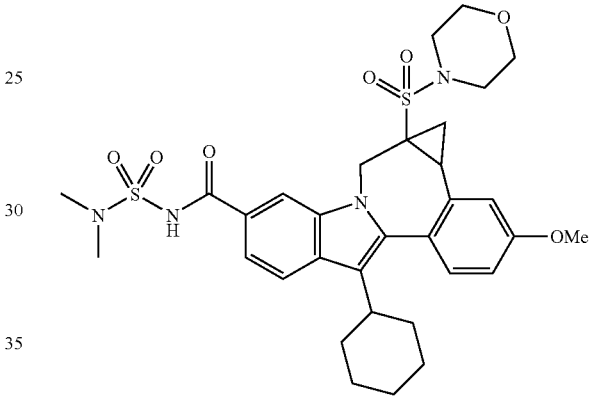

Cycloprop[d]indolo[2,1-a][2]benzazepine-5-carboxamide, 8-cyclohexyl-N-[(dimethylamino)sulfonyl]-1,1a, 2,12b-tetrahydro-11-methoxy-1a-(4-morpholinylsulfonyl)-. To a solution of trimethylsulfoxonium iodide (51 mg, 0.23 mmol) in DMSO (1.0 mL) was added 90% NaH (6.2 mg, 0.23 mmol). This mixture was stirred at 22° C. for 15 min followed by addition of 7H-Indolo[2,1-a][2]benzazepine-10-carboxamide, 13-cyclohexyl-N-[(dimethylamino)sulfonyl]-3-methoxy-6-(4-morpholinylsulfonyl)-(50 mg, 0.078 mmol) in DMSO (1.0 mL). The resulting solution was stirred at 60° C. for 3 hr; 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compound (36 mg, 70%) as a yellow paste. MS m/z 657 (MH$^+$). Two rotomers present in NMR. $^1$H NMR (300 MHz, CDCl$_3$) δ ppm 0.39 (t, 0.5H), 1.20-1.49 (m, 4.5H), 1.58 (m, 1H), 1.75-2.18 (m, 5H), 2.60 (m, 1H), 2.70 (m, 1H), 2.75-3.07 (m, 5H), 3.08 (d, 6H), 3.39 (m, 2H), 3.72 (d, 15 Hz, 0.5H), 3.82 (m, 2H), 3.90 (d, 3H), 4.19 (d, 15 Hz, 0.5H), 5.09 (d, 15 Hz, 0.5H), 5.43 (d, 15 Hz, 0.5H), 6.96 (m, 1H), 7.06 (d, 0.5H), 7.12, (d, 0.5H), 7.42 (m, 1H), 7.92 (m, 1H), 8.05 (d, 1H), 8.10 (d, 1H), 8.70 (d, 1H).

EXAMPLE 2

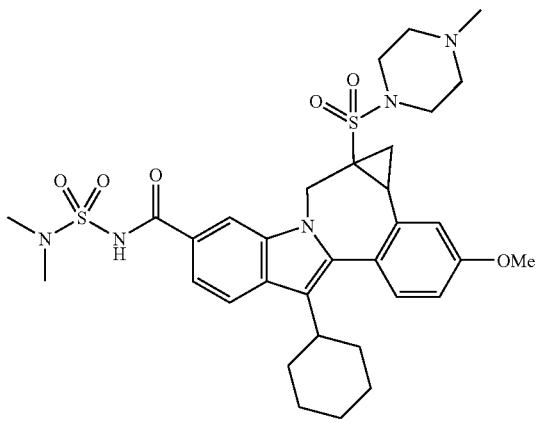

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[(4-methyl-1-piperazinyl)sulfonyl]-. To a solution of trimethylsulfoxonium iodide (57 mg, 0.26 mmol) in DMSO (1.0 mL) was added 90% NaH (6.8 mg, 0.26 mmol). This mixture was stirred at 22° C. for 15 min followed by addition of 7H-Indolo[2,1-a][2]benzazepine-10-carboxamide, 13-cyclohexyl-N-[(dimethylamino)sulfonyl]-3-methoxy-6-[(4-methyl-1-piperazinyl)sulfonyl]-(55 mg, 0.086 mmol) in DMSO (1.0 mL). The resulting solution was stirred at 60° C. for 3 hr; 1M HCl (15 mL) was added and the aqueous layer was extracted with CHCl₃ (2×30 mL). The organic phase was dried over Na₂SO₄, filtered, and concentrated under reduced pressure. This oil was purified by reverse-phase prep HPLC to afford the title compound (32 mg, 57%) as a yellow solid. MS m/z 657 (MH⁺). Two rotomers present in NMR. ¹H NMR (300 MHz, CDCl₃) δ ppm 0.56 (t, 0.5H), 1.20-1.58 (m, 5.5H), 1.65-2.04 (m, 5H), 2.50 (s, 1.5H), 2.72 (m, 1H), 2.84-3.24 (m, 11.5H), 3.22 (m, 0.5H), 3.54 (m, 0.5H), 3.68 (d, 15 Hz, 0.5H), 3.68 (m, 0.5H), 3.81-3.94 (m, 2H), 3.90 (d, 3H), 4.03 (m, 2H), 4.17 (d, 15 Hz, 0.5H), 4.36 (m, 0.5H), 4.98 (d, 15 Hz, 0.5H), 5.47 (d, 15 Hz, 0.5H), 6.96 (m, 1H), 7.06 (d, 0.5H), 7.12, (d, 0.5H), 7.22 (m, 2H), 7.57 (m, 1H), 7.82 (m, 1H), 7.95 (d, 0.5H), 8.20 (d, 0.5H).

EXAMPLE 3

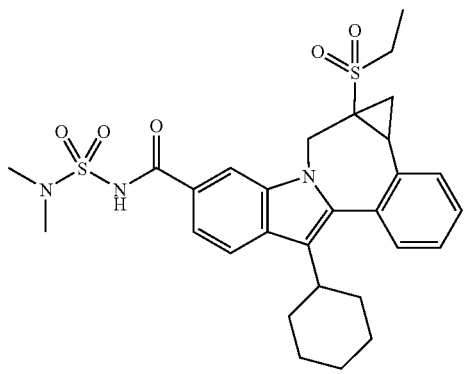

(+/−) Cycloprop[d]indolo[2,1-a][2]benzazepine-5-carboxamide, 8-cyclohexyl-N-[(dimethylamino)sulfonyl]-1a-(ethylsulfonyl)-1,1a,2,12b-tetrahydro-. To a solution of trimethylsulfoxonium iodide (47 mg, 0.22 mmol) in DMSO (1.0 mL) was added 90% NaH (6.0 mg, 0.22 mmol). This mixture was stirred at 22° C. for 15 min followed by addition of 7H-Indolo[2,1-a][2]benzazepine-10-carboxamide, 13-cyclohexyl-N-[(dimethylamino)sulfonyl]-6-(ethylsulfonyl)-(40 mg, 0.072 mmol) in DMSO (1.0 mL). The resulting solution was stirred at 60° C. for 3 hr; 1M HCl (15 mL) was added and the aqueous layer was extracted with CHCl₃ (2×30 mL). The organic phase was dried over Na₂SO₄, filtered, and concentrated under reduced pressure. This oil was purified by reverse-phase prep HPLC to afford the title compound (27 mg, 67%) as a yellow paste. MS m/z 570 (MH⁺). Two rotomers present in NMR. ¹H NMR (300 MHz, CDCl₃) δ ppm 0.42 (t, 0.4H), 0.73 (t, 1.8H), 1.10 (t, 1.2H), 1.20-1.62 (m, 4.6H), 1.71-2.22 (m, 7H), 2.68-3.1 (m, 2.2H), 3.11 (d, 6H), 3.18 (m, 0.6H), 3.68 (m, 1.2H), 3.8 (d, 15 Hz, 0.6H), 4.22 (d, 15 Hz, 0.4H), 5.13 (d, 15 Hz, 0.4H), 5.56 (d, 15 Hz, 0.6H), 7.25-7.62 (m, 4H), 7.71 (d, 0.6H), 7.87-8.05 (m, 1.4H), 8.10 (d, 1H), 8.91-9.10 (m, 1H).

EXAMPLE 4

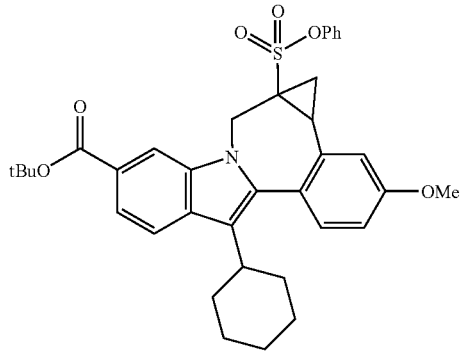

Cycloprop[d]indolo[2,1-a][2]benzazepine-5-carboxylic acid, 8-cyclohexyl-1,1a,2,12b-tetrahydro-11-methoxy-1a-(phenoxysulfonyl)-,1,1-dimethylethyl ester. To a solution of trimethylsulfoxonium iodide (236 mg, 1.07 mmol) in DMSO (3.0 mL) was added 90% NaH (28 mg, 1.07 mmol). This mixture was stirred at 22° C. for 15 min followed by addition of 7H-indolo[2,1-a][2]benzazepine-10-carboxylic acid, 13-cyclohexyl-3-methoxy-6-(phenoxysulfonyl)-, 1,1-dimethylethyl ester (320 mg, 0.534 mmol) in DMSO (2.0 mL). The resulting solution was stirred at 60° C. for 3 hr; 1M HCl (15 mL) was added and the aqueous layer was extracted with CHCl₃ (2×30 mL). The organic phase was dried over Na₂SO₄, filtered, and concentrated under reduced pressure. This oil was purified by silica gel chromatography (1:1 EtOAc:hexanes) to afford the title compound (276 mg, 84%) as a yellow paste. MS m/z 614 (MH⁺), ret time 3.15 min, column B, 4 minute gradient, flow rate 4 mL/min.

EXAMPLE 5

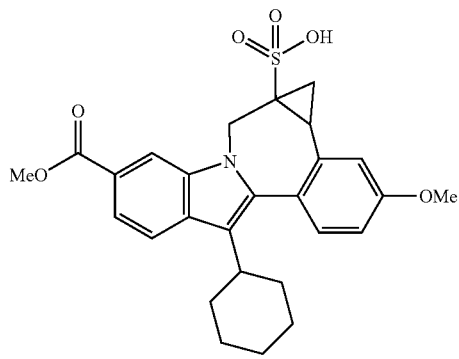

Cycloprop[d]indolo[2,1-a][2]benzazepine-5-carboxylic acid, 8-cyclohexyl-1,1a,2,12b-tetrahydro-11-methoxy-1a-sulfo-, 5-methyl ester. To a solution of cycloprop[d]indolo[2,1-a][2]benzazepine-5-carboxylic acid,8-cyclohexyl-1,1a,2,12b-tetrahydro-11-methoxy-1a-(phenoxysulfonyl)-, 1,1-dimethylethyl ester (150 mg, 0.244 mmol) in THF (2.5 mL) was added 1M tetrabutylammonium hydroxide (2.44 mL in MeOH). The resulting mixture was stirred at 60° C. for 18 hr. 1M HCl (15 mL) was added and the aqueous layer was extracted with $CHCl_3$ (2×15 mL). The organic phase was dried over $Na_2SO_4$, filtered, and concentrated under reduced pressure to afford a white solid. This solid was dissolved in MeOH (10 mL) and 0.04 mL of concentrated HCl. This solution was stirred at 80° C. for 2 hr and concentrated under reduced pressure. The resulting oil was purified by reverse-phase prep HPLC to afford the title compound (100 mg, 83%) as a yellow paste. MS m/z 496 ($MH^+$). $^1H$ NMR (300 MHz, $CDCl_3$) δ ppm 0.30 (t, 1H), 1.20-1.50 (m, 4H), 1.59 (m, 1H), 1.65-2.12 (m, 5H), 2.78 (m, 1H), 2.85 (m, 1H), 3.63 (m, 1H), 3.85 (s, 3H), 3.92 (s, 3H), 4.28 (d, J=15 Hz, 1H), 5.29 (d, J=15 Hz, 1H), 6.82, (m, 1H), 7.13 (d, J=2.5 Hz, 1H), 7.21 (d, J=7.5 Hz, 1H), 7.69 (d, J=7.8 Hz, 1H), 7.80 (d, J=7.8 Hz, 1H), 8.21 (s, 1H).

EXAMPLE 6

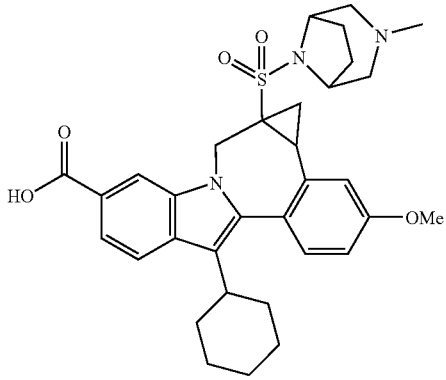

Cycloprop[d]indolo[2,1-a][2]benzazepine-5-carboxylic acid, 8-cyclohexyl-1a-[(3-methyl-3,8-diazabicyclo[3.2.1]oct-8-yl)sulfonyl]1,1a, 2,12b-tetrahydro-11-methoxy-. To a solution of cycloprop[d]indolo[2,1-a][2]benzazepine-5-carboxylic acid, 8-cyclohexyl-1,1a,2,12b-tetrahydro-11-methoxy-1a-sulfo-, 5-methyl ester (100 mg, 0.202 mmol) in $CH_2Cl_2$ (1.0 mL) was added 2M thionyl chloride (1.0 mL). This solution was stirred at 22° C. for 2 hr and concentrated under reduced pressure. The resulting yellow oil was redissolved in $CH_2Cl_2$ (1.0 mL); TEA (0.170 mg, 1.21 mmol) and 3-methyl-3,8-diazabicyclo[3.2.1]octane (47 mg, 0.404 mmol) were added. The resulting mixture was allowed to stir at 22° C. for 16 hr. 1M HCl (15 mL) was added and the aqueous layer was extracted with $CHCl_3$ (2×30 mL). The organic phase was concentrated under reduced pressure. The resulting yellow solid was dissolved in 1:1 MeOH/THF (2.0 mL) and 1M NaOH (2.0 mL) was added. The resulting mixture was stirred at 22° C. for 16 hr. 1M HCl (15 mL) was added and the aqueous layer was extracted with $CHCl_3$ (2×15 mL). The organic phase was dried over $Na_2SO_4$, filtered, and concentrated under reduced pressure to afford a yellow solid. This oil was purified by reverse-phase prep HPLC to afford the title compound (81 mg, 68%) as a yellow paste. MS m/z 590 ($MH^+$). $^1H$ NMR (300 MHz, $CDCl_3$) δ ppm 0.43 (t, 0.5H), 1.20-1.60 (m, 5.5H), 1.65-2.04 (m, 7H), 2.12-2.42 (s, 3.5H), 2.82 (m, 1H), 2.93-3.10 (m, 3.5H), 3.20 (m, 0.5H), 3.50 (m, 0.5H), 3.62 (d, 15 Hz, 0.5H), 3.73 (m, 0.5H), 3.82 (d, J=15 Hz, 0.5H), 3.83-3.94 (m, 2H), 3.92 (d, 3H), 4.11 (m, 1H), 4.21 (d, 15 Hz, 0.5H), 4.55 (m, 1H), 5.06 (d, 15 Hz, 0.5H), 5.57 (d, 15 Hz, 0.5H), 6.97 (m, 1H), 7.05 (d, 0.5H), 7.12 (d, 0.5H), 7.24 (m, 1H), 7.74 (m, 1H), 7.84 (m, 1H), 8.15 (s, 0.5H), 8.32 (s, 0.5H).

The following compounds were synthesized by an analogous method as described above for cycloprop[d]indolo[2,1-a][2]benzazepine-5-carboxylic acid, 8-cyclohexyl-1a-[(3-methyl-3,8-diazabicyclo[3.2.1]oct-8-yl)sulfonyl]-1,1a,2,12b-tetrahydro-11-methoxy-.

EXAMPLE 7

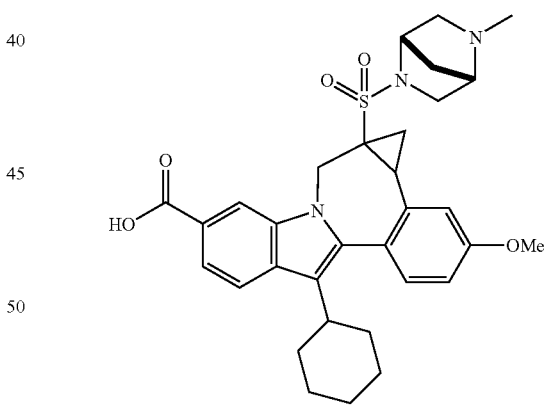

Cycloprop[d]indolo[2,1-a][2]benzazepine-5-carboxylic acid, 8-cyclohexyl-1a-[[(1R,4R)-5-methyl-2,5-diazabicyclo[2.2.1]hept-2-yl]sulfonyl]-1,1a, 2,12b-tetrahydro-11'-methoxy-. MS m/z 576 ($MH^+$). $^1H$ NMR (300 MHz, $CDCl_3$) δ ppm 0.49 (t, 0.5H), 1.20-1.60 (m, 5.5H), 1.65-2.09 (m, 5H), 2.12-2.47 (s, 3.5H), 2.86 (m, 1H), 2.93-3.12 (m, 3.5H), 3.26 (m, 0.5H), 3.49 (m, 0.5H), 3.68 (d, 15 Hz, 0.5H), 3.78 (m, 0.5H), 3.86 (d, J=15 Hz, 0.5H), 3.88-3.96 (m, 2H), 4.01 (d, 3H), 4.09 (m, 1H), 4.19 (d, 15 Hz, 0.5H), 4.57 (m, 1H), 5.12 (d, 15 Hz, 0.5H), 5.54 (d, 15 Hz, 0.5H), 6.95 (m, 1H), 7.04 (d, 0.5H), 7.11 (d, 0.5H), 7.23 (m, 1H), 7.74 (m, 1H), 7.82 (m, 1H), 8.14 (s, 0.5H), 8.34 (s, 0.5H).

EXAMPLE 8

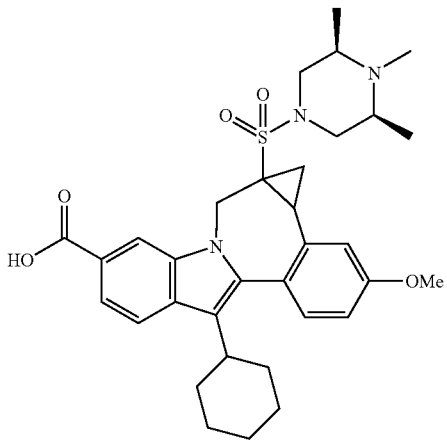

Cycloprop[d]indolo[2,1-a][2]benzazepine-5-carboxylic acid, 8-cyclohexyl-1a[[(3R,5S)-3,4,5-trimethyl-1-piperazinyl]sulfonyl]-1,1a,2,12b-tetrahydro-11-methoxy-. MS m/z 592 (MH$^+$). $^1$H NMR (300 MHz, CDCl$_3$) δ ppm 0.43 (t, 0.5H), 1.10 (m, 3H), 1.20-1.61 (m, 8.5H), 1.72-2.18 (m, 5H), 2.52 (s, 1.5H), 2.69 (m, 1H), 2.78-3.10 (m, 5.5H), 3.39 (m, 1H), 3.55 (m, 1H), 3.66 (d, 15 Hz, 0.5H), 3.74-3.94 (m, 2H), 3.90 (d, 3H), 4.17 (d, 15 Hz, 0.5H), 4.98 (d, 15 Hz, 0.5H), 5.47 (d, 15 Hz, 0.5H), 6.96 (m, 1H), 7.06 (d, 0.5H), 7.14 (d, 0.5H), 7.24 (m, 1H), 7.75 (m, 1H), 7.85 (m, 1H), 8.15 (s, 0.5H), 8.30 (s, 0.5H).

EXAMPLE 9

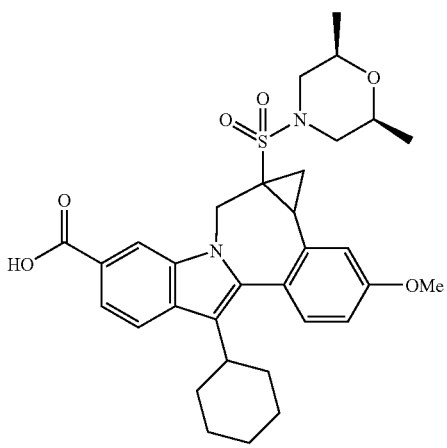

Cycloprop[d]indolo[2,1-a][2]benzazepine-5-carboxylic acid, 8-cyclohexyl-1a-[[(2R,6S)-2,6-dimethyl-4-morpholinyl]sulfonyl]-1,1a,2,12b-tetrahydro-11-methoxy-. MS m/z 579 (MH$^+$). $^1$H NMR (300 MHz, CDCl$_3$) δ ppm 0.48 (t, 0.5H), 1.13 (m, 3H), 1.20-1.61 (m, 8.5H), 1.70-2.14 (m, 5H), 2.72 (m, 1H), 2.82-3.14 (m, 4H), 3.45 (m, 1H), 3.59 (m, 1H), 3.68 (d, 15 Hz, 0.5H), 3.84-3.99 (m, 2H), 3.91 (d, 3H), 4.24 (d, 15 Hz, 0.5H), 4.97 (d, 15 Hz, 0.5H), 5.44 (d, 15 Hz, 0.5H), 6.98 (m, 1H), 7.06 (d, 0.5H), 7.14 (d, 0.5H), 7.26 (m, 1H), 7.75 (m, 1H), 7.84 (m, 1H), 8.16 (s, 0.5H), 8.28 (s, 0.5H).

EXAMPLE 10

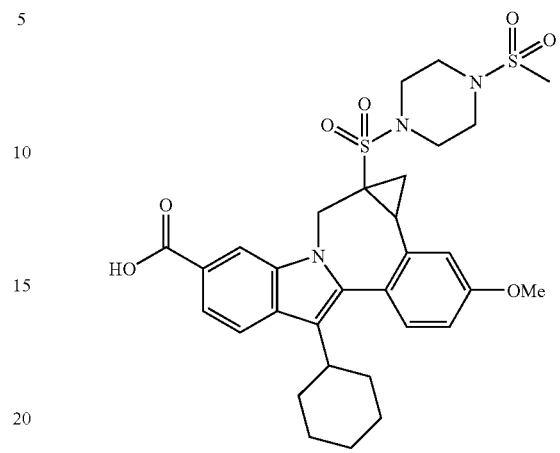

Cycloprop[d]indolo[2,1-a][2]benzazepine-5-carboxylic acid, 8-cyclohexyl-1a-[[4-(methylsulfonyl)-1-piperazinyl]sulfonyl]-1,1a,2,12b-tetrahydro-11-methoxy-. MS m/z 628 (MH$^+$). $^1$H NMR (300 MHz, CDCl$_3$) δ ppm 0.42 (t, 0.5H), 1.22-1.61 (m, 4.5H), 1.66 (m, 1H), 1.74-2.13 (m, 6H), 2.49 (broad s, 1.5H), 2.74 (broad s, 1.5H), 2.80-2.94 (m, 2H), 3.02-3.14 (m, 2H), 3.38-3.52 (m, 4H), 3.60 (m, 2H), 3.78(d, 15 Hz, 0.5H), 3.91 (d, 3H), 4.20 (d, 15 Hz, 0.5H), 5.04 (d, 15 Hz, 0.5H), 5.39 (d, 15 Hz, 0.5H), 6.96 (m, 1H), 7.04 (d, 0.5H), 7.12 (d, 0.5H), 7.22 (m, 1H), 7.73 (m, 1H), 7.81 (m, 1H), 8.12 (s, 0.5H), 8.29 (s, 0.5H).

EXAMPLE 11

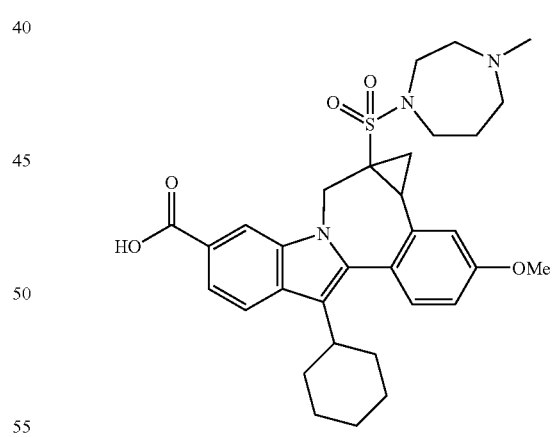

Cycloprop[d]indolo[2,1-a][2]benzazepine-5-carboxylic acid, 8-cyclohexyl-1a-[(hexahydro-4-methyl-1H-1,4-diazepin-1-yl)sulfonyl]-1,1a,2,12b-tetrahydro-11-methoxy-. MS m/z 578 (MH$^+$). $^1$H NMR (300 MHz, CDCl$_3$) δ ppm 0.44 (t, 0.5H), 1.16-1.58 (m, 5.5H), 1.66-2.11 (m, 5H), 2.24 (m, 1H), 2.60-3.21 (m, 9H), 3.32 (m, 2H), 3.44 (m, 1H), 3.54 (m, 1H), 3.72 (d, 15 Hz, 0.5H), 3.75-3.95 (m, 2H), 3.92 (d, 3H), 4.21 (d, 15 Hz, 0.5H), 4.97 (d, 15 Hz, 0.5H), 5.32 (d, 15 Hz, 0.5H), 6.95 (m, 1H), 7.05 (d, 0.5H), 7.09 (d, 0.5H), 7.26 (m, 1H), 7.75 (m, 1H), 7.86 (m, 1H), 8.18 (s, 0.5H), 8.34 (s, 0.5H).

EXAMPLE 12

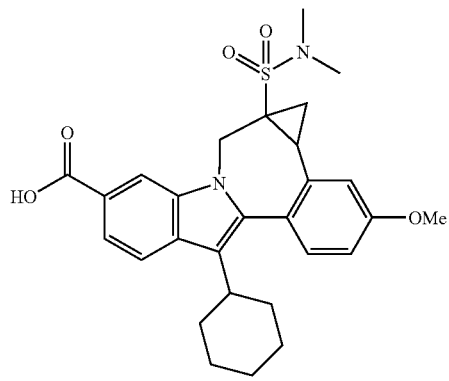

Cycloprop[d]indolo[2,1-a][2]benzazepine-5-carboxylic acid, 8-cyclohexyl-1a-[(dimethylamino)sulfonyl]-1,1a,2,12b-tetrahydro-11-methoxy-. MS m/z 509 (MH+). $^1$H NMR (300 MHz, CDCl$_3$) δ ppm 0.42 (t, 0.5H), 1.19-1.51 (m, 4.5H), 1.60 (m, 1H), 1.65-2.11 (m, 5H), 2.05 (s, 3H), 2.72-2.91 (m, 3H), 3.03 (s, 3H), 3.74 (d, 15 Hz, 0.5H), 3.91 (d, 3H), 4.15 (d, 15 Hz, 0.5H), 5.04 (d, 15 Hz, 0.5H), 5.38 (d, 15 Hz, 0.5H), 6.96 (m, 1H), 7.04 (d, 0.5H), 7.12 (d, 0.5H), 7.21 (m, 1H), 7.72 (m, 1H), 7.83 (m, 1H), 8.16 (s, 0.5H), 8.28 (s, 0.5H).

EXAMPLE 13

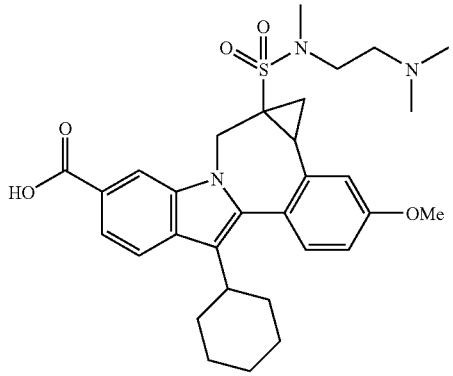

Cycloprop[d]indolo[2,1-a][2]benzazepine-5-carboxylic acid, 8-cyclohexyl-1a-[[[2-(dimethylamino)ethyl]methylamino]sulfonyl]-1,1a,2,12b-tetrahydro-11-methoxy-. MS m/z 566 (MH+). $^1$H NMR (300 MHz, CDCl$_3$) δ ppm 0.44 (t, 0.5H), 1.21-1.60 (m, 5.5H), 1.65-2.11 (m, 5H), 2.46 (d, 6H), 2.76 (m, 1H), 2.84-3.25 (m, 7H), 3.54 (m, 2H), 3.67 (d, 15 Hz, 0.5H), 3.90 (d, 3H), 4.18 (d, 15 Hz, 0.5H), 4.95 (d, 15 Hz, 0.5H), 5.41 (d, 15 Hz, 0.5H), 6.96 (m, 1H), 7.05 (d, 0.5H), 7.12 (d, 0.5H), 7.24 (m, 1H), 7.74 (m, 1H), 7.84 (m, 1H), 8.15 (s, 0.5H), 8.32 (s, 0.5H).

EXAMPLE 14

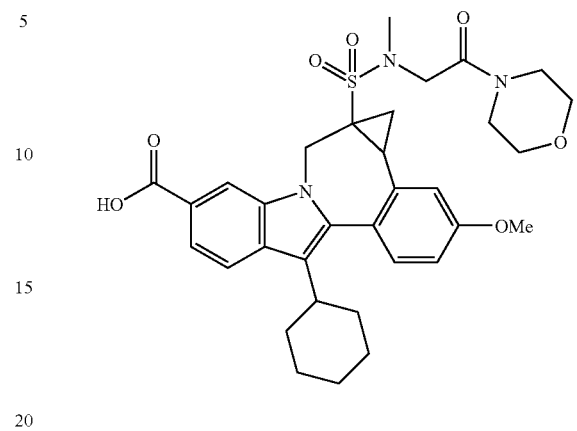

Cycloprop[d]indolo[2,1-a][2]benzazepine-5-carboxylic acid, 8-cyclohexyl-1a-[[methyl[2-(4-morpholinyl)-2-oxoethyl]amino]sulfonyl]-1,1a,2,12b-tetrahydro-11-methoxy-. MS m/z 622 (MH+). $^1$H NMR (300 MHz, CDCl$_3$) δ ppm 0.42 (t, 0.5H), 1.20-1.61 (m, 5.5H), 1.62-2.12 (m, 5H), 2.80 (m, 1H), 2.84-3.10 (m, 6H), 3.48 (m, 2H), 3.63 (m, 0.5H), 3.69-3.82 (m, 6.5H), 3.90 (d, 3H), 4.01 (m, 0.5H), 4.14 (d, 15 Hz, 0.5H), 4.80 (d, 15 Hz, 0.5H), 5.35 (d, 15 Hz, 0.5H), 6.95 (m, 1H), 7.02 (d, 0.5H), 7.14 (d, 0.5H), 7.24 (m, 1H), 7.74 (m, 1H), 7.86 (m, 1H), 8.14 (s, 0.5H), 8.29 (s, 0.5H).

EXAMPLE 15

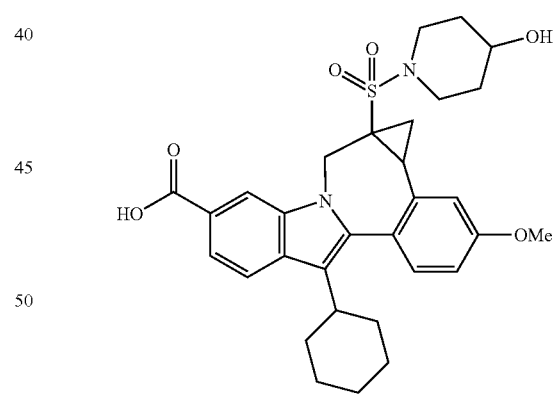

Cycloprop[d]indolo[2,1-a][2]benzazepine-5-carboxylic acid, 8-cyclohexyl-1,1a,2,12b-tetrahydro-1a-[(4-hydroxy-1-piperidinyl)sulfonyl]-11-methoxy-. MS m/z 565 (MH+). $^1$H NMR (300 MHz, CDCl$_3$) δ ppm 0.42 (t, 0.5H), 1.19-1.51 (m, 4.5H), 1.60-2.11 (m, 10H), 2.72-2.91 (m, 3H), 3.21-3.60 (m, 5H), 3.74 (d, 15 Hz, 0.5H), 3.91 (d, 3H), 4.20 (d, 15 Hz, 0.5H), 5.04 (d, 15 Hz, 0.5H), 5.42 (d, 15 Hz, 0.5H), 6.96 (m, 1H), 7.04 (d, 0.5H), 7.12 (d, 0.5H), 7.21 (m, 1H), 7.72 (m, 1H), 7.83 (m, 1H), 8.16 (s, 0.5H), 8.28 (s, 0.5H).

EXAMPLE 16

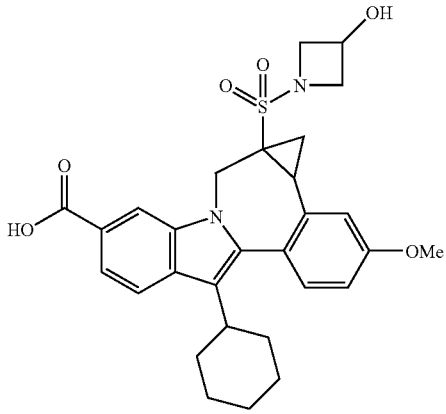

Cycloprop[d]indolo[2,1-a][2]benzazepine-5-carboxylic acid, 8-cyclohexyl-1,1a,2,12b-tetrahydro-1a-[(3-hydroxy-1-azetidinyl)sulfonyl]-11-methoxy-. MS m/z 537 (MH+). ¹H NMR (300 MHz, CDCl₃) δ ppm 0.33 (t, 0.5H), 1.19-1.51 (m, 4.5H), 1.60-2.11 (m, 6H), 2.72-2.91 (m, 2H), 3.01-3.39 (m, 5H), 3.74 (d, 15 Hz, 0.5H), 3.91 (d, 3H), 3.93 (m, 1H), 4.20 (d, 15 Hz, 0.5H), 5.04 (d, 15 Hz, 0.5H), 5.42 (d, 15 Hz, 0.5H), 6.96 (m, 1H), 7.04 (d, 0.5H), 7.12 (d, 0.5H), 7.21 (m, 1H), 7.72 (m, 1H), 7.83 (m, 1H), 8.03 (s, 0.5H), 8.22 (s, 0.5H).

EXAMPLE 17

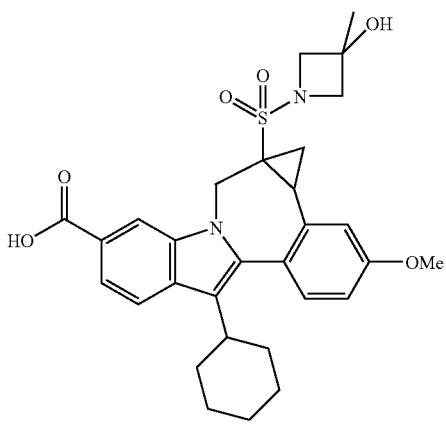

Cycloprop[d]indolo[2,1-a][2]benzazepine-5-carboxylic acid, 8-cyclohexyl-1,1a,2,12b-tetrahydro-1a-[(3-hydroxy-3-methyl-1-azetidinyl)sulfonyl]-11-methoxy-. MS m/z 551 (MH+). ¹H NMR (300 MHz, CDCl₃) δ ppm 0.1 (t, 0.5H), 1.19-1.51 (m, 7.5H), 1.60-2.13 (m, 6H), 2.74-2.89 (m, 2H), 3.01-3.30 (m, 4H), 3.50 (m, 1H), 3.74 (d, 15 Hz, 0.5H), 3.89 (d, 3H), 4.15 (d, 15 Hz, 0.5H), 5.12 (d, 15 Hz, 0.5H), 5.41 (d, 15 Hz, 0.5H), 6.96 (m, 1H), 7.04 (d, 0.5H), 7.12 (d, 0.5H), 7.21 (m, 1H), 7.72 (m, 1H), 7.83 (m, 1H), 8.25 (s, 0.5H), 8.28 (s, 0.5H).

EXAMPLE 18

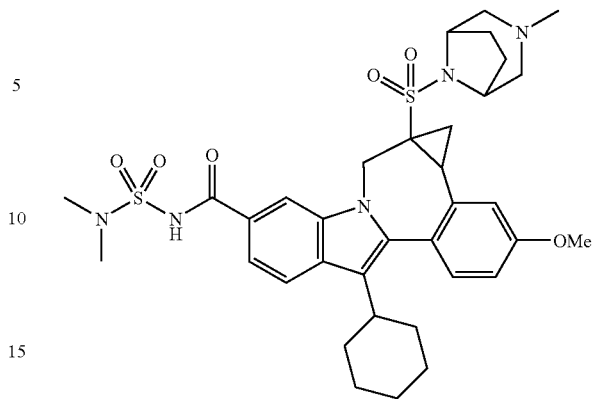

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[(3-methyl-3,8-diazabicyclo[3.2.1]oct-8-yl)sulfonyl]-. To a solution of cycloprop[d]indolo[2,1-a][2]benzazepine-5-carboxylic acid,8-cyclohexyl-1a-[(3-methyl-3,8-diazabicyclo[3.2.1]oct-8-yl)sulfonyl]-1,1a,2,12b-tetrahydro-11-methoxy-(42 mg, 0.071 mmol) in THF (1.5 mL) was added CDI (58 mg, 0.355 mmol) and the resulting solution was heated 60° C. for 1 hr. Dimethylsulfamide (108 mg, 0.710 mmol) and DBU (0.44 mL, 0.355 mmol) were added. The resulting mixture was allowed to stir at 60° C. for 1 hr and 22° C. for 16 hr. 1M HCl (15 mL) was added and the aqueous layer was extracted with CHCl₃ (2×30 mL). The organic phase was concentrated under reduced pressure. This oil was purified by reverse-phase prep HPLC to afford the title compound (34 mg, 69%) as a yellow paste. MS m/z 696 (MH+). Two rotomers present in NMR. ¹H NMR (300 MHz, CDCl₃) δ ppm 0.40 (t, 0.5H), 1.20-1.60 (m, 5.5H), 1.65-2.04 (m, 7H), 2.12-2.42 (s, 3.5H), 2.81 (m, 1H), 2.93-3.10 (m, 9.5H), 3.19 (m, 0.5H), 3.50 (m, 0.5H), 3.64 (d, 15 Hz, 0.5H), 3.71 (m, 0.5H), 3.81 (d, J=15 Hz, 0.5H), 3.83-3.94 (m, 2H), 3.90 (d, 3H), 4.11 (m, 1H), 4.22 (d, 15 Hz, 0.5H), 4.55 (m, 1H), 5.05 (d, 15 Hz, 0.5H), 5.57 (d, 15 Hz, 0.5H), 6.96 (m, 1H), 7.06 (d, 0.5H), 7.12 (d, 0.5H), 7.22 (m, 2H), 7.41 (m, 0.5H), 7.54 (m, 0.5H), 7.82 (m, 1H), 7.95 (d, 0.5H), 8.20 (d, 0.5H).

The following compounds were synthesized by an analogous method as described above for cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[(3-methyl-3,8-diazabicyclo[3.2.1]oct-8-yl)sulfonyl]-.

EXAMPLE 19

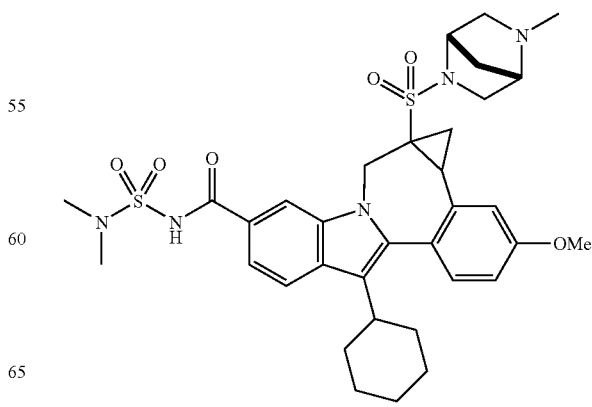

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[(1R,4R)-5-methyl-2,5-diazabicyclo[2,2]hept-2-yl]sulfonyl]-. MS m/z 682 (MH+). Two rotomers present in NMR. ¹H NMR (300 MHz, CDCl₃) δ ppm 0.51 (t, 0.5H), 1.20-1.60 (m, 5.5H), 1.65-2.09 (m, 5H), 2.12-2.47 (s, 3.5H), 2.85 (m, 1H), 2.93-3.12 (m, 9.5H), 3.23 (m, 0.5H), 3.52 (m, 0.5H), 3.69 (d, 15 Hz, 0.5H), 3.74 (m, 0.5H), 3.82 (d, J=15 Hz, 0.5H), 3.83-3.93 (m, 2H), 3.94 (d, 3H), 4.06 (m, 1H), 4.19 (d, 15 Hz, 0.5H), 4.57 (m, 1H), 5.11 (d, 15 Hz, 0.5H), 5.54 (d, 15 Hz, 0.5H), 6.98 (m, 1H), 7.06 (d, 0.5H), 7.15 (d, 0.5H), 7.25 (m, 2H), 7.41 (m, 0.5H), 7.56 (m, 0.5H), 7.79 (m, 1H), 7.96 (d, 0.5H), 8.21 (d, 0.5H).

EXAMPLE 20

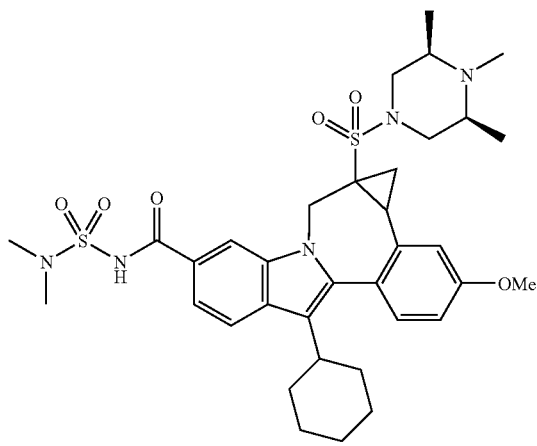

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[(3R,5S)-3,4,5-trimethyl-1-piperazinyl]sulfonyl]-. MS m/z 698 (MH+). Two rotomers present in NMR. ¹H NMR (300 MHz, CDCl₃) δ ppm 0.39 (t, 0.5H), 1.10 (m, 3H), 1.20-1.58 (m, 8.5H), 1.72-2.18 (m, 5H), 2.50 (s, 1.5H), 2.69 (m, 1H), 2.79-3.09 (m, 11.5H), 3.39 (m, 1H), 3.52 (m, 1H), 3.67 (d, 15 Hz, 0.5H), 3.74-3.94 (m, 2H), 3.91 (d, 3H), 4.20 (d, 15 Hz, 0.5H), 4.99 (d, 15 Hz, 0.5H), 5.42 (d, 15 Hz, 0.5H), 6.96 (m, 1H), 7.06 (d, 0.5H), 7.14 (d, 0.5H), 7.22 (m, 2H), 7.57 (m, 1H), 7.82 (m, 1H), 7.95 (d, 0.5H), 8.20 (d, 0.5H).

EXAMPLE 21

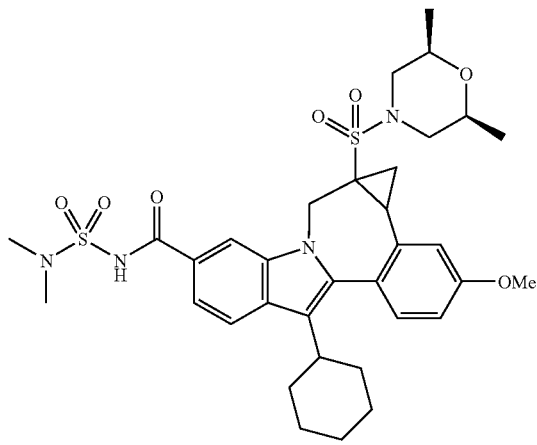

Cycloprop[d]indolo[2,1-a][2]benzazepine-5-carboxamide, 8-cyclohexyl-N-[(dimethylamino)sulfonyl]-1a-[[(2R,6S)-2,6-dimethyl-4-morpholinyl]sulfonyl]-1,1a,2,12b-tetrahydro-11-methoxy-. MS m/z 685 (MH+). Two rotomers present in NMR. ¹H NMR (300 MHz, CDCl₃) δ ppm 0.49 (t, 0.5H), 1.12 (m, 3H), 1.20-1.58 (m, 8.5H), 1.70-2.14 (m, 5H), 2.73 (m, 1H), 2.82-3.14 (m, 10H), 3.45 (m, 1H), 3.59 (m, 1H), 3.67 (d, 15 Hz, 0.5H), 3.84-3.99 (m, 2H), 3.92 (d, 3H), 4.22 (d, 15 Hz, 0.5H), 4.97 (d, 15 Hz, 0.5H), 5.42 (d, 15 Hz, 0.5H), 6.95 (m, 1H), 7.07 (d, 0.5H), 7.11 (d, 0.5H), 7.25 (m, 2H), 7.52 (m, 1H), 7.82 (m, 1H), 7.99 (d, 0.5H), 8.24 (d, 0.5H).

EXAMPLE 22

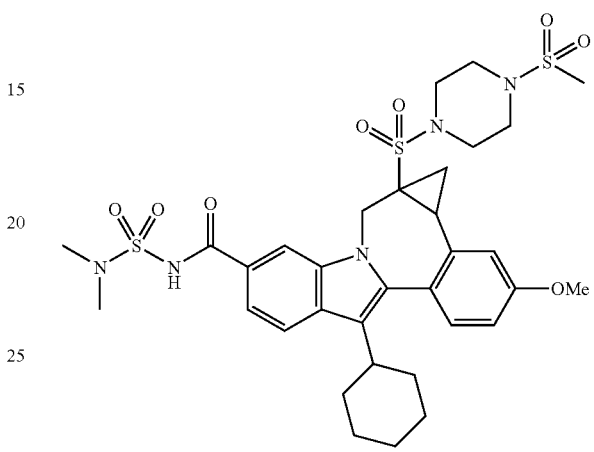

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(methylsulfonyl)-1-piperazinyl]sulfonyl]-. MS m/z 734 (MH+). Two rotomers present in NMR. ¹H NMR (300 MHz, CDCl₃) δ ppm 0.43 (t, 0.5H), 1.22-1.61 (m, 4.5H), 1.65 (m, 1H), 1.75-2.13 (m, 6H), 2.52 (broad s, 1.5H), 2.72 (broad s, 1.5H), 2.80-2.94 (m, 2H), 3.00-3.19 (m, 8H), 3.38-3.52 (m, 4H), 3.59 (m, 2H), 3.76(d, 15 Hz, 0.5H), 3.91 (d, 3H), 4.19 (d, 15 Hz, 0.5H), 5.03 (d, 15 Hz, 0.5H), 5.42 (d, 15 Hz, 0.5H), 6.96 (m, 1H), 7.06 (d, 0.5H), 7.12 (d, 0.5H), 7.22 (m, 1H), 7.39 (m, 0.5H), 7.48 (m, 0.5H), 7.92 (m, 1H), 8.07 (d, 1H), 8.70 (broad s, 0.5H), 8.84 (broad s, 0.5H).

EXAMPLE 23

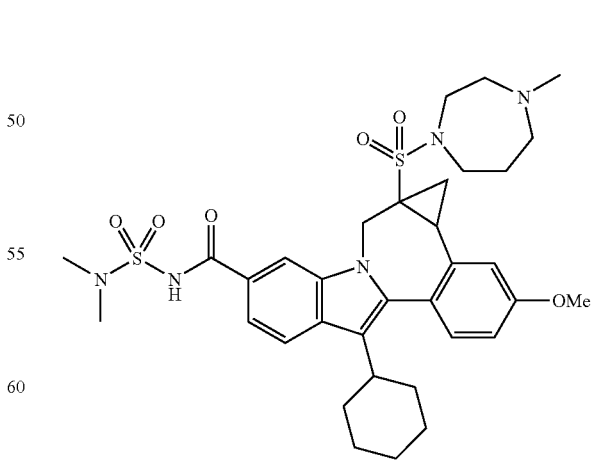

Cycloprop[d]indolo[2,1-a][2]benzazepine-5-carboxamide, 8-cyclohexyl-N-[(dimethylamino)sulfonyl]-1a-[(hexahydro-4-methyl-1H-1,4-diazepin-1-yl)sulfonyl]-1,1a, 2,12b-tetrahydro-11-methoxy-. MS m/z 684 (MH+). Two rotomers present in NMR. ¹H NMR (300 MHz, CDCl₃) δ ppm 0.42 (t, 0.5H), 1.18-1.59 (m, 5.5H), 1.65-2.12 (m, 5H), 2.24 (m, 1H), 2.60-3.21 (m, 15H), 3.31 (m, 2H), 3.44 (m, 1H), 3.53 (m, 1H), 3.72 (d, 15 Hz, 0.5H), 3.75-3.94 (m, 2H), 3.90 (d, 3H), 4.21 (d, 15 Hz, 0.5H), 4.97 (d, 15 Hz, 0.5H), 5.32 (d, 15 Hz, 0.5H), 6.96 (m, 1H), 7.06 (d, 0.5H), 7.12 (d, 0.5H), 7.22 (m, 2H), 7.57 (m, 1H), 7.82 (m, 1H), 7.95 (d, 0.5H), 8.20 (d, 0.5H).

EXAMPLE 24

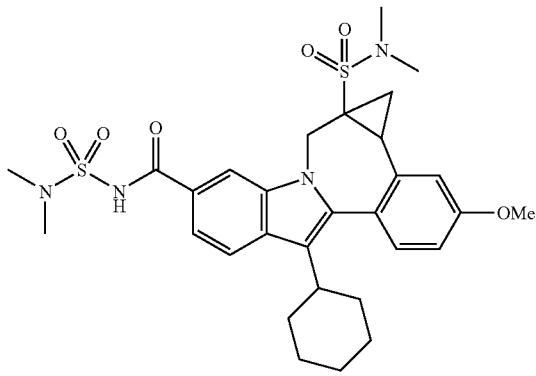

Cycloprop[d]indolo[2,1-a][2]benzazepine-5-carboxamide, 8-cyclohexyl-N, 1a-bis[(dimethylamino)sulfonyl]-1,1a,2,12b-tetrahydro-11-methoxy-. MS m/z 615 (MH+). Two rotomers present in NMR. ¹H NMR (300 MHz, CDCl₃) δ ppm 0.39 (t, 0.5H), 1.20-1.50 (m, 4.5H), 1.59 (m, 1H), 1.65-2.09 (m, 5H), 2.02 (s, 3H), 2.72-2.90 (m, 3H), 3.03 (s, 3H), 3.08 (d, 6H), 3.73 (d, 15 Hz, 0.5H), 3.90 (d, 3H), 4.15 (d, 15 Hz, 0.5H), 5.04 (d, 15 Hz, 0.5H), 5.38 (d, 15 Hz, 0.5H), 6.96 (m, 1H), 7.06 (d, 0.5H), 7.13 (d, 0.5H), 7.32 (m, 2H), 7.43 (m, 1H), 7.90 (m, 1H), 8.00 (d, 0.5H), 8.53 (d, 0.5H).

EXAMPLE 25

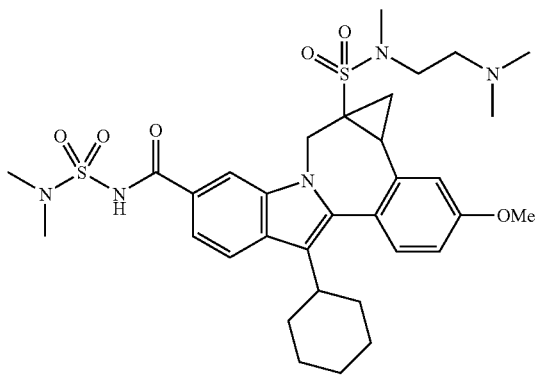

Cycloprop[d]indolo[2,1-a][2]benzazepine-5-carboxamide, 8-cyclohexyl-1a-[[[2-(dimethylamino)ethyl]methylamino]sulfonyl]-N-[(dimethylamino)sulfonyl]-1,1a,2,12b-tetrahydro-11-methoxy-. MS m/z 672 (MH+). Two rotomers present in NMR. ¹H NMR (300 MHz, CDCl₃) δ ppm 0.48 (t, 0.5H), 1.20-1.58 (m, 5.5H), 1.65-2.09 (m, 5H), 2.45 (d, 6H), 2.76 (m, 1H), 2.82-3.28 (m, 13H), 3.54 (m, 2H), 3.68 (d, 15 Hz, 0.5H), 3.90 (d, 3H), 4.17 (d, 15 Hz, 0.5H), 4.98 (d, 15 Hz, 0.5H), 5.47 (d, 15 Hz, 0.5H), 6.96 (m, 1H), 7.05 (d, 0.5H), 7.13 (d, 0.5H), 7.22 (m, 2H), 7.56 (m, 1H), 7.82 (m, 1H), 7.94 (d, 0.5H), 8.20 (d, 0.5H).

EXAMPLE 26

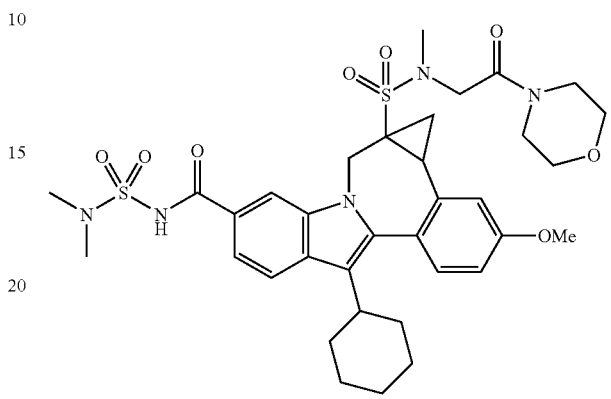

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[methyl[2-(4-morpholinyl)-2-oxoethyl]amino]sulfonyl]-. MS m/z 728 (MH+). Two rotomers present in NMR. ¹H NMR (300 MHz, CDCl₃) δ ppm 0.41 (t, 0.5H), 1.20-1.61 (m, 5.5H), 1.62-2.11 (m, 5H), 2.79 (m, 1H), 2.84-3.10 (m, 12H), 3.46 (m, 2H), 3.60 (m, 0.5H), 3.69-3.81 (m, 6.5H), 3.90 (d, 3H), 3.98 (m, 0.5H), 4.14 (d, 15 Hz, 0.5H), 4.82 (d, 15 Hz, 0.5H), 5.33 (d, 15 Hz, 0.5H), 6.96 (m, 1H), 7.12 (d, 1H), 7.26 (m, 0.5H), 7.31 (m, 1H), 7.48 (m, 0.5H), 7.79 (m, 2H), 8.96 (s, 1H).

EXAMPLE 27

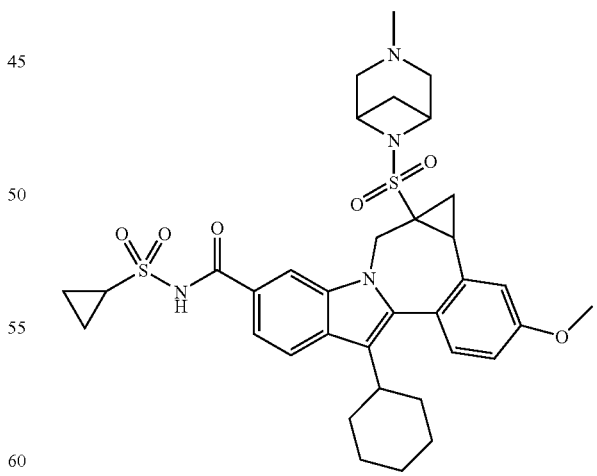

Cycloprop[d]indolo[2,1-a][2]benzazepine-5-carboxamide, 8-cyclohexyl-N-(cyclopropylsulfonyl)-1,1a,2,12b-tetrahydro-11-methoxy-1a-[(3-methyl-3,6-diazabicyclo[3.1.1]hept-6-yl)sulfonyl]-. LCMS: m/e 679 (M+H), ret time 2.33 min, column A, 4 minute gradient, flow rate 4 mL/min.

EXAMPLE 28

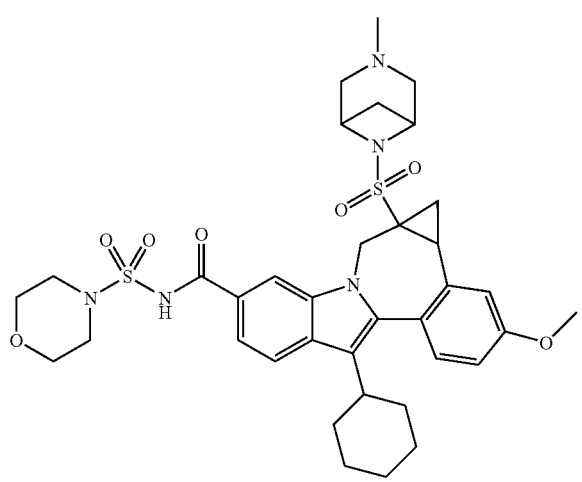

Cycloprop[d]indolo[2,1-a][2]benzazepine-5-carboxamide, 8-cyclohexyl-1,1a,2,12b-tetrahydro-11-methoxy-1a-[(3-methyl-3,6-diazabicyclo[3.1.1]hept-6-yl)sulfonyl]-N-(4-morpholinylsulfonyl)-. LCMS: m/e 724 (M+H), ret time 2.32 min, column A, 4 minute gradient, flow rate 4 mL/min.

EXAMPLE 29

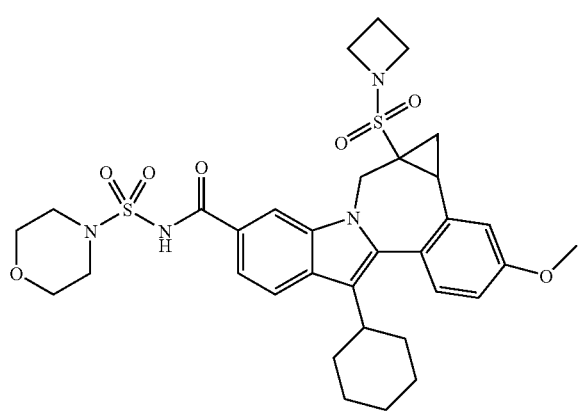

Cycloprop[d]indolo[2,1-a][2]benzazepine-5-carboxamide, 1a-(1-azetidinylsulfonyl)-8-cyclohexyl-1,1a,2,12b-tetrahydro-11-methoxy-N-(4-morpholinylsulfonyl)-. LCMS: m/e 669 (M+H), ret time 2.84 min, column A, 4 minute gradient, flow rate 4 mL/min.

EXAMPLE 30

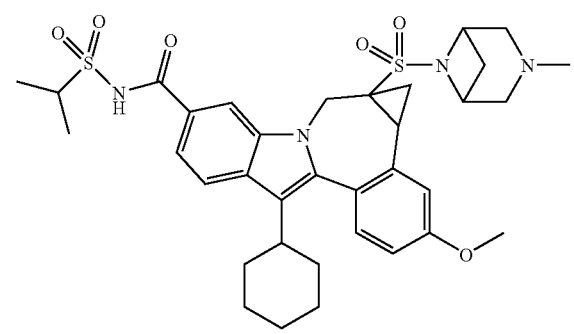

Cycloprop[d]indolo[2,1-a][2]benzazepine-5-carboxamide, 8-cyclohexyl-1,1a,2,12b-tetrahydro-11-methoxy-1a-[(3-methyl-3,6-diazabicyclo[3.1.1]hept-6-yl)sulfonyl]-N-[(1-methylethyl)sulfonyl]-. LCMS: m/e 681 (M+H), ret time 2.41 min, column A, 4 minute gradient, flow rate 4 mL/min.

EXAMPLE 31

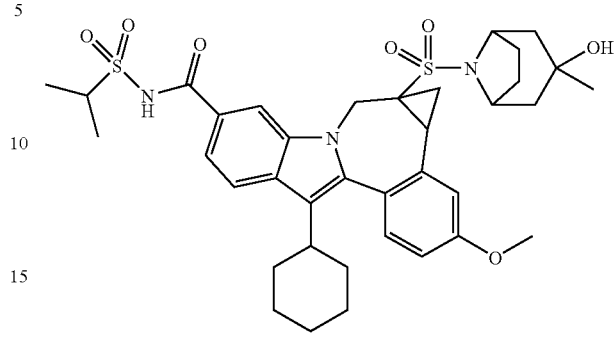

Cycloprop[d]indolo[2,1-a][2]benzazepine-5-carboxamide, 8-cyclohexyl-1,1a, 2,12b-tetrahydro-1a-[(3-hydroxy-3-methyl-8-azabicyclo[3.2.1]oct-8-yl)sulfonyl]-11-methoxy-N-[(1-methylethyl)sulfonyl]-. LCMS: m/e 710 (M+H), ret time 2.76 min, column A, 4 minute gradient, flow rate 4 mL/min.

EXAMPLE 32

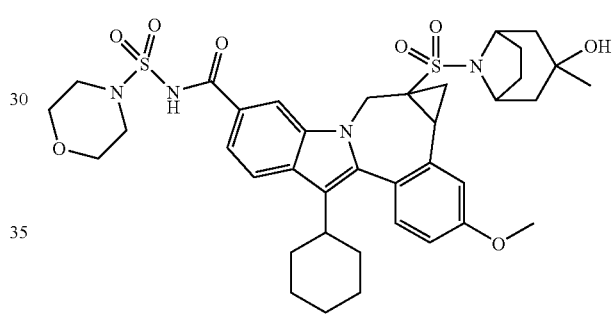

Cycloprop[d]indolo[2,1-a][2]benzazepine-5-carboxamide, 8-cyclohexyl-1,1a, 2,12b-tetrahydro-1a-[(3-hydroxy-3-methyl-8-azabicyclo[3.2.1]oct-8-yl)sulfonyl]-11-methoxy-N-(4-morpholinylsulfonyl)-. LCMS: m/e 753 (M+H), ret time 2.73 min, column A, 4 minute gradient, flow rate 4 mL/min.

EXAMPLE 33

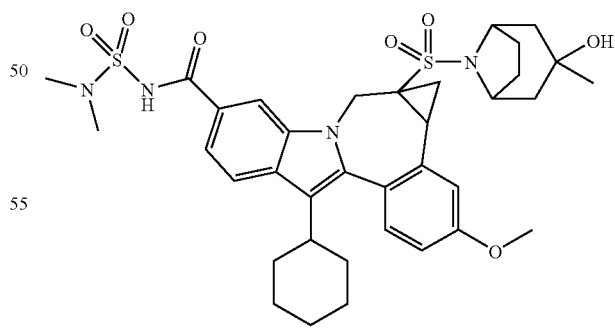

Cycloprop[d]indolo[2,1-a][2]benzazepine-5-carboxamide, 8-cyclohexyl-N-[(dimethylamino)sulfonyl]-1,1a,2,12b-tetrahydro-1a-[(3-hydroxy-3-methyl-8-azabicyclo[3.2.1]oct-8-yl)sulfonyl]-11-methoxy-. LCMS: m/e 711 (M+H), ret time 3.10 min, column A, 4 minute gradient, flow rate 4 mL/min.

EXAMPLE 34

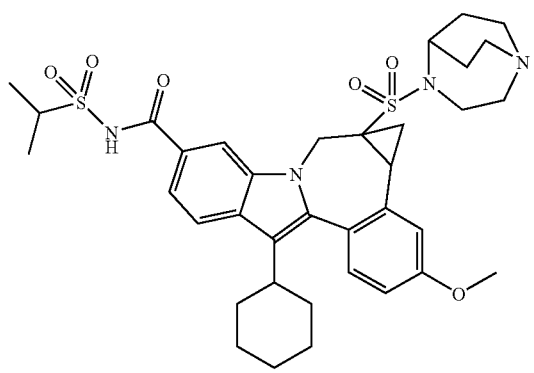

Cycloprop[d]indolo[2,1-a][2]benzazepine-5-carboxamide, 8-cyclohexyl-1a-(1,4-diazabicyclo[3.2.2]non-4-ylsulfonyl)-1,1a,2,12b-tetrahydro-11-methoxy-N-[(1-methylethyl)sulfonyl]-. LCMS: m/e 695 (M+H), ret time 2.55 min, column A, 4 minute gradient, flow rate 4 mL/min.

EXAMPLE 35

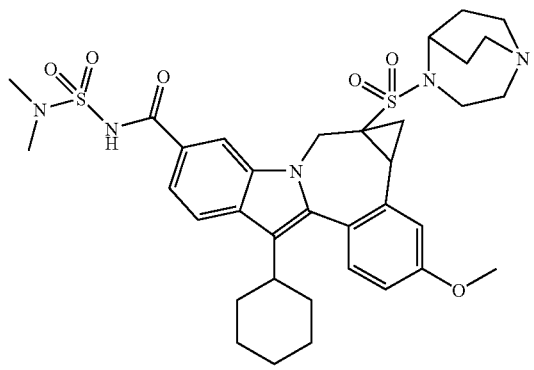

Cycloprop[d]indolo[2,1-a][2]benzazepine-5-carboxamide, 8-cyclohexyl-1a-(1,4-diazabicyclo[3.2.2]non-4-ylsulfonyl)-N-[(dimethylamino)sulfonyl]-1,1a,2,12b-tetrahydro-1'-methoxy-. LCMS: m/e 696 (M+H), ret time 2.58 min, column A, 4 minute gradient, flow rate 4 mL/min.

EXAMPLE 36

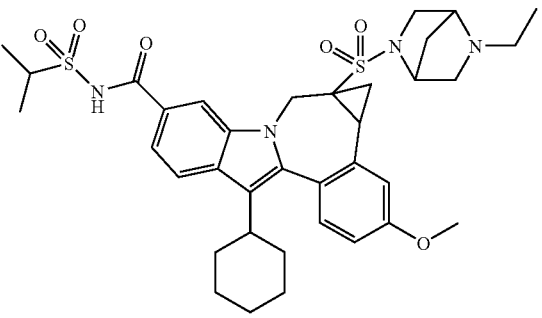

Cycloprop[d]indolo[2,1-a][2]benzazepine-5-carboxamide, 8-cyclohexyl-1a-[(5-ethyl-2,5-diazabicyclo[2.2.1]hept-2-yl)sulfonyl]-1,1a,2,12b-tetrahydro-11-methoxy-N-[(1-methylethyl)sulfonyl]-. LCMS: m/e 695 (M+H), ret time 2.48 min, column A, 4 minute gradient, flow rate 4 mL/min.

EXAMPLE 37

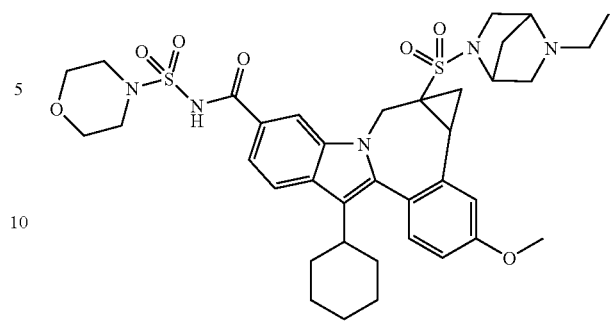

Cycloprop[d]indolo[2,1-a][2]benzazepine-5-carboxamide, 8-cyclohexyl-1a-[(5-ethyl-2,5-diazabicyclo[2.2.1]hept-2-yl)sulfonyl]-1,1a,2,12b-tetrahydro-11-methoxy-N-(4-morpholinylsulfonyl)-. LCMS: m/e 738 (M+H), ret time 2.46 min, column A, 4 minute gradient, flow rate 4 mL/min.

EXAMPLE 38

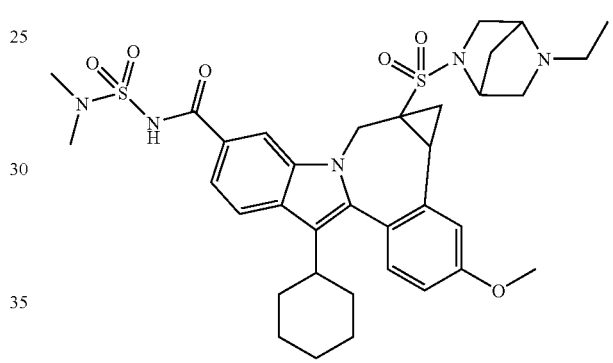

Cycloprop[d]indolo[2,1-a][2]benzazepine-5-carboxamide, 8-cyclohexyl-N-[(dimethylamino)sulfonyl]-1a-[(5-ethyl-2,5-diazabicyclo[2.2.1]hept-2-yl)sulfonyl]-1,1a,2,12b-tetrahydro-11-methoxy-. LCMS: m/e 696 (M+H), ret time 2.41 min, column A, 4 minute gradient, flow rate 4 mL/min.

EXAMPLE 39

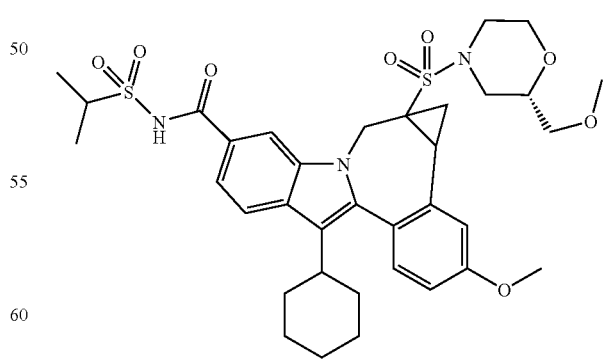

Cycloprop[d]indolo[2,1-a][2]benzazepine-5-carboxamide, 8-cyclohexyl-1,1a, 2,12b-tetrahydro-11-methoxy-1a-[[(2S)-2-(methoxymethyl)-4-morpholinyl]sulfonyl]-N-[(1-methylethyl)sulfonyl]-. LCMS: m/e 700 (M+H), ret time 2.67 min, column A, 4 minute gradient, flow rate 4 mL/min.

EXAMPLE 40

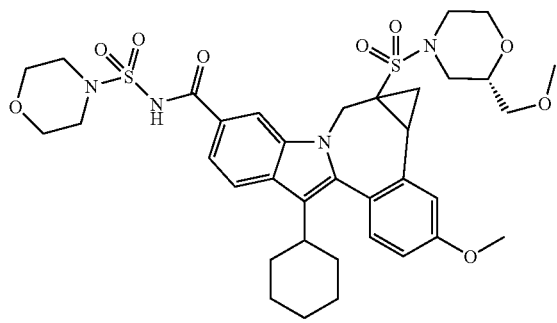

Cycloprop[d]indolo[2,1-a][2]benzazepine-5-carboxamide, 8-cyclohexyl-1,1a, 2,12b-tetrahydro-11-methoxy-1a-[[(2S)-2-(methoxymethyl)-4-morpholinyl]sulfonyl]-N-(4-morpholinylsulfonyl)-. LCMS: m/e 743 (M+H), ret time 2.69 min, column A, 4 minute gradient, flow rate 4 mL/min.

EXAMPLE 41

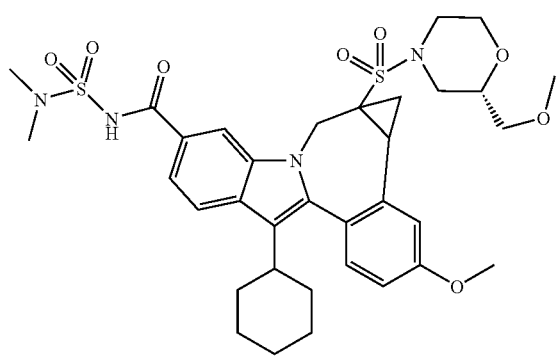

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[(2S)-2-(methoxymethyl)-4-morpholinyl]sulfonyl]-. LCMS: m/e 701 (M+H), ret time 3.02 min, column A, 4 minute gradient, flow rate 4 mL/min.

EXAMPLE 42

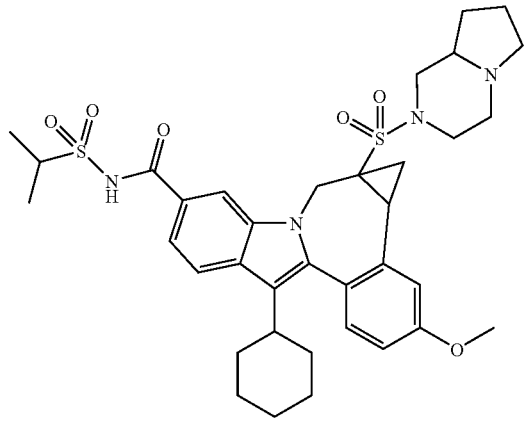

Cycloprop[d]indolo[2,1-a][2]benzazepine-5-carboxamide, 8-cyclohexyl-1a-[(hexahydropyrrolo[1,2-a]pyrazin-2(1H)-yl)sulfonyl]-1,1a,2,12b-tetrahydro-11-methoxy-N-[(1-methylethyl)sulfonyl]-. LCMS: m/e 695 (M+H), ret time 2.72 min, column A, 4 minute gradient, flow rate 4 mL/min.

EXAMPLE 43

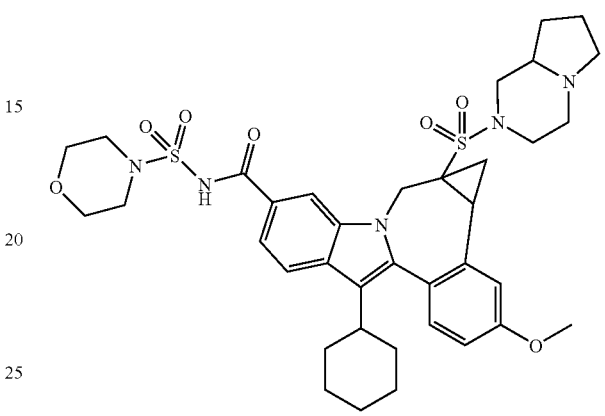

Cycloprop[d]indolo[2,1-a][2]benzazepine-5-carboxamide, 8-cyclohexyl-1a-[(hexahydropyrrolo[1,2-a]pyrazin-2(1H)-yl)sulfonyl]-1,1a,2,12b-tetrahydro-11-methoxy-N-(4-morpholinylsulfonyl)-. LCMS: m/e 738 (M+H), ret time 2.61 min, column A, 4 minute gradient, flow rate 4 mL/min.

EXAMPLE 44

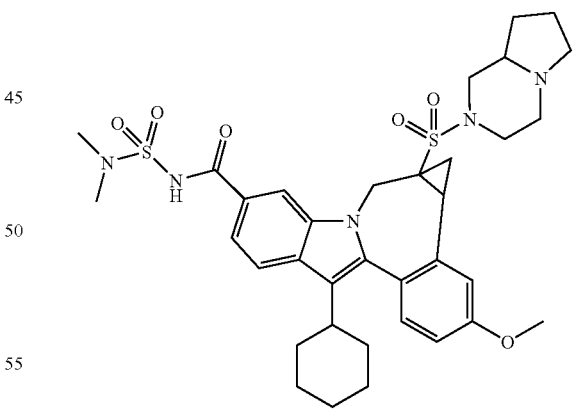

Cycloprop[d]indolo[2,1-a][2]benzazepine-5-carboxamide, 8-cyclohexyl-N-[(dimethylamino)sulfonyl]-1a-[(hexahydropyrrolo[1,2-a]pyrazin-2(1H)-yl)sulfonyl]-1,1a,2,12b-tetrahydro-11-methoxy-. LCMS: m/e 696 (M+H), ret time 2.92 min, column A, 4 minute gradient, flow rate 4 mL/min.

EXAMPLE 45

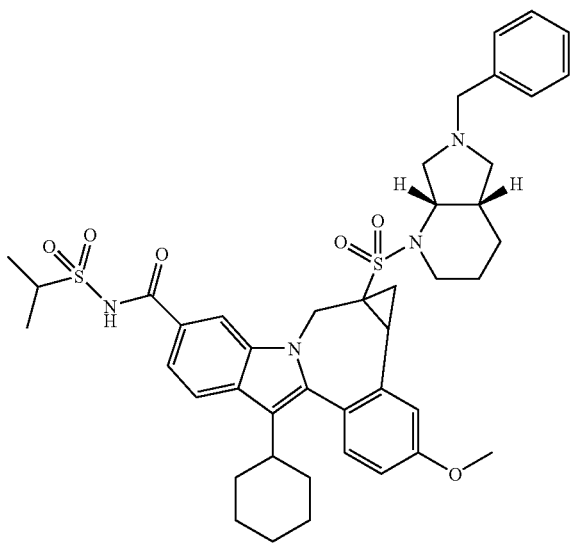

Cycloprop[d]indolo[2,1-a][2]benzazepine-5-carboxamide, 8-cyclohexyl-1,1a, 2,12b-tetrahydro-11-methoxy-N-[(1-methylethyl)sulfonyl]-1a-[[(4aS,7aS)-octahydro-6-(phenylmethyl)-1H-pyrrolo[3,4-b]pyridin-1-yl]. LCMS: m/e 785 (M+H), ret time 3.02 min, column A, 4 minute gradient, flow rate 4 mL/min.

EXAMPLE 46

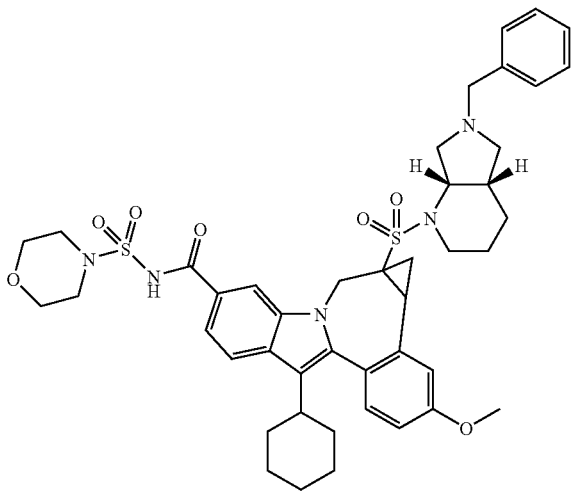

Cycloprop[d]indolo[2,1-a][2]benzazepine-5-carboxamide, 8-cyclohexyl-1,1a,2,12b-tetrahydro-11-methoxy-N-(4-morpholinylsulfonyl)-1a-[[(4aS,7aS)-octahydro-6-(phenylmethyl)-1H-pyrrolo[3,4-b]pyridin-1-yl]. LCMS: m/e 828 (M+H), ret time 2.93 min, column A, 4 minute gradient, flow rate 4 mL/min.

EXAMPLE 47

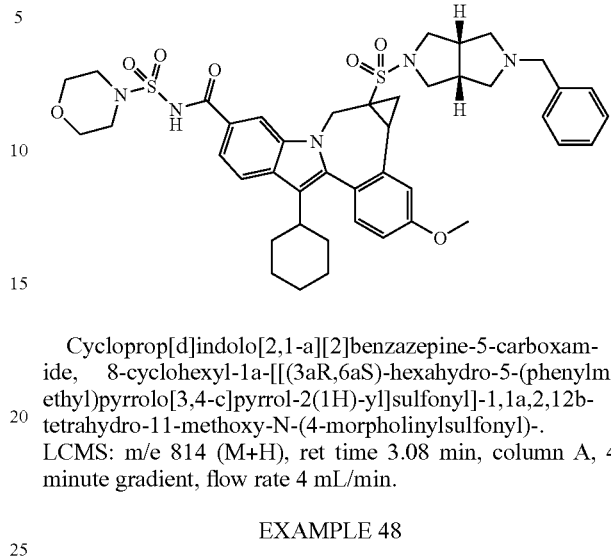

Cycloprop[d]indolo[2,1-a][2]benzazepine-5-carboxamide, 8-cyclohexyl-1a-[[(3aR,6aS)-hexahydro-5-(phenylmethyl)pyrrolo[3,4-c]pyrrol-2(1H)-yl]sulfonyl]-1,1a,2,12b-tetrahydro-11-methoxy-N-(4-morpholinylsulfonyl)-.
LCMS: m/e 814 (M+H), ret time 3.08 min, column A, 4 minute gradient, flow rate 4 mL/min.

EXAMPLE 48

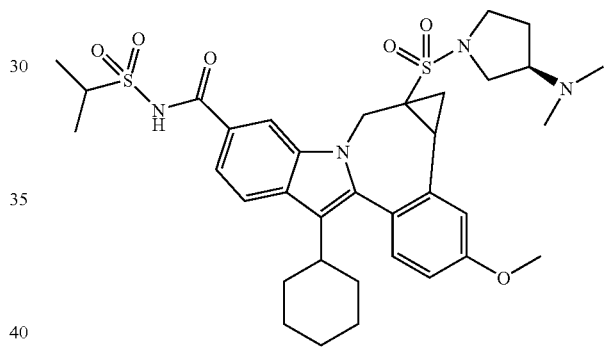

Cycloprop[d]indolo[2,1-a][2]benzazepine-5-carboxamide, 8-cyclohexyl-1a-[[(3R)-3-(dimethylamino)-1-pyrrolidinyl]sulfonyl]-1,1a,2,12b-tetrahydro-11-methoxy-N-[(1-methylethyl)sulfonyl]-. LCMS: m/e 683 (M+H), ret time 2.32 min, column A, 4 minute gradient, flow rate 4 mL/min.

EXAMPLE 49

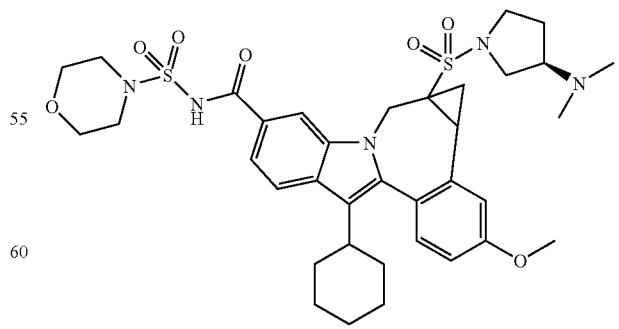

Cycloprop[d]indolo[2,1-a][2]benzazepine-5-carboxamide, 8-cyclohexyl-1a-[[(3R)-3-(dimethylamino)-1-pyrrolidinyl]sulfonyl]-1,1a,2,12b-tetrahydro-11-methoxy-N-(4-morpholinylsulfonyl)-. LCMS: m/e 726 (M+H), ret time 3.34 min, column A, 4 minute gradient, flow rate 4 mL/min.

EXAMPLE 50

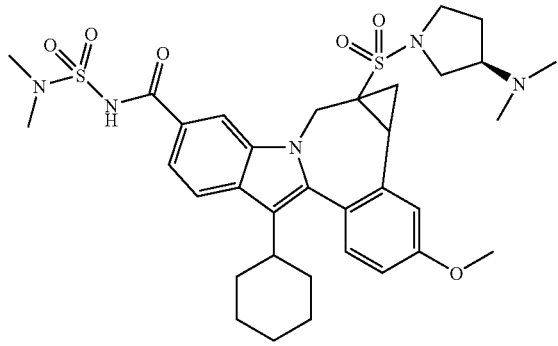

Cycloprop[d]indolo[2,1-a][2]benzazepine-5-carboxamide, 8-cyclohexyl-1a-[[(3R)-3-(dimethylamino)-1-pyrrolidinyl]sulfonyl]-N-[(dimethylamino)sulfonyl]-1,1a,2,12b-tetrahydro-11-methoxy-. LCMS: m/e 684 (M+H), ret time 2.48 min, column A, 4 minute gradient, flow rate 4 mL/min.

EXAMPLE 51

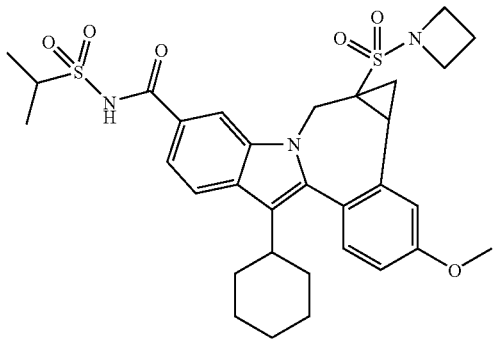

Cycloprop[d]indolo[2,1-a][2]benzazepine-5-carboxamide, 1a-(1-azetidinylsulfonyl)-8-cyclohexyl-1,1a,2,12b-tetrahydro-11-methoxy-N-[(1-methylethyl)sulfonyl]-. LCMS: m/e 626 (M+H), ret time 2.80 min, column A, 4 minute gradient, flow rate 4 mL/min.

EXAMPLE 52

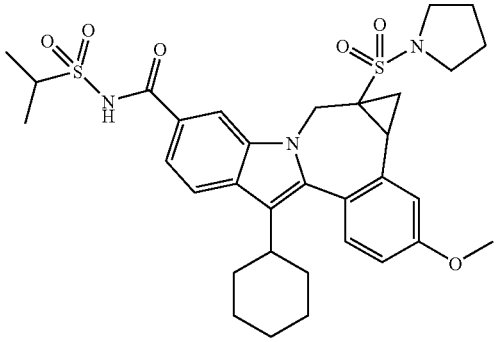

Cycloprop[d]indolo[2,1-a][2]benzazepine-5-carboxamide, 8-cyclohexyl-1,1a, 2,12b-tetrahydro-11-methoxy-N-[(1-methylethyl)sulfonyl]-1a-(1-pyrrolidinylsulfonyl)-. LCMS: m/e 640 (M+H), ret time 2.86 min, column A, 4 minute gradient, flow rate 4 mL/min.

EXAMPLE 53

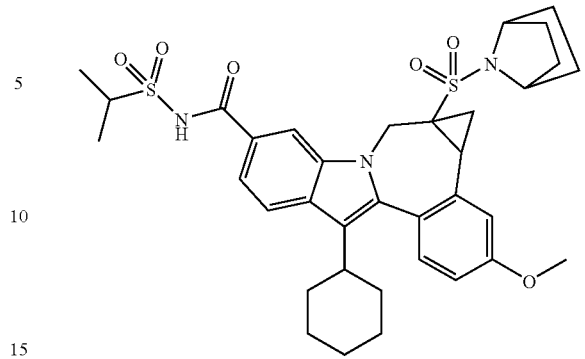

Cycloprop[d]indolo[2,1-a][2]benzazepine-5-carboxamide, 1a-(7-azabicyclo[2.2.1]hept-7-ylsulfonyl)-8-cyclohexyl-1,1a,2,12b-tetrahydro-11-methoxy-N-[(1-methylethyl)sulfonyl]-. LCMS: m/e 666 (M+H), ret time 3.09 min, column A, 4 minute gradient, flow rate 4 mL/min.

EXAMPLE 54

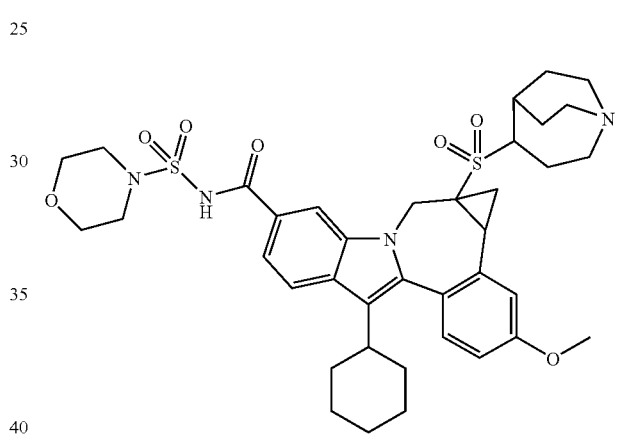

Cycloprop[d]indolo[2,1-a][2]benzazepine-5-carboxamide, 8-cyclohexyl-1a-(1,4-diazabicyclo[3.2.2]non-4-ylsulfonyl)-1,1a,2,12b-tetrahydro-11-methoxy-N-(4-morpholinyl-sulfonyl)-. LCMS: m/e 738 (M+H), ret time 2.45 min, column A, 4 minute gradient, flow rate 4 mL/min.

EXAMPLE 55

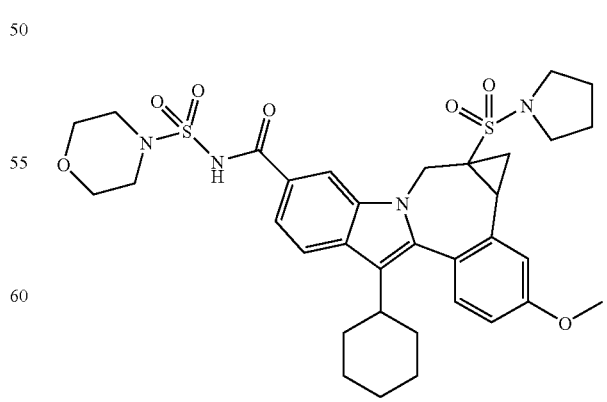

Cycloprop[d]indolo[2,1-a][2]benzazepine-5-carboxamide, 8-cyclohexyl-1,1a, 2,12b-tetrahydro-11-methoxy-N-(4- morpholinylsulfonyl)-1a-(1-pyrrolidinylsulfonyl)-. LCMS: m/e 683 (M+H), ret time 2.85 min, column A, 4 minute gradient, flow rate 4 mL/min.

EXAMPLE 56

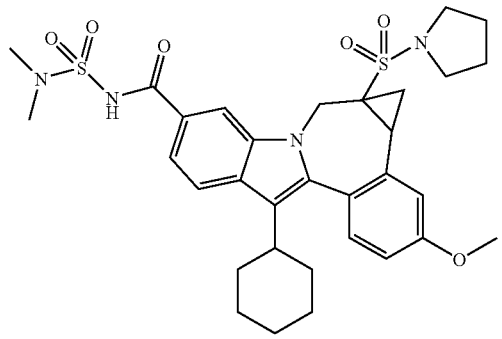

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-(1-pyrrolidinylsulfonyl)-.
LCMS: m/e 641 (M+H), ret time 3.19 min, column A, 4 minute gradient, flow rate 4 mL/min.

EXAMPLE 57

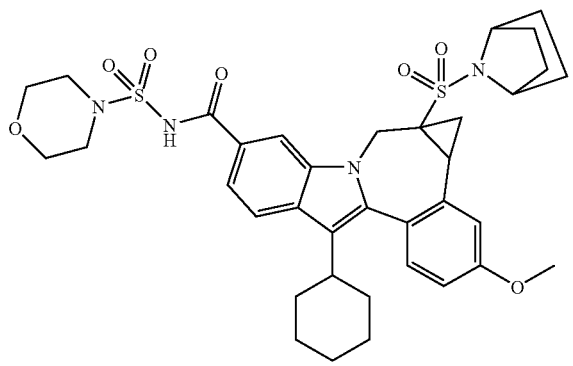

Cycloprop[d]indolo[2,1-a][2]benzazepine-5-carboxamide, 1a-(7-azabicyclo[2.2.1]hept-7-ylsulfonyl)-8-cyclohexyl-1,1a, 2,12b-tetrahydro-11-methoxy-N-(4-morpholinylsulfonyl)-. LCMS: m/e 709 (M+H), ret time 3.04 min, column A, 4 minute gradient, flow rate 4 mL/min.

EXAMPLE 58

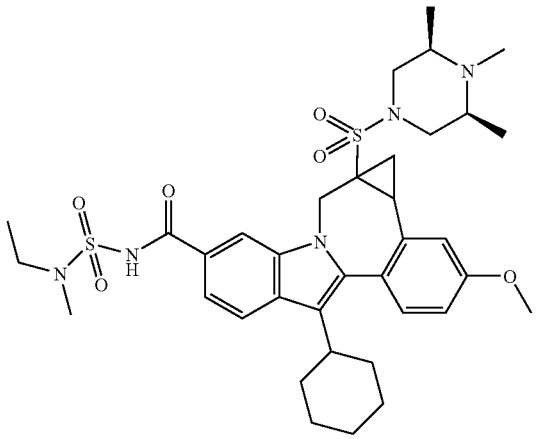

Cycloprop[d]indolo[2,1-a][2]benzazepine-5-carboxamide, 8-cyclohexyl-N-[(ethylmethylamino)sulfonyl]-1,1a,2,12b-tetrahydro-11-methoxy-1a-[(3,4,5-trimethyl-1-piperazinyl)sulfonyl]-. LCMS: m/e 712 (M+H), ret time 3.11 min, column A, 4 minute gradient, flow rate 4 mL/min.

EXAMPLE 59

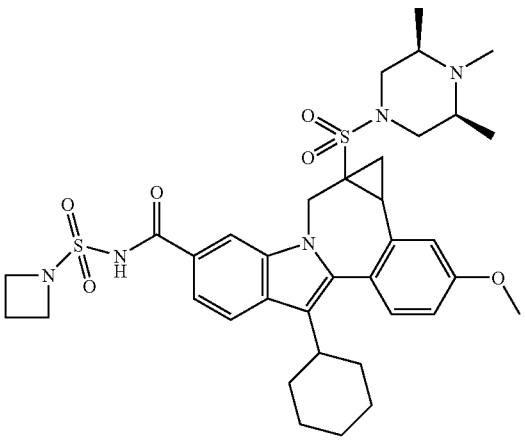

Cycloprop[d]indolo[2,1-a][2]benzazepine-5-carboxamide, N-(1-azetidinylsulfonyl)-8-cyclohexyl-1,1a,2,12b-tetrahydro-11-methoxy-1a-[(3,4,5-trimethyl-1-piperazinyl)sulfonyl]-. LCMS: m/e 710 (M+H), ret time 2.50 min, column A, 4 minute gradient, flow rate 4 mL/min.

EXAMPLE 60

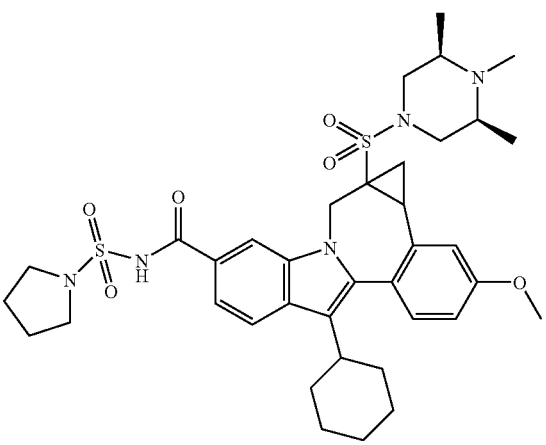

Cycloprop[d]indolo[2,1-a][2]benzazepine-5-carboxamide, 8-cyclohexyl-1,1a, 2,12b-tetrahydro-11-methoxy-N-(1-pyrrolidinylsulfonyl)-1a-[(3,4,5-trimethyl-1-piperazinyl)sulfonyl]-. LCMS: m/e 724 (M+H), ret time 3.13 min, column A, 4 minute gradient, flow rate 4 mL/min.

EXAMPLE 61

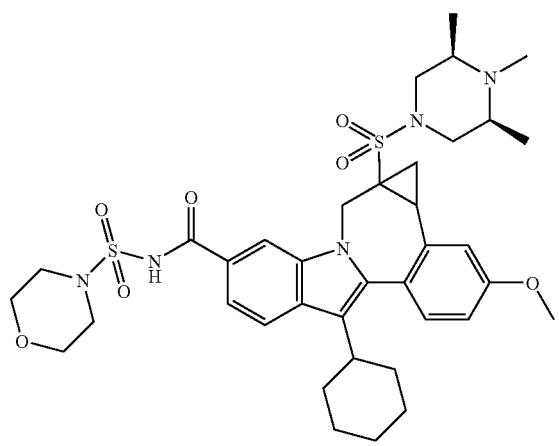

Cycloprop[d]indolo[2,1-a][2]benzazepine-5-carboxamide, 8-cyclohexyl-1,1a,2,12b-tetrahydro-11-methoxy-N-(4-morpholinylsulfonyl)-1a-[(3,4,5-trimethyl-1-piperazinyl)sulfonyl]-. LCMS: m/e 740 (M+H), ret time 2.53 min, column A, 4 minute gradient, flow rate 4 mL/min.

EXAMPLE 62

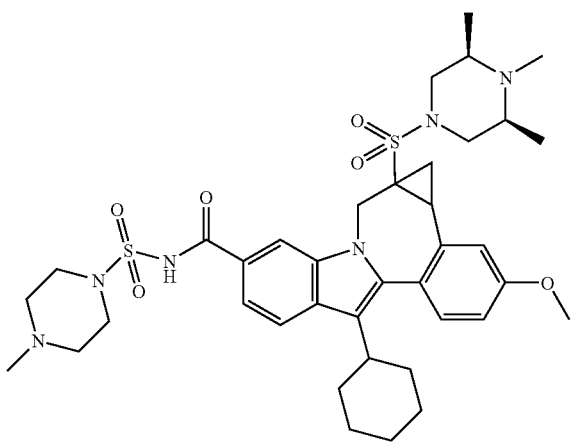

Cycloprop[d]indolo[2,1-a][2]benzazepine-5-carboxamide, 8-cyclohexyl-1,1a, 2,12b-tetrahydro-11-methoxy-N-[(4-methyl-1-piperazinyl)sulfonyl]-1a-[(3,4,5-trimethyl-1-piperazinyl)sulfonyl]-. LCMS: m/e 753 (M+H), ret time 2.14 min, column A, 4 minute gradient, flow rate 4 mL/min.

EXAMPLE 63

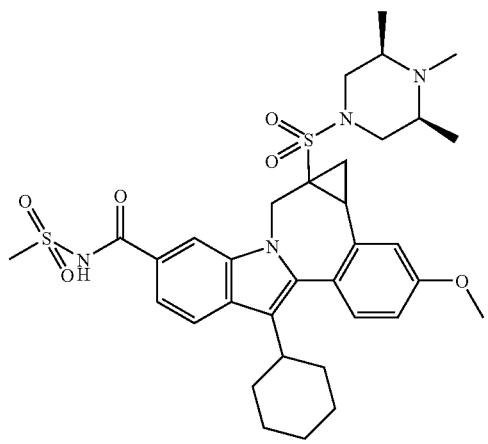

Cycloprop[d]indolo[2,1-a][2]benzazepine-5-carboxamide, 8-cyclohexyl-1,1a,2,12b-tetrahydro-11-methoxy-N-(methylsulfonyl)-1a-[(3,4,5-trimethyl-1-piperazinyl)sulfonyl]-. LCMS: m/e 669 (M+H), ret time 2.53 min, column A, 4 minute gradient, flow rate 4 mL/min.

EXAMPLE 64

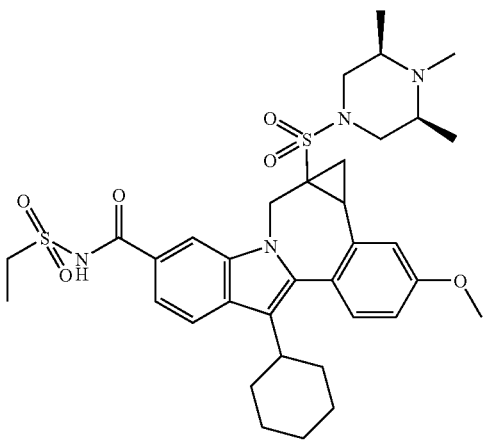

Cycloprop[d]indolo[2,1-a][2]benzazepine-5-carboxamide, 8-cyclohexyl-N-(ethylsulfonyl)-, 1,1a,2,12b-tetrahydro-11-methoxy-1a-[(3,4,5-trimethyl-1-piperazinyl)sulfonyl]-. LCMS: m/e 683 (M+H), ret time 2.68 min, column A, 4 minute gradient, flow rate 4 mL/min.

EXAMPLE 65

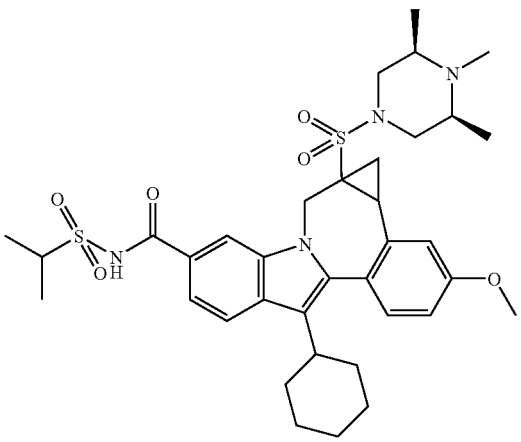

Cycloprop[d]indolo[2,1-a][2]benzazepine-5-carboxamide, 8-cyclohexyl-1,1a,2,12b-tetrahydro-11-methoxy-N-[(1-methylethyl)sulfonyl]-1a-[(3,4,5-trimethyl-1-piperazinyl)sulfonyl]-. LCMS: m/e 697 (M+H), ret time 2.82 min, column A, 4 minute gradient, flow rate 4 mL/min.

I claim:

1. A compound of formula I

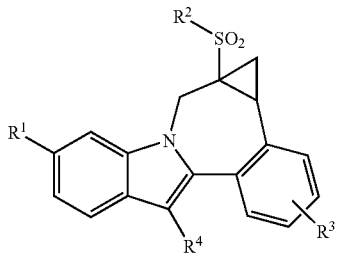

where:

$R^1$ is $CO_2R^5$ or $CONR^6R^7$;

$R^2$ is hydroxy, alkoxy, benzyloxy, amino, alkylamino, dialkylamino, (aminoalkyl)amino, (aminoalkyl)(alkyl)amino, di(aminoalkyl)amino, ((alkylamino)alkyl)amino, ((alkylamino)alkyl)(alkyl)amino, di((alkylamino)alkyl)amino, ((dialkylamino)alkyl)amino, ((dialkylamino)alkyl)(alkyl)amino, di((dialkylamino)alkyl)amino, (($COR^{11}$)alkyl)amino, (($COR^{11}$)alkyl)(alkyl)amino, alkyl, haloalkyl, aminoalkyl, (alkylamino)alkyl, (dialkylamino)alkyl, or ($R^{12}$)alkyl;

or $R^2$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from the group consisting of hydroxy, amino, alkylamino, dialkylamino, alkyl, alkoxyalkyl, aminoalkyl, (alkylamino)alkyl, (dialkylamino)alkyl, alkylSO$_2$, and haloalkylSO$_2$;

or $R^2$ is

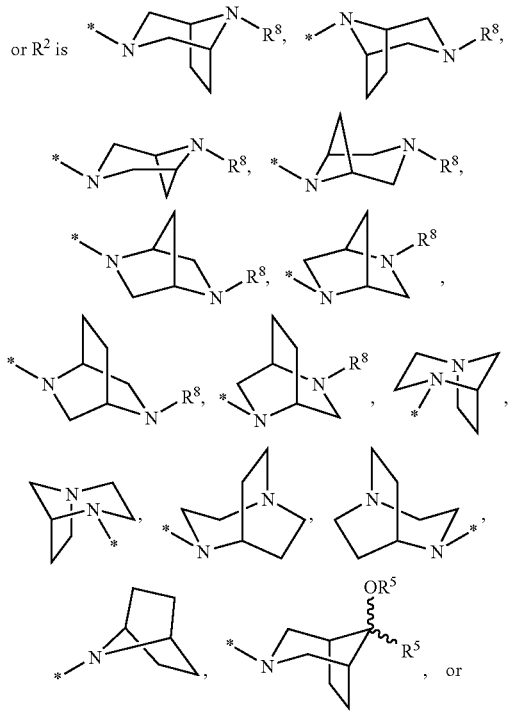

or $R^2$ is a [4.3.0] or [3.3.0] bicyclic diamine attached to the SO$_2$ moiety through one nitrogen, and is substituted with 0-2 $R^8$ substituents;

$R^3$ is hydrogen, halo, alkyl, alkenyl, hydroxy, benzyloxy, alkoxy, or haloalkoxy;

$R^4$ is cycloalkyl;

$R^5$ is hydrogen or alkyl;

$R^6$ is hydrogen, alkyl, alkylSO$_2$, cycloalkylSO$_2$, haloalkylSO$_2$, ($R^9$)$_2$NSO$_2$, or ($R^{10}$)SO$_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;

$R^9$ is hydrogen, alkyl, or cycloalkyl; and $R^{10}$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 alkyl substituents;

$R^{11}$ is azetidinyl, pyrrolidinyl, piperidinyl, piperazinyl, N-alkylpiperazinyl, morpholinyl, thiomorpholinyl, homopiperidinyl, homopiperazinyl, N-alkylhomopiperazinyl, or homomorpholinyl; and $R^{12}$ is azetidinyl, pyrrolidinyl, piperidinyl, piperazinyl, N-alkylpiperazinyl, morpholinyl, thiomorpholinyl, homopiperidinyl, homopiperazinyl, N-alkylhomopiperazinyl, or homomorpholinyl;

or a pharmaceutically acceptable salt thereof.

2. A compound of claim 1 where $R^1$ is $CONR^6R^7$; $R^6$ is alkylSO$_2$, cycloalkylSO$_2$, haloalkylSO$_2$, ($R^9$)$_2$NSO$_2$, or ($R^{10}$)SO$_2$; and $R^7$ is hydrogen.

3. A compound of claim 1 where $R^3$ is hydrogen.

4. A compound of claim 1 where $R^3$ is methoxy.

5. A compound of claim 1 where $R^4$ is cyclohexyl.

6. A compound of claim 1 where $R^6$ is alkylSO$_2$, ($R^9$)$_2$NSO$_2$ or ($R^{10}$)SO$_2$.

7. A compound of claim 1 where $R^8$ is hydrogen, alkyl, alkylSO$_2$, or benzyl.

8. A compound of claim 1 according to the following stereochemistry.

9. A compound of claim 1 according to the following stereochemistry.
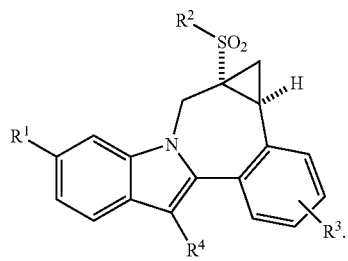
10. A compound of claim 1 selected from the group consisting of
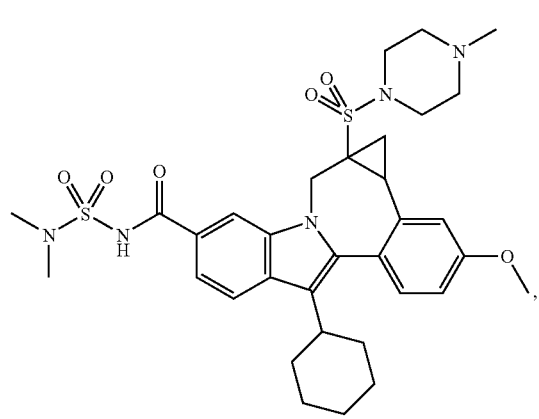
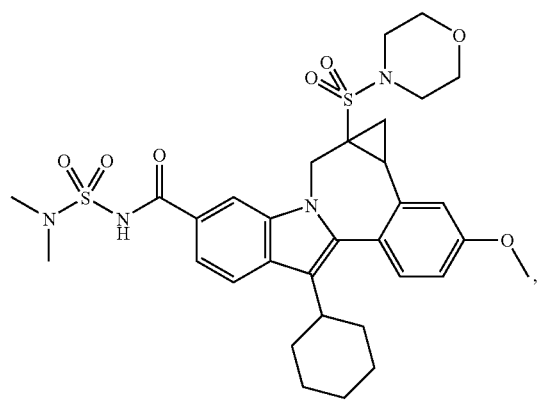
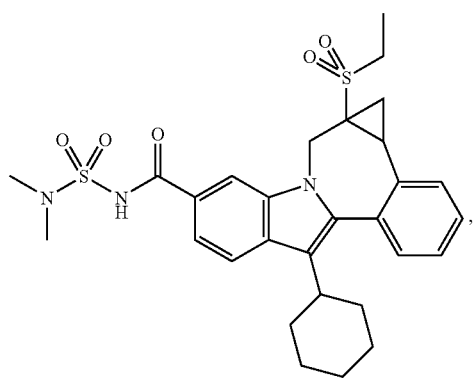
-continued
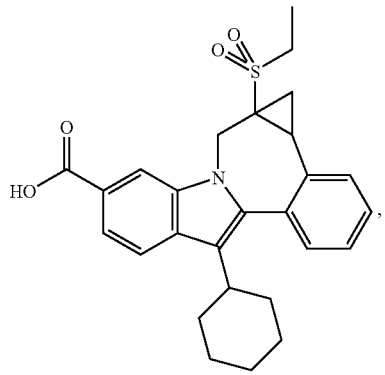
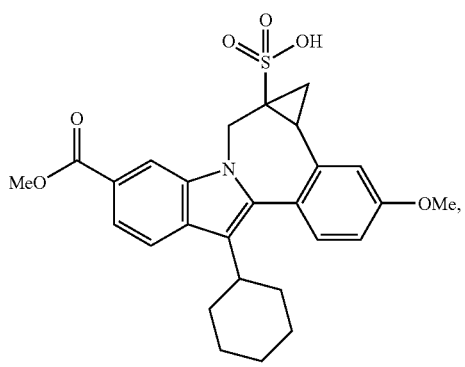
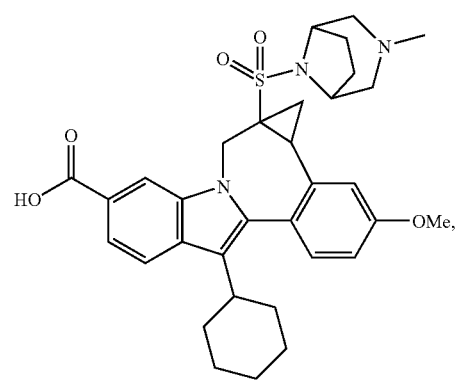
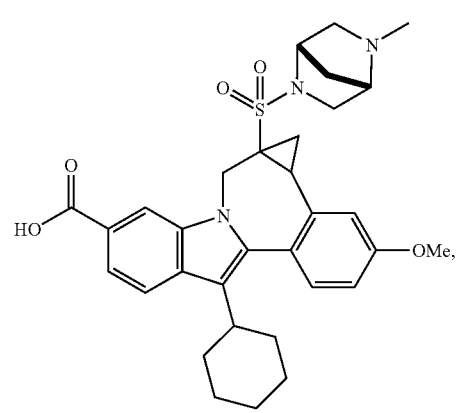

107
-continued
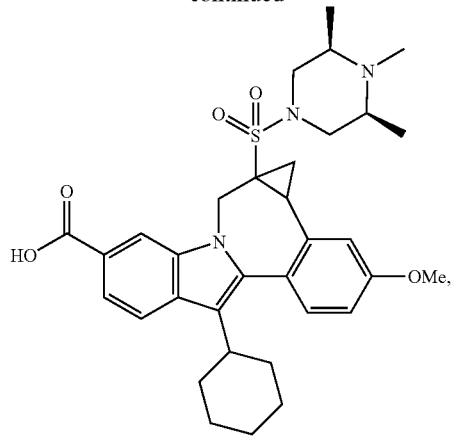
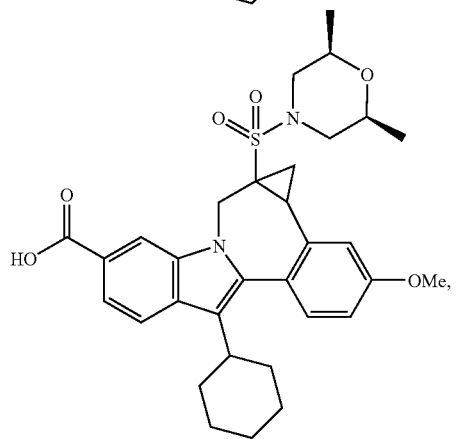
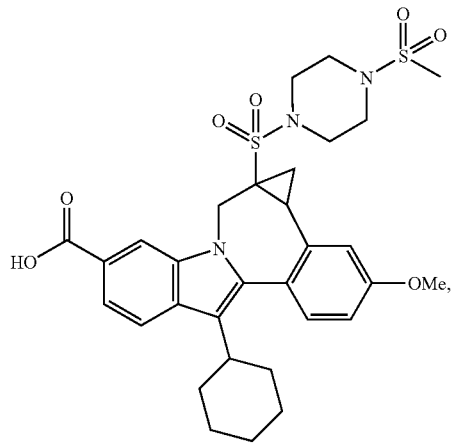
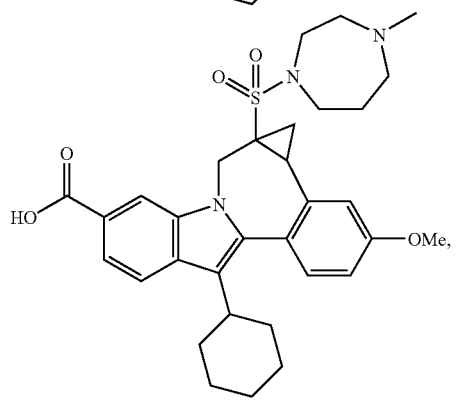
108
-continued
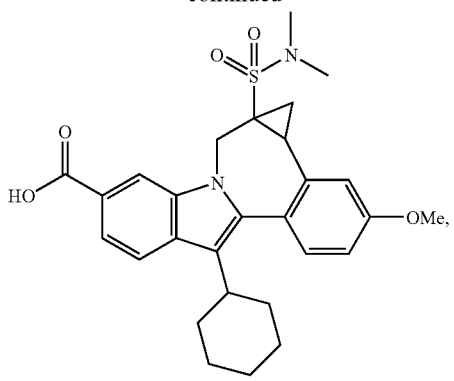
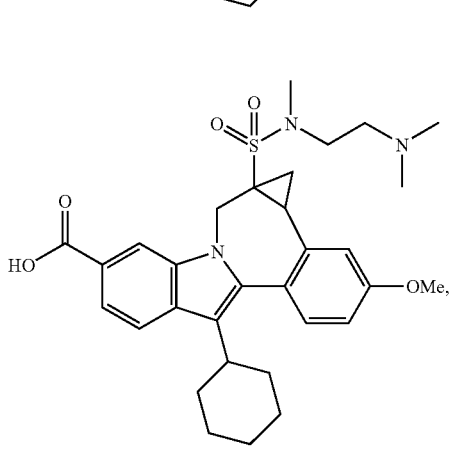
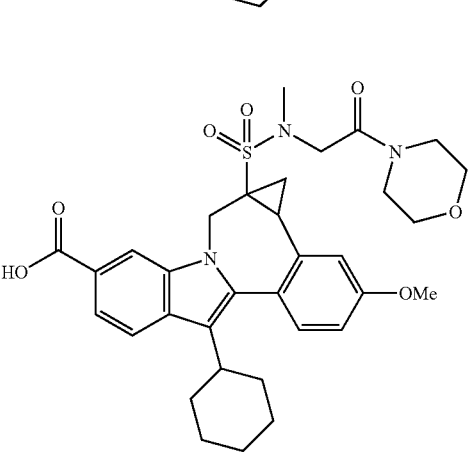
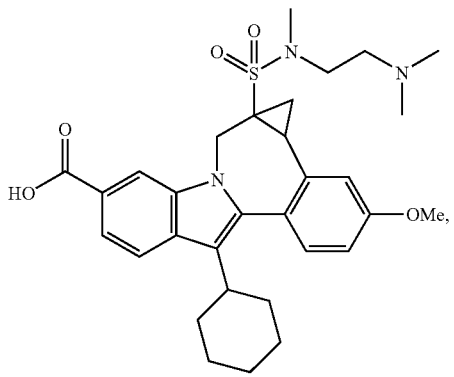

-continued
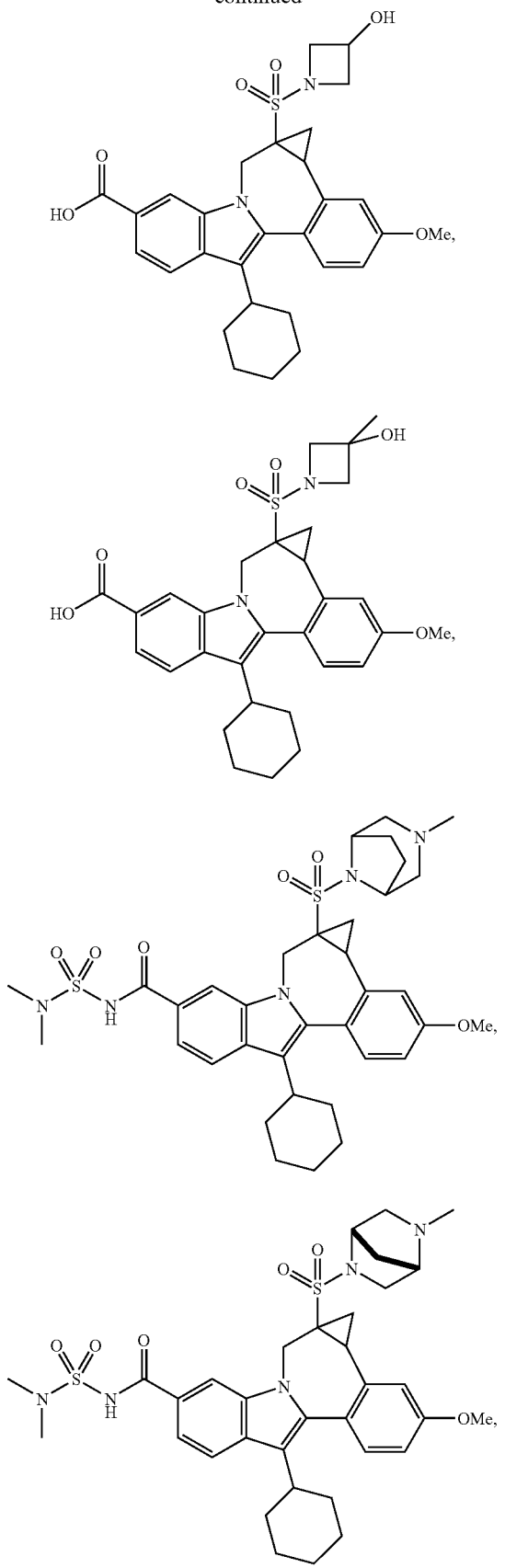
-continued
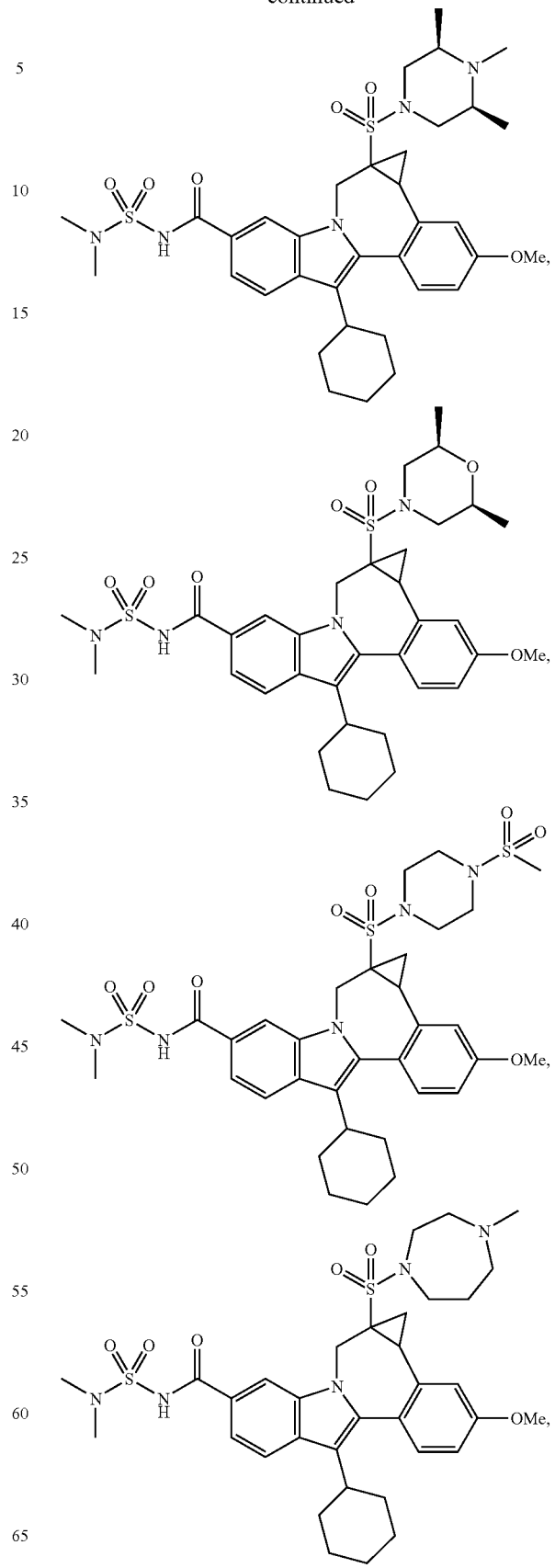

111 -continued
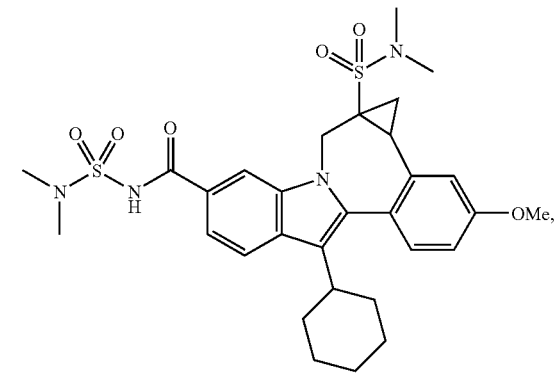
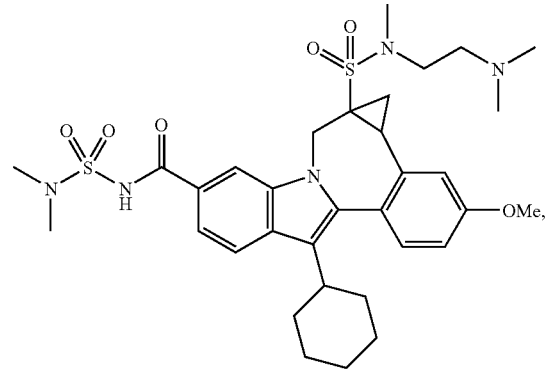
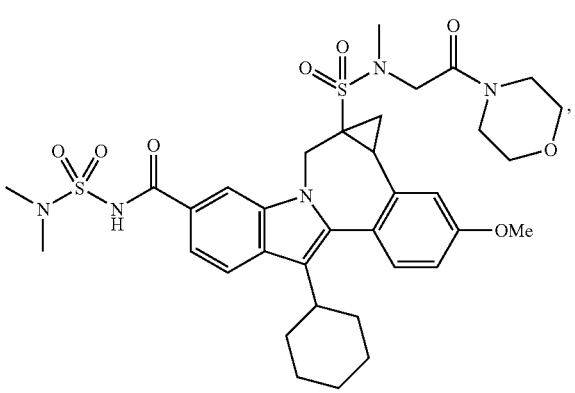
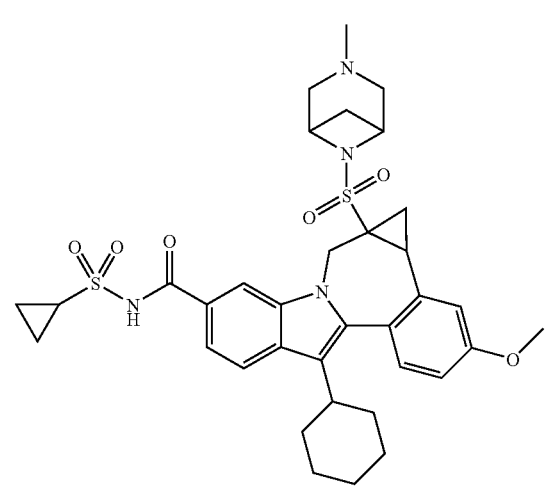
112 -continued
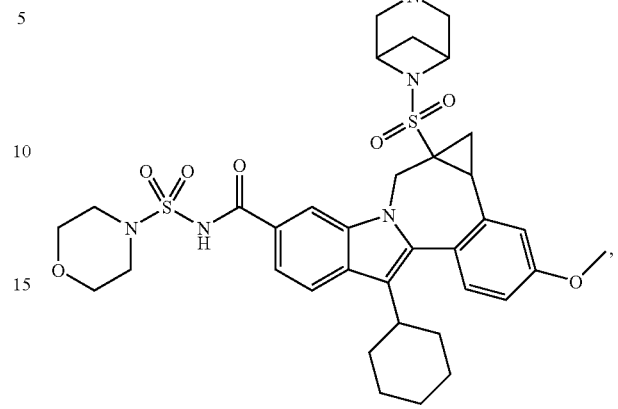
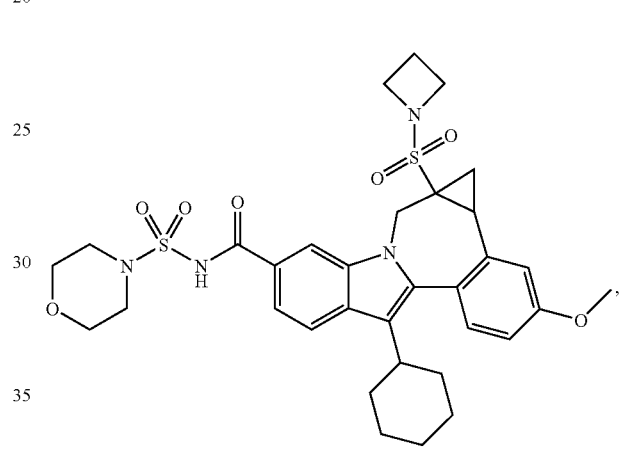
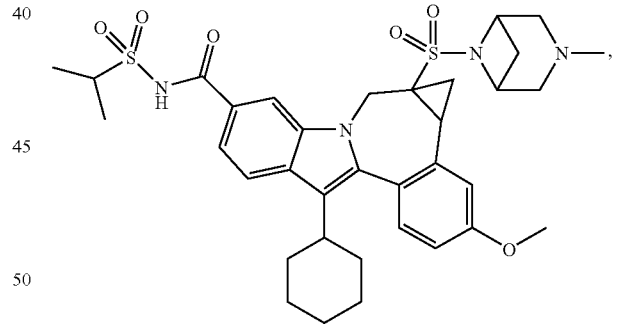
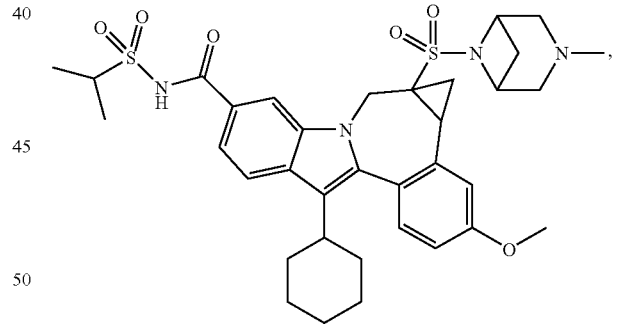
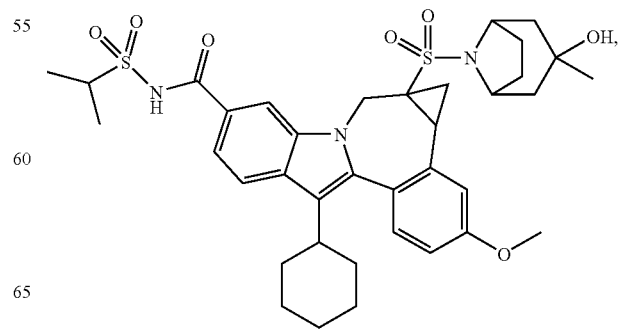

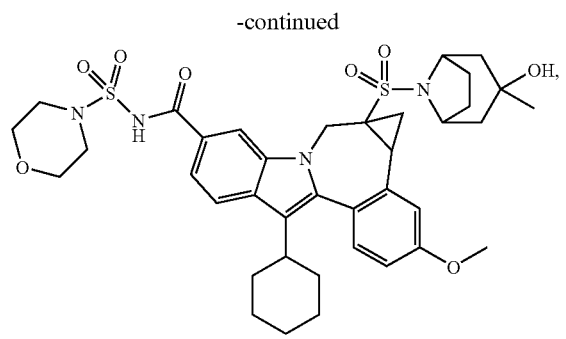
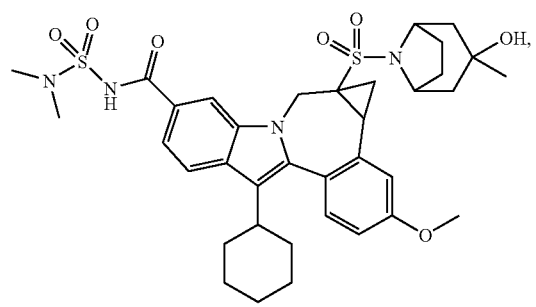
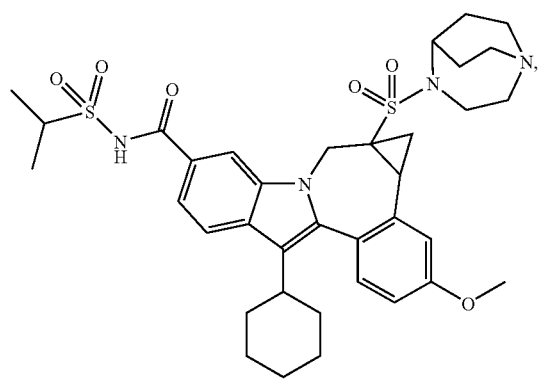
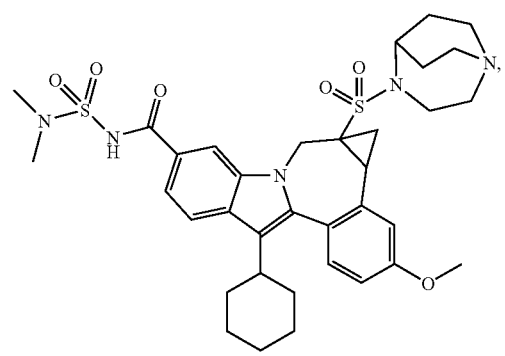
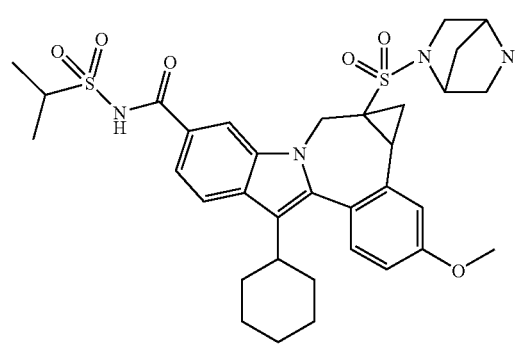
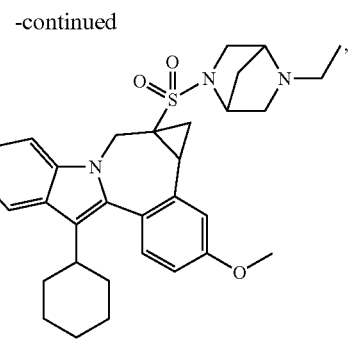
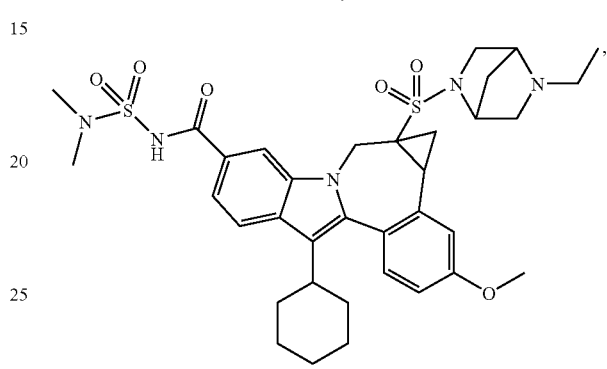
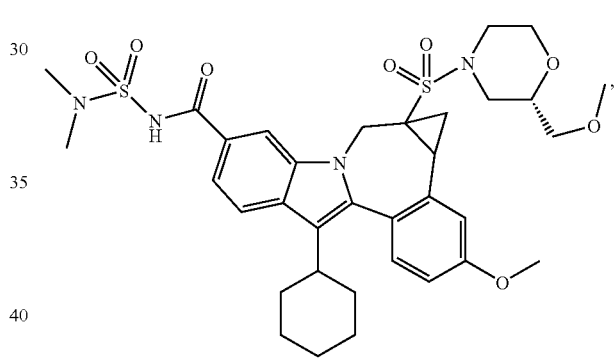
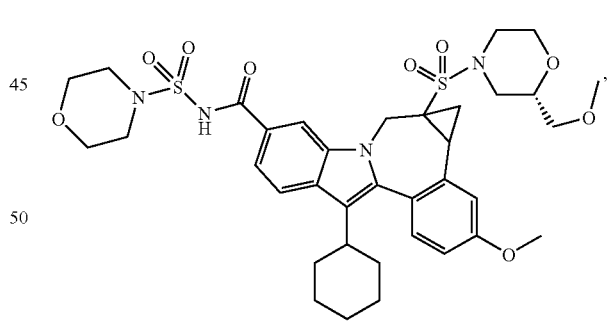
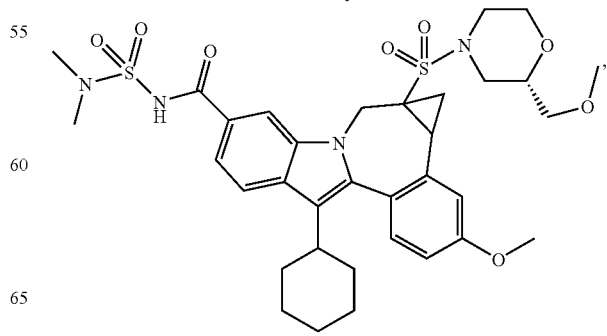

115
-continued
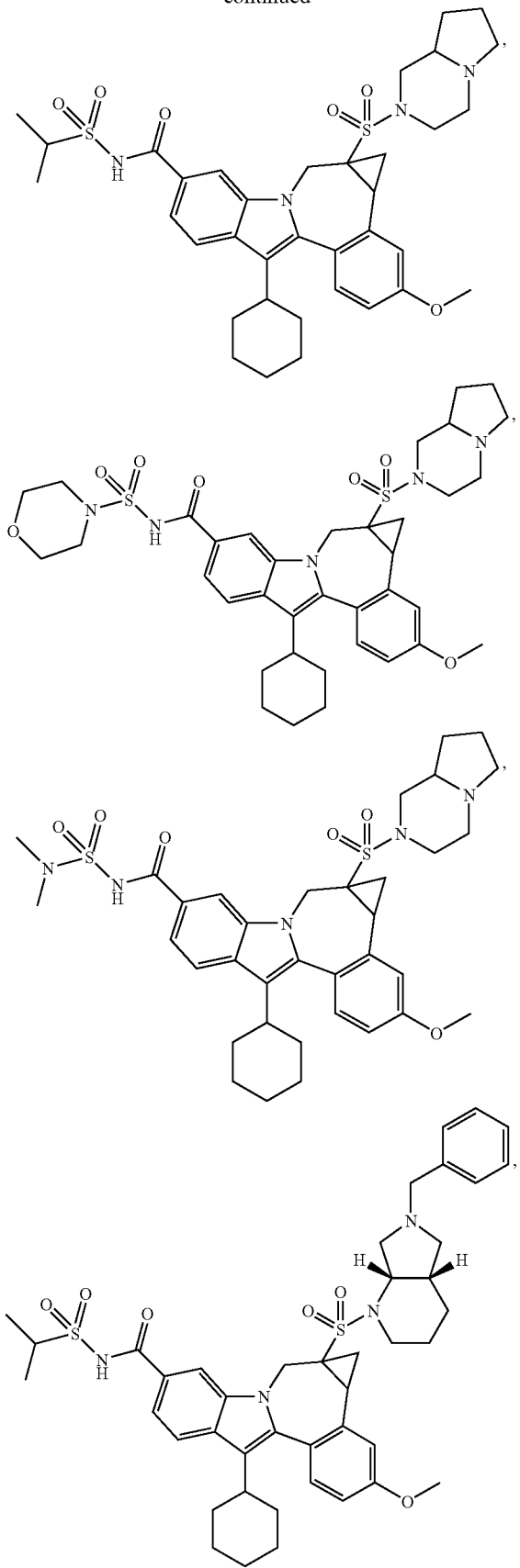
116
-continued
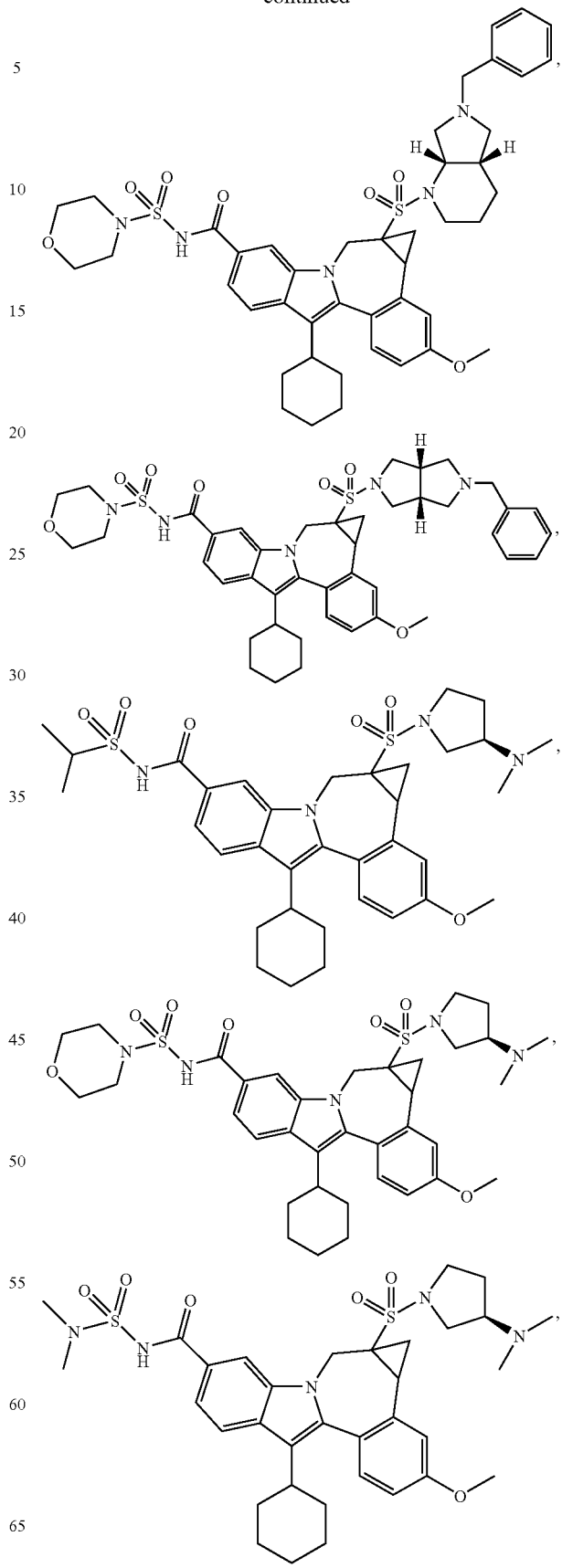

117
-continued
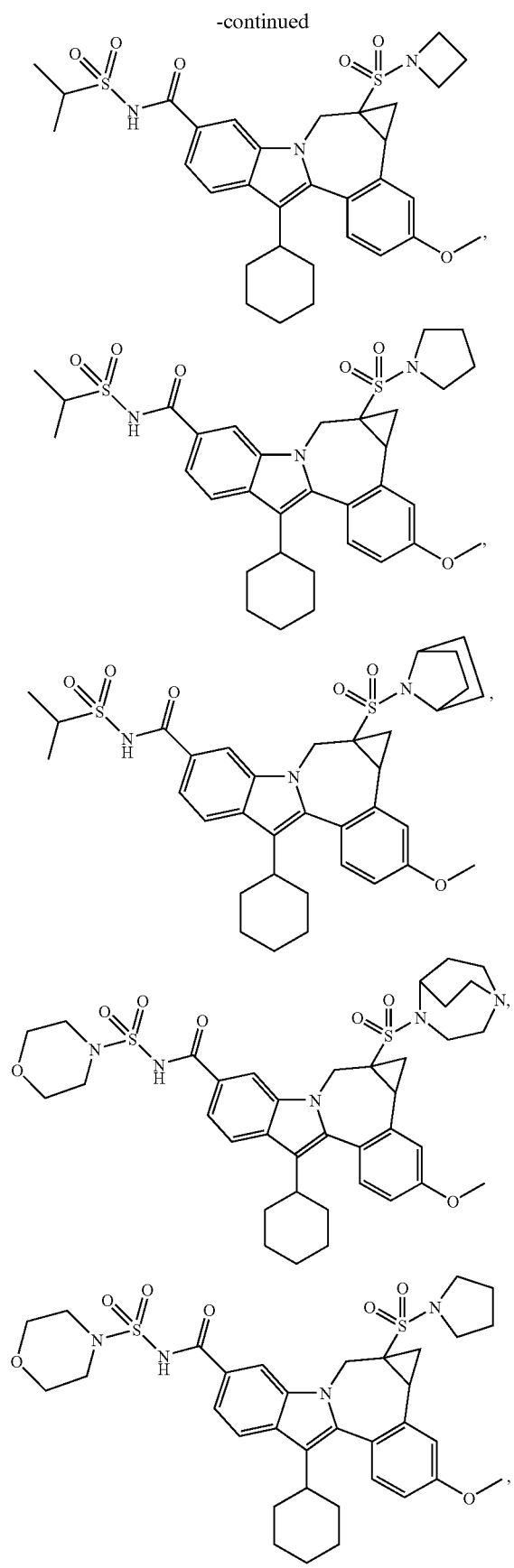
118
-continued
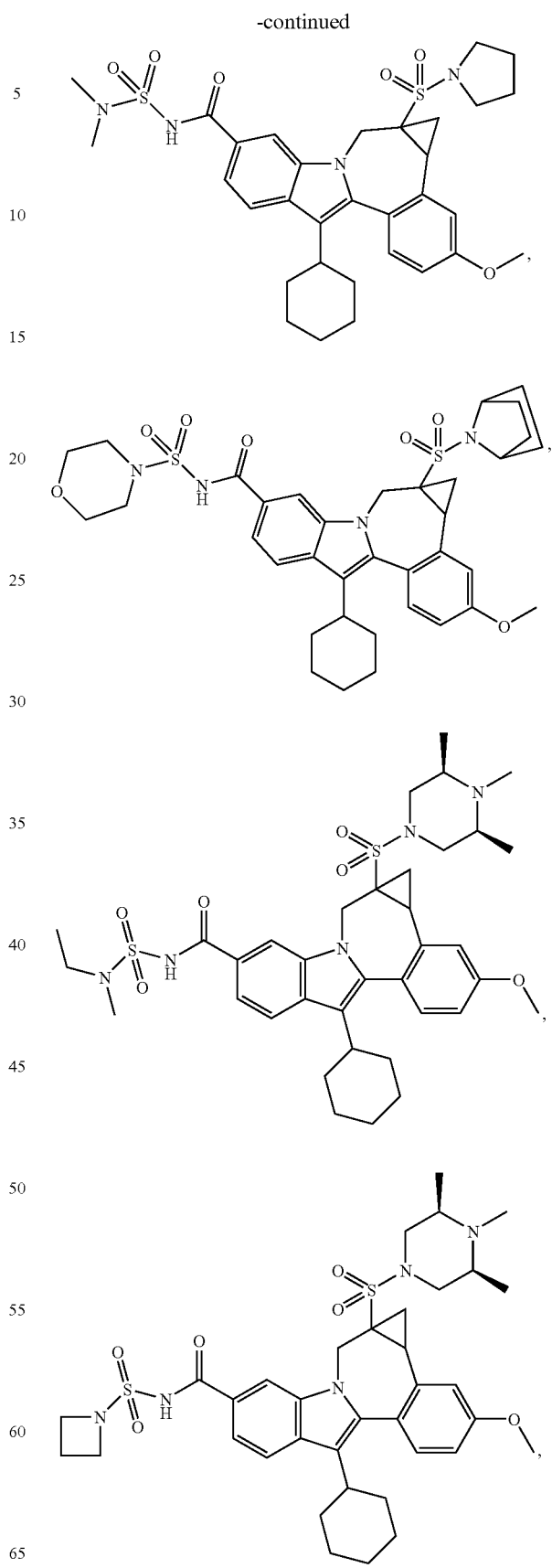

-continued
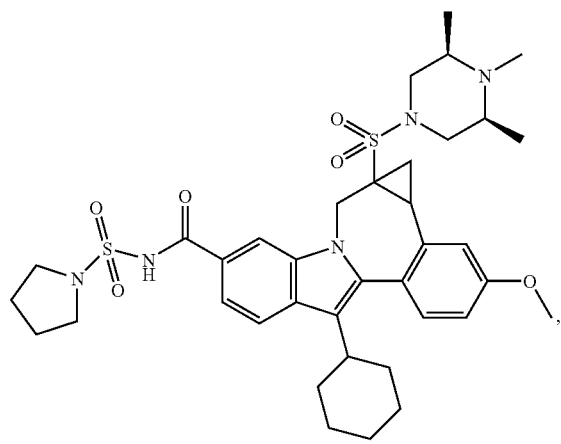
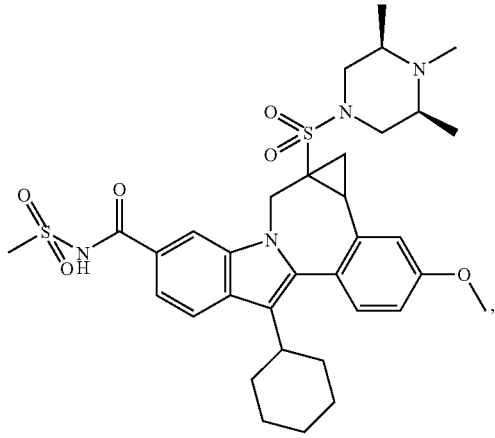
or a pharmaceutically acceptable salt thereof.
11. A composition comprising a compound of claim 1, or a pharmaceutically acceptable salt thereof, and a pharmaceutically acceptable carrier.
12. A method of treating hepatitis C infection comprising administering a therapeutically effective amount of a compound of claim 1 to a patient.
* * * * *